US012751761B2

(12) United States Patent
Dunki-Jacobs et al.

(10) Patent No.: US 12,751,761 B2
(45) Date of Patent: Oct. 6, 2026

(54) TISSUE MONITORING ELECTROSURGICAL INSTRUMENTS AND METHODS OF USING THE SAME

(71) Applicant: Standard Bariatrics, Inc., Cincinnati, OH (US)

(72) Inventors: Adam R. Dunki-Jacobs, Cincinnati, OH (US); Jonathan R. Thompson, Cincinnati, OH (US); Robert T. Means, III, Cincinnati, OH (US); Trevor J. Barton, Cincinnati, OH (US)

(73) Assignee: Standard Bariatrics, Inc., Cincinnati, OH (US)

(*) Notice: Subject to any disclaimer, the term of this patent is extended or adjusted under 35 U.S.C. 154(b) by 0 days.

(21) Appl. No.: 18/243,365

(22) Filed: Sep. 7, 2023

(65) Prior Publication Data

US 2024/0081891 A1 Mar. 14, 2024

Related U.S. Application Data

(60) Provisional application No. 63/404,578, filed on Sep. 8, 2022.

(51) Int. Cl.
*A61B 18/12* (2006.01)
*A61B 17/072* (2006.01)
(Continued)

(52) U.S. Cl.
CPC ........ *A61B 18/1445* (2013.01); *A61B 17/072* (2013.01); *A61B 2017/07257* (2013.01);
(Continued)

(58) Field of Classification Search
CPC .............. A61B 18/1445; A61B 18/085; A61B 2018/00708; A61B 2018/00791;
(Continued)

(56) References Cited

U.S. PATENT DOCUMENTS

| | | | | |
|---|---|---|---|---|
| 5,531,744 A * | 7/1996 | Nardella | A61B 18/1447 606/41 |
| 2009/0182323 A1* | 7/2009 | Eder | A61B 18/1442 606/50 |

(Continued)

OTHER PUBLICATIONS

International Search Report and Written Opinion of the International Searching Authority received in International Patent App. No. PCT/US2023/032187; mailed Feb. 5, 2024; 9 pages.

(Continued)

*Primary Examiner* — Daniel W Fowler
(74) *Attorney, Agent, or Firm* — BakerHostetler

(57) ABSTRACT

An electrosurgical surgical instrument comprising an end effector, the end effector comprising an anvil; a cartridge operably configured to house a plurality of staples; a blade assembly comprising a blade; at least one electrode coupled to the blade, wherein the at least one electrode is in electrical communication with an electrosurgical power source generated from a controller; and at least one tissue sensor coupled to the blade; and a tissue monitoring system in electrical communication with the at least one tissue sensor, wherein the at least one tissue sensor provides feedback signals indicative of a property of the tissue to the controller, and wherein the controller signals the electrosurgical power source to adjust operational parameters of the electrosurgical surgical instrument based on the feedback signals.

16 Claims, 31 Drawing Sheets

(51) Int. Cl.
*A61B 18/14* (2006.01)
*A61B 18/00* (2006.01)

(52) U.S. Cl.
CPC ............... *A61B 2017/07285* (2013.01); *A61B 2018/00601* (2013.01); *A61B 2018/0063* (2013.01); *A61B 2018/00708* (2013.01); *A61B 2018/00791* (2013.01); *A61B 2018/00875* (2013.01); *A61B 2018/1452* (2013.01)

(58) Field of Classification Search
CPC .. A61B 2018/00875; A61B 2018/1452; A61B 2018/00589
See application file for complete search history.

(56) References Cited

U.S. PATENT DOCUMENTS

| | | | | |
|---|---|---|---|---|
| 2010/0076427 | A1* | 3/2010 | Heard ................ | A61B 18/1442 606/45 |
| 2011/0238062 | A1* | 9/2011 | Koss ...................... | A61B 18/18 606/34 |
| 2012/0116379 | A1 | 5/2012 | Yates et al. | |
| 2014/0110455 | A1* | 4/2014 | Ingmanson .......... | A61B 17/072 227/176.1 |
| 2014/0249524 | A1* | 9/2014 | Kocur ................ | A61B 18/1492 607/113 |
| 2014/0276731 | A1 | 9/2014 | Voegele et al. | |
| 2018/0049820 | A1* | 2/2018 | Widenhouse .......... | A61B 34/37 |
| 2019/0000565 | A1* | 1/2019 | Shelton, IV ........... | A61B 34/30 |
| 2019/0046193 | A1* | 2/2019 | Dunki-Jacobs .... | A61B 17/0644 |
| 2019/0125432 | A1* | 5/2019 | Shelton, IV ....... | A61B 17/1285 |
| 2020/0268385 | A1 | 8/2020 | Dunki-Jacobs et al. | |
| 2020/0405414 | A1 | 12/2020 | Shelton, IV et al. | |
| 2021/0212681 | A1* | 7/2021 | Eschbach ......... | A61B 17/07207 |

OTHER PUBLICATIONS

European Patent Application No. 23863790.4, Extended European Search Report, dated Jul. 13, 2026; 06 pages; 1 European Patent Office.

* cited by examiner

TISSUE MONITORING ELECTROSURGICAL INSTRUMENTS AND METHODS OF USING THE SAME

CROSS-REFERENCE TO RELATED APPLICATIONS

This patent application claims the benefit of U.S. Provisional Patent Application Ser. No. 63/404,578 filed on Sep. 8, 2022 and entitled "Tissue Monitoring Electrosurgical Instruments and Methods of Using the Same", the disclosure of which is hereby incorporated by reference herein in its entirety and made part of the present U.S. utility patent application for all purposes.

TECHNICAL FIELD

Embodiments of the disclosed technology relate, in general, to electrosurgical surgical technology, and in particular to end effectors and stapling devices and methods of using those devices in surgical procedures to deliver energy to tissue and receive signals from a tissue sensor based on the real-time status of the tissue.

SUMMARY

The following provides a summary of certain example implementations of the disclosed technology. This summary is not an extensive overview and is not intended to identify key or critical aspects or elements of the disclosed technology or to delineate its scope. However, it is to be understood that the use of indefinite articles in the language used to describe and claim the disclosed technology is not intended in any way to limit the described technology. Rather the use of "a" or "an" should be interpreted to mean "at least one" or "one or more".

One implementation of the disclosed technology provides an electrosurgical surgical instrument. The surgical instrument comprises an end effector, the end effector comprising an anvil that includes a first end, a second end, and an anvil face positionable on a first side of an anatomical structure; a cartridge operably configured to house a plurality of staples, the cartridge comprising a first end, a second end, and a face positionable on a second side of the anatomical structure; a blade assembly comprising a blade, wherein the blade includes a first side and a second side joined at a cutting edge; at least one electrode coupled to the blade, wherein the at least one electrode is in electrical communication with an electrosurgical power source generated from a controller; and at least one tissue sensor coupled to the blade; and a tissue monitoring system in electrical communication with the at least one tissue sensor, wherein the at least one tissue sensor provides feedback signals indicative of a property of the tissue to the controller, and wherein the controller signals the electrosurgical power source to adjust operational parameters of the electrosurgical surgical instrument based on the feedback signals.

As the blade is advanced from a first position at a distal end of the cartridge to a second position at a proximal end of the cartridge an incision is formed in the anatomical structure and the at least one electrode and the at least one tissue sensor contact the anatomical structure and translate along the anatomical structure. The controller may include analog or logic circuitry for processing the feedback signals received from the at least one tissue sensor and determining the signals sent to the electrosurgical power source. Circuitry may connect the at least one electrode to the electrosurgical power source and the at least one tissue sensor to the tissue monitoring system. The feedback signals may relate to tissue temperature of the anatomical structure. The electrosurgical power source is terminated once the tissue temperature rises above a predetermined threshold. The predetermined threshold of the tissue temperature may be between 80-120° C. Firing speed of the electrosurgical surgical instrument is decreased if the tissue temperature at a predetermined tissue location of the anatomical structure has not reached a target temperature. The target temperature of the predetermined tissue location may be between 60-100° C. The feedback signals may relate to tissue impedance of the anatomical structure. The electrosurgical power source is terminated if the tissue impedance at a predetermined tissue location of the anatomical structure has not reached a target impedance such as, for example, 200 Ohms. Firing speed of the electrosurgical surgical instrument is decreased if the tissue impedance rises above a predetermined threshold value, such as, for example, 600 Ohms.

Another implementation of the disclosed technology provides an electrosurgical surgical instrument for stapling, resecting, and sealing an anatomical structure of a patient. The surgical instrument comprises an end effector, the end effector comprising an anvil that includes a first end, a second end, and an anvil face positionable on a first side of the anatomical structure; a cartridge operably configured to house a plurality of staples, the cartridge comprising a first end, a second end, and a face positionable on a second side of the anatomical structure; a blade assembly comprising a blade and a beam, wherein the blade includes a first side and a second side joined at a cutting edge; at least one electrode coupled to the blade, wherein the at least one electrode is in electrical communication with an electrosurgical power source generated from a controller; and at least one tissue sensor coupled to the blade; and a tissue monitoring system in electrical communication with the at least one tissue sensor, wherein the at least one tissue sensor provides tissue impedance feedback signals to the controller as the blade is advanced from a first position at a distal end of the cartridge to a second position at a proximal end of a cartridge, and wherein the controller signals the electrosurgical power source to adjust firing speed of the electrosurgical surgical instrument based on the tissue impedance feedback signals.

As the blade is advanced from the first position at the distal end of the cartridge to the second position at the proximal end of the cartridge, an incision is formed in the anatomical structure and the at least one electrode and the at least one tissue sensor contact the anatomical structure and translate along the anatomical structure. The controller may include analog or logic circuitry for processing the feedback signals received from the at least one tissue sensor and determining the signals sent to the electrosurgical power source. The electrosurgical power source is terminated if the tissue impedance at a predetermined tissue location of the anatomical structure has not reached a target impedance such as, for example, 200 Ohms. The firing speed of the electrosurgical surgical instrument is decreased if the tissue impedance rises above a predetermined threshold value such as, for example, 600 Ohms. The at least one tissue sensor may further provide tissue temperature feedback signals to the controller. Firing speed of the electrosurgical surgical instrument is decreased if the tissue temperature at a predetermined tissue location of the anatomical structure has not reached a target temperature. The target temperature of the predetermined tissue location may be between 60-100° C. The electrosurgical power source is terminated once the tissue temperature rises above a predetermined threshold such as, for example, between 80-120° C.

Certain embodiments of the disclosed technology include an end effector for use by a surgeon to staple an anatomical structure of a patient, the end effector including a first jaw having a first end, a second end, a longitudinal axis, and an anvil having an anvil face; a second jaw having a first end, a second end, a longitudinal axis, and a cartridge operably configured to house a plurality of staples, the cartridge having a cartridge face; a first coupling that couples the first end of the first jaw to the first end of the second jaw; and a second coupling that movably couples the second end of the first jaw to the second end of the second jaw. Certain embodiments include a blade having a cutting surface and at least one lateral arm. Certain embodiments include a channel defined by the first jaw or the second jaw to retain the at least one lateral arm of the blade. In certain embodiments, the blade is transitioned from a first position at a distal end of the end effector to a second position at a proximal end of the end effector such that the anatomical structure is resected. Certain embodiments include a plurality of electrodes coupled to one side of the blade, such that the plurality of electrodes contact the anatomical structure during resection to effect hemostasis by heating the tissue and blood vessels to cauterize, coagulate/desiccate, and/or seal tissue on the one side of the blade. Certain embodiments further include at least one tissue sensor coupled to the blade proximate to the electrodes.

In certain embodiments, the first end of the first jaw is a distal end of the first jaw and the second end of the first jaw is a proximal end of the first jaw. In certain embodiments, the first coupling comprises a pin having a pin axis, the pin axis being transverse to the longitudinal axis of the first jaw and the longitudinal axis of the second jaw, wherein the pin pivotally couples the first end of the first jaw to the first end of the second jaw. In certain embodiments, the second coupling comprises a slot defined by the first jaw or the second jaw that retains the rigid link such that the rigid link is slidable within the slot. In certain embodiments, the slot has a length of from 3 millimeters to 8 millimeters. Certain embodiments include a plurality of staples at least partially retained by the cartridge of the second jaw. In certain embodiments, the plurality of staples retained at least partially by the cartridge are positioned between the first coupling and the second coupling. Certain embodiments include a blade having a cutting surface, at least one lateral arm, and first and second electrodes and a tissue sensor coupled to one side of the blade. In certain embodiments, the first and second electrodes are in electrical communication with an electrosurgical power generating source, such as a bipolar energy source, and the tissue sensor is in electrical communication with a tissue monitoring system. Certain embodiments include a channel defined by the first jaw or the second jaw to retain the at least one lateral arm of the blade. In certain embodiments, the blade is transitioned from a first position at a distal end of the end effector to a second position at a proximal end of the end effector such that the anatomical structure is resected. In certain embodiments, energy is delivered by the first and second electrodes to effect hemostasis of the anatomical structure during resection, where the first electrode is an active electrode and the second electrode is a return electrode. The operational parameters, including firing speed of the electrosurgical device, can be varied based on the real-time signaling received from the tissue sensor.

Certain embodiments of the disclosed technology provide a method of stapling and effecting hemostasis of an anatomical structure of a patient during a minimally invasive procedure, the anatomical structure having a first side and a second side, include the steps of providing an end effector including a first jaw having a first end, a second end, a longitudinal axis, and an anvil, the anvil having an anvil face; a second jaw having a first end, a second end, a longitudinal axis, and a cartridge retaining a plurality of staples, the cartridge having a cartridge face; a first coupling that couples the first end of the first jaw to the first end of the second jaw; a second coupling that movably couples the second end of the first jaw to the second end of the second jaw; a knife coupled with and slidable relative to the first jaw or the second jaw, an active electrode and a return electrode coupled to the knife, and at least one tissue sensor coupled to the knife; inserting the end effector through a trocar to access the anatomical structure; positioning the cartridge face on the first side of the anatomical structure; positioning the anvil face on the second side of the anatomical structure; operating the end effector to move the rigid link such that the first jaw is urged towards the second jaw to clamp the end effector on the anatomical structure; operating the end effector to urge the plurality of staples from the cartridge to staple the anatomical structure; actuating the knife to cut the anatomical structure; effecting hemostasis of the anatomical structure by applying energy to the active electrode, pass it through the anatomical structure and to the return electrode; monitoring a status of the tissue at the hemostasis site with the tissue sensor.

Certain embodiments of the disclosed technology provide a surgical instrument for stapling, resecting, and sealing an anatomical structure of a patient, the surgical instrument including an end effector, the end effector including a first jaw having a first end, a second end, a longitudinal axis, and an anvil, the anvil having an anvil face positionable on the first side of the anatomical structure; a second jaw having a first end, a second end, a longitudinal axis, and a cartridge operably configured to house a plurality of staples, the cartridge having a cartridge face positionable on the second side of the anatomical structure; a first coupling that couples the first end of the first jaw to the first end of the second jaw; and a second coupling that movably couples the second end of the first jaw to the second end of the second jaw, where the second coupling includes a rigid link connected to the first jaw and the second jaw; an elongate tube, the elongate tube having a proximal end and a distal end, where the distal end is coupled with the end effector; a handle, the handle having a proximal end and a distal end, where the distal end of the handle is coupled with the proximal end of the elongate tube; and a drive assembly including a motor to actuate the end effector. In certain embodiments the end effector includes a first and second electrodes in communication with an electrosurgical power generating source, such as a bipolar energy source. The first and second electrodes serve to collectively ablate, coagulate, cauterize, seal or otherwise treat biological tissue during a surgical procedure. In certain embodiments the end effector includes a tissue sensor in communication with a tissue monitoring system.

Certain embodiments of the disclosed technology provide a method of stapling, resecting, and sealing an anatomical structure of a patient during a minimally invasive procedure, the anatomical structure having a first side and a second side, the method including the steps of providing an end effector including an anvil having a first end, a second end, an anvil face, a length, and a width, where the length of the anvil is at least ten times the width of the anvil; a cartridge having a first end, a second end, a cartridge face, a length, and a width, where the length of the cartridge is at least ten times the width of the anvil, the cartridge retaining a plurality of staples, where the first end of the anvil is coupled with the first end of the cartridge and the second end of the anvil is movably coupled to the second end of the cartridge; and a rigid link having a distal portion and a proximal portion, where the rigid link movably couples the second end of the anvil to the second end of the cartridge; inserting the end effector through a trocar to access the anatomical structure; positioning the cartridge face on the first side of the anatomical structure; positioning the anvil face on the second side of the anatomical structure; operating the end effector to move the rigid link such that the anvil is urged towards the cartridge to clamp the end effector on the anatomical structure; operating the end effector to urge the plurality of staples from the cartridge to staple the anatomical structure; actuating a knife to cut the anatomical structure; applying energy to the anatomical structure through electrodes positioned on one side of the knife during actuation of the electrodes; and electronically monitoring at least one parameter of the anatomical structure as the anatomical structure is cut.

Certain embodiments of the disclosed technology provide a method of stapling, resecting, and sealing an anatomical structure of a patient during a minimally invasive procedure, the anatomical structure having a first side and a second side, the method including the steps of providing an end effector including an anvil that includes a first end, a second end, and an anvil face; a cartridge retaining a plurality of staples, the cartridge having a first end, a second end, and a cartridge face, the cartridge face including a channel extending from the first end of the cartridge to the second end of the cartridge, where the first end of the cartridge is pivotally coupled with the first end of the anvil; a blade, the blade having a cutting surface, first and second electrodes and a tissue sensor coupled to only one side of the blade, and at least one elongated arm, where the at least one elongated arm is slidably engaged with the channel; inserting the end effector through a trocar to access the anatomical structure; positioning the cartridge face on the first side of the anatomical structure; positioning the anvil face on the second side of the anatomical structure; clamping the end effector on the anatomical structure; operating the end effector to urge the plurality of staples from the cartridge to staple the anatomical structure; actuating the blade to cut the anatomical structure; applying bipolar energy to the anatomical structure via circuitry comprising the first and second electrodes; monitoring a temperature of the anatomical structure via the tissue sensor.

Certain embodiments of the disclosed technology provide a method of stapling, resecting, and sealing an anatomical structure of a patient during a minimally invasive procedure, the anatomical structure having a first side and a second side, the method including the steps of providing an end effector including an anvil that includes a first end, a second end, and an anvil face; a cartridge retaining a plurality of staples, the cartridge having a first end, a second end, and a cartridge face, the cartridge face including a channel extending from the first end of the cartridge to the second end of the cartridge, where the first end of the cartridge is pivotally coupled with the first end of the anvil; a blade, the blade having a cutting surface, first and second electrodes coupled to a first side of the blade and third and fourth electrodes coupled to a second side of the blade, and at least one elongated arm, at least one tissue sensor coupled to the blade, where the at least one elongated arm is slidably engaged with the channel; inserting the end effector through a trocar to access the anatomical structure; positioning the cartridge face on the first side of the anatomical structure; positioning the anvil face on the second side of the anatomical structure; clamping the end effector on the anatomical structure; operating the end effector to urge the plurality of staples from the cartridge to staple the anatomical structure; actuating the blade to cut the anatomical structure; applying bipolar energy to the anatomical structure via circuitry comprising the first, second, third, and fourth electrodes; and monitoring a temperature of the anatomical structure via the at least one tissue sensor.

Certain embodiments of the disclosed technology provide a method of stapling, resecting, and sealing an anatomical structure of a patient during a minimally invasive procedure, the anatomical structure having a first side and a second side, the method including the steps of providing an end effector including an anvil that includes a first end, a second end, and an anvil face; a cartridge retaining a plurality of staples, the cartridge having a first end, a second end, and a cartridge face, the cartridge face including a channel extending from the first end of the cartridge to the second end of the cartridge, where the first end of the cartridge is pivotally coupled with the first end of the anvil; a blade, the blade having a cutting surface, at least one resistive heating element coupled to the blade, and at least one elongated arm, where the at least one elongated arm is slidably engaged with the channel; inserting the end effector through a trocar to access the anatomical structure; positioning the cartridge face on the first side of the anatomical structure; positioning the anvil face on the second side of the anatomical structure; clamping the end effector on the anatomical structure; operating the end effector to urge the plurality of staples from the cartridge to staple the anatomical structure; actuating the blade to cut the anatomical structure; applying energy to the anatomical structure via circuitry comprising the at least one resistive heating element to heat the anatomical structure.

Certain embodiments of the disclosed technology provide a method of stapling, resecting, and sealing an anatomical structure of a patient during a minimally invasive procedure, the anatomical structure having a first side and a second side, the method including the steps of providing an end effector including an anvil that includes a first end, a second end, and an anvil face; a cartridge retaining a plurality of staples, the cartridge having a first end, a second end, and a cartridge face, the cartridge face including a channel extending from the first end of the cartridge to the second end of the cartridge, where the first end of the cartridge is pivotally coupled with the first end of the anvil; a blade, the blade having a cutting surface, one electrode coupled to the blade, a tissue sensor coupled to the blade, and at least one elongated arm, where the at least one elongated arm is slidably engaged with the channel; inserting the end effector through a trocar to access the anatomical structure; positioning the cartridge face on the first side of the anatomical structure; positioning the anvil face on the second side of the anatomical structure; clamping the end effector on the anatomical structure; operating the end effector to urge the plurality of staples from the cartridge to staple the anatomical structure; actuating the blade to cut the anatomical structure; applying monopolar energy to the anatomical structure via circuitry comprising the one electrode and a return electrode attached to the patient; and monitoring a temperature of the anatomical structure via the tissue sensor.

Certain embodiments of the disclosed technology provide a surgical instrument to staple, resect, and seal an anatomical structure of a patient, the surgical instrument including an end effector, the end effector including an anvil that includes a first end, a second end, and an anvil face positionable on the first side of the anatomical structure; a cartridge operably configured to house a plurality of staples, the cartridge comprising a first end, a second end, and a cartridge face positionable on the second side of the anatomical structure, the cartridge face including a channel extending from the first end of the cartridge to the second end of the cartridge, where the first end of the cartridge is pivotally coupled with the first end of the anvil; a blade, the blade having a cutting surface and at least one elongated arm, where the at least one elongated arm is slidably engaged with the channel; an active electrode coupled to a first side of the blade and a return electrode coupled to the first side of the blade proximate to the active electrode; a tissue sensor coupled to the blade; an elongate tube, the elongate tube having a proximal end and a distal end, where the distal end is coupled with the end effector; a handle, the handle having a proximal end and a distal end, where the distal end of the handle is coupled with the proximal end of the elongate tube; a drive assembly having a motor to actuate the end effector; circuitry extending through the elongate tube to the active electrode and the return electrode, where the circuitry connects the active and passive electrodes to an electrosurgical energy source, such as a bipolar energy source.

Certain embodiments of the disclosed technology provide a method of stapling an anatomical structure of a patient during a minimally invasive procedure, the anatomical structure having a first side and a second side, the method including the steps of providing an end effector including a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, where the second coupling includes a rigid link; and an I-shaped blade, the I-shaped blade including a blade portion having a cutting edge, a first side, and a second side, at least one upper lateral arm, a first electrode coupled to the first side of the blade and a second electrode coupled to the first side of the blade, a tissue sensor coupled to the blade, where the at least one upper lateral arm is slidably positioned in the first channel, and at least one lower lateral arm, where the at least one lower lateral arm is slidably positioned in the second channel; inserting the end effector through a trocar to access the anatomical structure; positioning the cartridge face on the first side of the anatomical structure; positioning the anvil face on the second side of the anatomical structure; operating the end effector to move the rigid link such that the anvil is urged towards the cartridge to clamp the end effector on the anatomical structure; operating the end effector to urge the plurality of staples from the cartridge to staple the anatomical structure; actuating the I-shaped blade to cut the anatomical structure, and activating an electrosurgical circuit to seal the anatomical structure at the cut using the first and second electrodes.

Certain embodiments of the disclosed technology provide a surgical instrument to staple, resect, and seal an anatomical structure of a patient, the surgical instrument including an end effector, the end effector including a first jaw having a first end, a second end, an anvil having an anvil face, and a first channel; a second jaw having a first end, a second end, a cartridge having a cartridge face, and a second channel; a first coupling that couples the first end of the first jaw to the first end of the second jaw; a second coupling that movably couples the second end of the first jaw to the second end of the second jaw, where the second coupling includes a rigid link; and an I-shaped blade, the I-shaped blade including a blade portion having a cutting edge, a first side, and a second side, at least one upper lateral arm, a first electrode coupled to the first side of the blade and a second electrode coupled to the first side of the blade, a tissue sensor coupled to the first side of the blade, where the at least one upper lateral arm is slidably positioned in the first channel, and at least one lower lateral arm, where the at least one lower lateral arm is slidably positioned in the second channel; and an elongate tube, the elongate tube having a proximal end and a distal end, where the distal end is coupled with the end effector; a handle, the handle having a proximal end and a distal end, where the distal end of the handle is coupled with the proximal end of the elongate tube, where the handle defines a cavity and a spool is positioned internal to the cavity; circuitry connecting the first and second electrodes to an electrosurgical energy source, and a drive assembly having a motor to actuate the end effector, and where at least part of the circuitry is wound around the spool during actuation of the end effector.

Certain embodiments of the disclosed technology provide a surgical instrument for use by a surgeon to staple and effect hemostasis on an anatomical structure of a patient during a minimally invasive procedure, the end effector including an anvil that includes a first end, a second end, and an anvil face positionable on the first side of the anatomical structure, a cartridge operably configured to house a plurality of staples, the cartridge comprising a first end, a second end, and a cartridge face positionable on the second side of the anatomical structure, the cartridge face defining a channel extending from the first end of the cartridge to the second end of the cartridge, wherein the first end of the cartridge is pivotally coupled with the first end of the anvil; a blade assembly comprising a blade, a beam, and a nut, the blade comprising a first side and a second side joined at a cutting edge, wherein at least a portion of the blade assembly is slidably engaged with the channel; and first and second electrodes coupled to the first side of the blade. A tissue sensor coupled to the first side of the blade. The surgical instrument includes an elongate tube, the elongate tube having a proximal end and a distal end, wherein the distal end is coupled with the end effector; a handle, the handle having a proximal end and a distal end, wherein the distal end of the handle is coupled with the proximal end of the elongate tube; a drive assembly comprising a motor to actuate the end effector; and an electrosurgical power generating source, the electrosurgical power generating source in electrical communication with the first and second electrodes.

Certain embodiments of the disclosed technology provide an end effector for use by a surgeon to staple and resect an anatomical structure of a patient during a minimally invasive procedure, the anatomical structure having a first side and a second side, the end effector comprising an anvil that includes a first end, a second end, and a face that is positionable on the first side of the anatomical structure. The end effector further comprises a cartridge that is configured to house a plurality of staples and that includes a first end, a second end, and a face that is positionable on the second side of the anatomical structure, and a blade assembly comprising a first side, a second side, and a cutting edge. The end effector further comprises first and second electrodes and a tissue sensor coupled to the first side of the blade assembly, and a recess defined by the anvil, the recess receiving a first portion of the blade assembly the housing. The end effector further comprises a first slot defined by the anvil that is open to the anvil face and to the recess and that is configured to slidably receive a second portion of the blade assembly during cutting of the anatomical structure with the cutting edge, and a second slot defined by the cartridge that is open to the cartridge face and that is configured to slidably receive a third portion of the blade assembly during cutting of the anatomical structure with the cutting edge. The second end of the anvil is movably coupled to the second end of the cartridge, each of the anvil and the cartridge is insertable through a trocar and the end effector is remotely operable from outside the patient with at least a portion of one of the anvil and the cartridge being movable toward the other to clamp the end effector to the anatomical structure.

Certain embodiments of the disclosed technology provide a method of stapling and sealing an anatomical structure of a patient during a minimally invasive procedure wherein the anatomical structure has a first side and a second side. The method may include the steps of: providing a stapler with an end effector having a plurality of electrodes and a tissue sensor positioned proximate to a cutting edge, a first jaw having a first end, a second end and an anvil having an anvil face; a second jaw having a first end, a second end and a cartridge housing a plurality of staples, the cartridge having a cartridge face; a first coupling that couples the first jaw to the second jaw; and a second coupling that movably couples the second end of the first jaw to the second end of the second jaw, wherein the second coupling includes a link that is movably coupled to the first and second jaws; inserting the end effector through a trocar to access the anatomical structure; positioning the cartridge face on the first side of the anatomical structure; positioning the anvil face on the second side of the anatomical structure; remotely operating the stapler from outside the patient to move the link such that at least a portion of one of the anvil or the cartridge is moved toward the other to clamp the end effector on the anatomical structure; firing the stapler and activating the electrodes to simultaneously staple, cut, and seal the anatomical structure; monitoring a tissue temperature via the tissue sensor.

Certain embodiments of the disclosed technology provide a method of stapling an anatomical structure of a patient during a minimally invasive procedure, wherein the anatomical structure has a first side and a second side. The method includes the steps of: providing an anvil that includes a first end, a second end, and a face; positioning the anvil face on the first side of an anatomical structure; providing a cartridge housing a plurality of staples, the cartridge including a first end, a second end, and a face, the face including a channel extending from the second end to the first end, wherein the second end of the anvil is movably coupled to the second end of the cartridge; positioning the cartridge face on the second side of the anatomical structure; providing a blade having a cutting surface and an elongated arm, the elongated arm extending at least from the blade positionable near the second end of the cartridge to the first end of the cartridge, the arm slidably engaged with the cartridge channel; providing an active electrode and a passive electrode positioned on one side of the blade; providing a tissue sensor on one side of the blade; providing a rigid link that movably couples the first end of the anvil to the first end of the cartridge; moving the rigid link causing at least a portion of one of the anvil and the cartridge to move toward the other to clamp the anatomical structure between the anvil face and the cartridge face; and pulling the blade through the anatomical structure, activating the electrodes, and simultaneously cutting, stapling, sealing, and monitoring a temperature of the anatomical structure.

It should be appreciated that all combinations of the foregoing concepts and additional concepts discussed in greater detail below (provided such concepts are not mutually inconsistent) are contemplated as being part of the technology disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the descriptions provided herein are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed technology and, together with the general description given above and detailed description given below, serve to explain the principles of the disclosed subject matter, and wherein.

DETAILED DESCRIPTION

Figure 1:
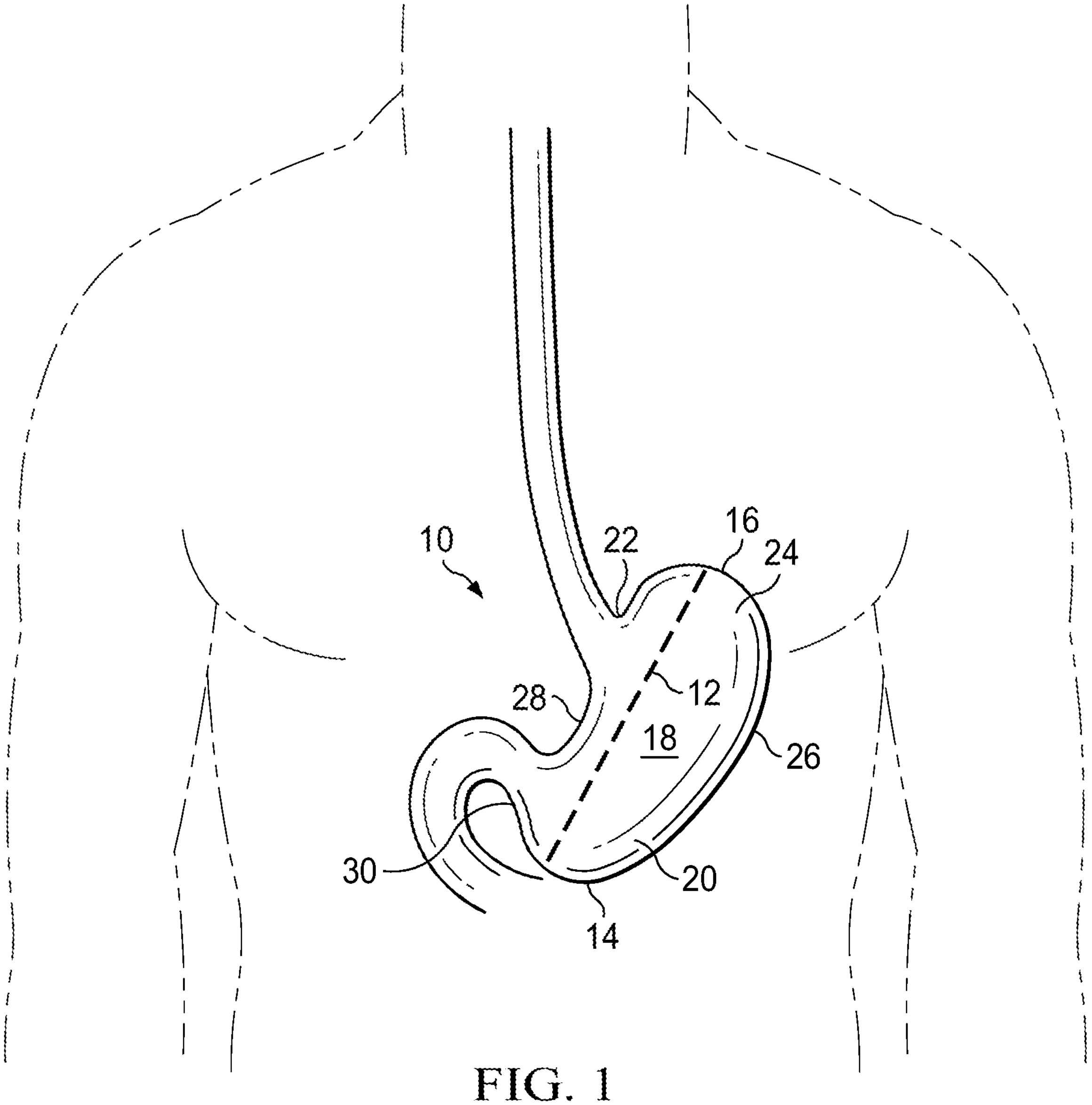
FIG. 1 depicts the anatomy of a stomach.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure. Reference throughout the specification to "various embodiments," "certain embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments. Described herein are example embodiments of apparatuses, systems, and methods for surgical instruments and tools, such as electrosurgical staplers. In one example embodiment, an end effector and/or an endocutter stapling device (collectively referred to as "devices" herein) is disclosed for forming a resection line during resection of an organ, tissue, or other anatomical structure. In some embodiments, the devices may be used during minimally invasive surgical procedures. This application is related to U.S. Pat. No. 9,936,953, which is hereby incorporated herein by reference in its entirety.

Electrosurgical instruments described herein, including, but not limited to electrosurgical staplers, can involve the application of electrical energy and/or electromagnetic energy to cut, dissect, ablate, coagulate, cauterize, seal or otherwise treat biological tissue during a surgical procedure. Electrosurgery is typically performed using an electrosurgical generator operable to output energy and a handpiece including an end effector adapted to transmit energy to a tissue site during electrosurgical procedures. Embodiments of the devices can be bipolar instruments, having two electrodes of opposite polarity that are located in proximity to one another for the application of current between their surfaces. Bipolar electrosurgical current travels from one electrode (sometimes referred to as the active electrode), through the intervening tissue to the other electrode (sometimes referred to as the return electrode) to complete the electrical circuit.

One of the issues that can arise from electrosurgical procedures is undesirable tissue damage due to thermal effects, wherein otherwise healthy tissue surrounding the tissue to which the electrosurgical energy is being applied is thermally damaged by an effect known in the art as "thermal spread". During the occurrence of thermal spread excess heat from the operative site can be directly conducted to the adjacent tissue, and/or the release of steam from the tissue being treated at the operative site can result in damage to the surrounding tissue. In accordance with the present disclosure, one or more sensors can be configured to supply a feedback signal indicative of a property of the tissue, such as the temperature or impedance of the tissue. Such feedback signal can be collected in real-time while energy is supplied to the tissue through the one or more electrodes. The one or more sensors can be positioned in close proximity to the electrodes and translate through the tissue as it is being resected thereby providing signaling along the resection site.

Electrosurgical staplers in accordance with embodiments described herein can include a handle, an actuator, and an end effector including a clamping mechanism. The clamping mechanism can include a cartridge and an anvil. During operation, the surgeon can clamp two members (e.g., the anvil and the cartridge) on the organ and compress the organ therebetween. Once the organ has been compressed, the surgeon can use the stapler to drive or fire staples through the organ. In one embodiment, with desirable compression and alignment of the clamping mechanism, a plurality of B-shaped staples can be formed. In some embodiments, the stapling device can be fired multiple times using multiple cartridges, or in an alternate embodiment a single cartridge can be used with a single firing to complete resection of an organ. It may be advantageous to reduce the number of firings and cartridges required as the expense of a procedure can increase with the use of cartridges and with a longer procedure that can be associated with multiple stapler firings. It may also be advantageous to provide for single cartridge stapling and/or resection of an organ to reduce the time a patient is in surgery, which can improve clinical outcomes. For example, resecting a portion of the stomach in accordance with a sleeve gastrectomy procedure using a single cartridge and stapler firing may improve patient outcomes and reduce complications that can be associated with such procedures.

The integrity of a staple line can depend, in part, on the proper formation of B-shaped staples when such a staple configuration is desirable. Providing a single cartridge and single firing stapling device may improve the quality of staple formation over a device or system using multiple cartridges to complete the same procedure. For example, when using an end effector multiple times to staple and resect tissue the previously deployed staples may be contacted by the new staples and/or cutting knife in subsequent applications. Providing a single cartridge and staple firing may help ensure that the staple line, and shape of the staples, is consistent.

A single cartridge and single firing stapling device may also provide compression benefits relative to a device and system requiring the use of multiple cartridges. It may be advantageous to provide a single firing stapling device that provide for desirable compression along the length of the tissue to be resected while also providing for a single staple line with properly formed staples. A B-shaped staple is the standard of care for gastrointestinal, vascular, pulmonary, and hepatic applications of surgical tissue fastening devices. Alignment in each of the X, Y, and Z axes of the clamping mechanism with itself (e.g., alignment of the anvil with the cartridge) on each side of the organ may improve staple delivery and formation. It will be appreciated that any suitable structure, staple form, staple shape, staple format or other suitable mechanism may be incorporated into the stapling devices described herein to provide for such alignment.

Embodiments of electrosurgical stapling devices can include an anvil and a cartridge, where the cartridge can include recesses retaining a plurality of staples. The staples can be retained above one or more staple drivers that, during operation, can urge each of the plurality of staples upward through tissue into the face of the anvil. The anvil, which can include pockets having any suitable size, number, and dimensions, can cooperate with the cartridge drivers to form, for example, a B-shape within tissue. The pockets of the anvil, in one embodiment, can be sized to provide a desirable closed staple height that can be determined by the gap between the anvil and cartridge, the depth of the pocket and the height of the staple, and/or the staple driver and the driver mechanism.

Embodiments of electrosurgical stapling devices can include electrodes and a tissue sensor that are positioned proximate to a cutting edge of blade assembly. In some embodiments, the tissue sensor and electrodes are positioned on only a single side of the blade assembly. Such electrodes and tissue sensor can be configured and positioned such that they come in direct contact with tissue that has been cut by the cutting edge. One of the electrodes can be an active electrode, which delivers energy through the tissue to the other electrode, which can be a return electrode. The delivery of such energy can affect hemostasis by heating the tissue and blood vessels to cauterize, coagulate/desiccate, and/or seal tissue. The tissue sensor can move along the resection site in close proximity to the electrodes to provide feedback regarding the tissue status as it is being cut.

Embodiments of electrosurgical stapling devices described herein, in accordance with a laparoscopic approach, can include inserting the end effector of the stapler through a trocar to perform the surgical procedure. By way of example, minimally invasive surgical procedures may include a laparoscopic vertical sleeve gastrectomy. Because the spatial environment for such procedures is limited, surgical stapling devices in accordance with embodiments described herein may have a relative low profile. Minimally invasive devices in the prior art are generally long (e.g., 35 mm to 60 mm) and thin (e.g., 5 mm to 15 mm diameter) devices. This long and thin configuration may be necessary to fit through the trocar into the body cavity. The limited size can present a mechanical issue as B-shaped staple formation typically requires a pressure of about 100 psi. Under these pressures, small, less rigid, staplers may deform and thus prevent proper B-shaped staple formation.

Prior art devices used in minimally invasive surgical procedures often have a fixed hinge at a proximal end. This hinge allows the anvil and cartridge to separate into a V-shaped configuration. Once separated, the surgeon may place the open anvil and cartridge around the organ and then collapse the V onto the organ. However, as the length of the anvil and cartridge increase, it may be more difficult to maintain alignment between the anvil and cartridge across the length of the tissue. Poor alignment with such designs can be exacerbated at the most distant ends of such devices can be deflected because of the forces necessary to compress the tissue. Because of this deflection, the length of current V-shaped staplers for minimally invasive procedures is limited. As a result of this limitation, the anvil and the cartridge are correspondingly limited in length. This limitation on length requires, for larger organs like the stomach, multiple staple reloads and firings to complete a procedure such as a sleeve gastrectomy. Each reload may require the surgeon to withdraw the stapler from the trocar, reload the cartridge, reinsert, and then reposition the stapler on the organ. Such systems may require more surgical time, may be more costly, may have an increased likelihood of resulting in an adverse patient event, and may result in a staple line having less integrity.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example embodiments described herein can be used, for example, in a sleeve gastrectomy procedure or resection of the stomach. It will be appreciated, however, that the devices may be used in other procedures involving other anatomical structures. For example, the devices may be used in a parenchymal resection, lung volume reduction surgery, or other procedures involving the lung. Further, embodiments described herein may be useful in an anatomic resection, such as, a lobectomy, a non-anatomic parenchymal resection, or other procedures involving the liver, or in a partial nephrectomy, total nephrectomy, or other procedures involving the kidney.

Referring now to FIG. 1, shown are the anatomy of the stomach 10 and an example resection line 12 for a vertical sleeve gastrectomy. The stomach 10 generally includes an inferior end 14, a superior end 16, an anterior side 18, and a posterior side 20. A gastroesophageal junction 22 opens into the stomach 10 and is a common landmark in bariatric surgeries. A fundus 24 and the section of the stomach 10 defined by a greater curvature 26 are generally the parts of the stomach 10 removed during a vertical sleeve gastrectomy. The remaining pouch or sleeve may be generally defined by a lesser curvature 28 and the resection line 12, which presents a stomach with a significantly reduced volume. The desired location of the resection line 12 may be about 0.5 cm to about 2 cm away from the gastroesophageal junction 22 and about 2 cm to about 10 cm away from a pylorus 30. In accordance with embodiments described herein, endocutter stapling devices may be utilized to form high quality, consistent resection lines during a vertical sleeve gastrectomy. Embodiments of the devices may be advantageous because they may be easily positionable laparoscopically, can accommodate different thicknesses of tissue along the resection line length, can be capable of providing uniform compressive pressure on the tissue along the resection line, and can enable a low staple firing force. Embodiments of the devices may utilize electrical energy to cut, dissect, ablate, coagulate, cauterize, seal or otherwise treat the resection line during a surgical procedure.

Figure 2:
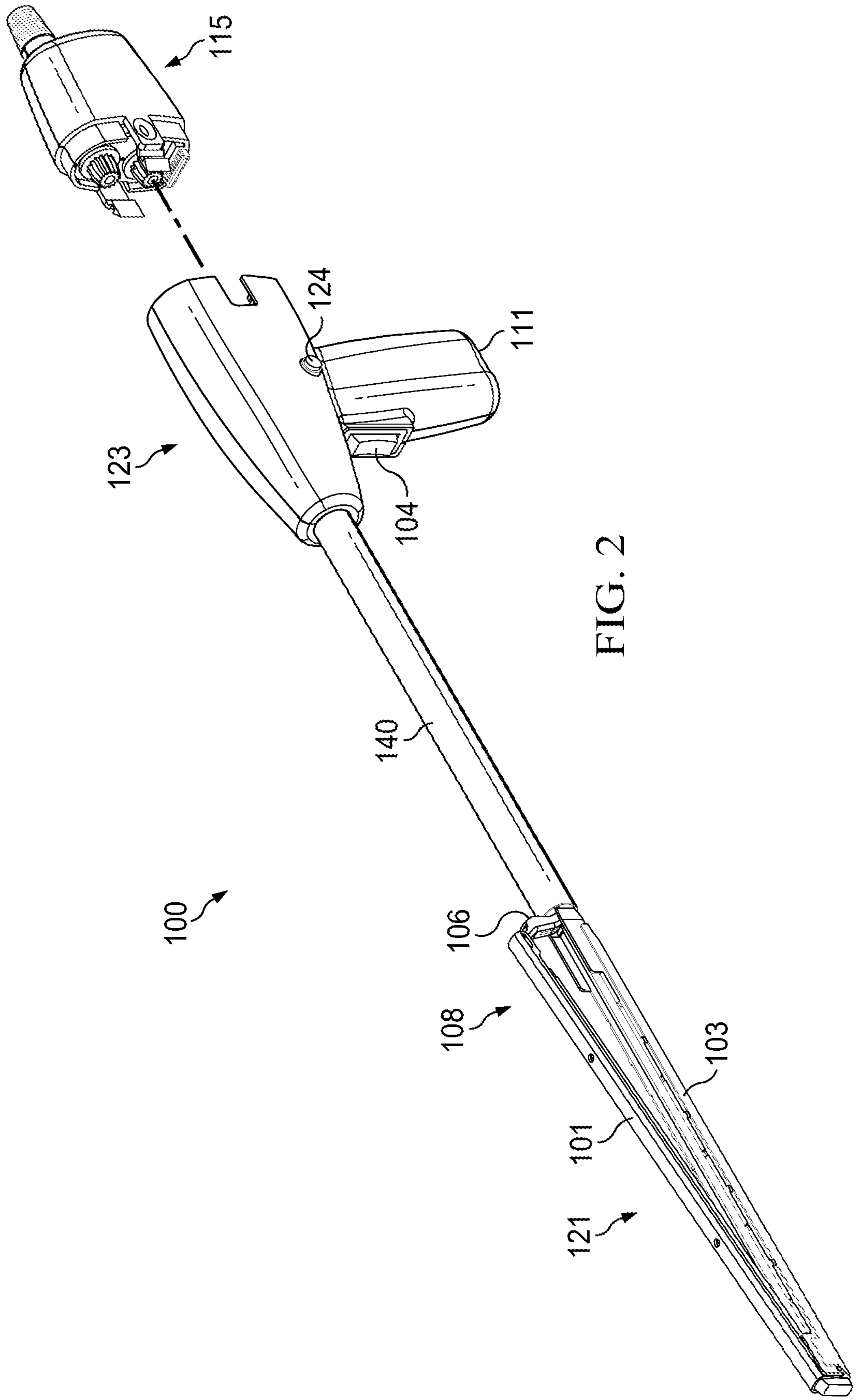
FIG. 2 depicts a perspective view of an electrosurgical stapling device, shown in an open position, having an end effector, an elongated tube, a handle portion, and a motor in accordance with an example embodiment.

FIG. 2 is a perspective view of an example electrosurgical stapling device 100 in accordance with one embodiment. The electrosurgical stapling device 100 can include an endocutter 108 and a motor assembly 115. The electrosurgical stapling device 100 comprising an end effector 121 including an anvil assembly 101 and a cartridge assembly 103, a support tube 140 and a handle portion 123. The anvil assembly 101 can function as a first jaw of the end effector 121 and the cartridge assembly can function as a second jaw of the end effector 121. The end effector 121 can be connected to the handle portion 123 via a support tube 140. The handle portion 123 can include a handle 111 and a trigger 104 for actuating the electrosurgical stapling device 100.

The handle portion 123 can include a mode button 124 for switching between operational modes. For example, in a first mode, the trigger 104 can be pressed upwards to open the jaws (e.g., the anvil and cartridge) or pressed downward to close the jaws. When the jaws are in a closed position, the mode button 124 can be depressed to transition the electrosurgical stapling device 100 into a firing mode. When in the firing mode, depressing the trigger 104 can fire the electrosurgical stapling device 100 to simultaneously form a staple line comprising of one or a plurality of rows of staples while cutting tissue. In one embodiment, depressing the trigger 104 in the firing mode can deploy a staple line including six rows of staples, where a knife (not shown) can simultaneously cut tissue between a third and a forth row of the staples. Immediately subsequent to being cut, electrical energy can be applied to the tissue via electrodes 170 (FIG. 3) that are positioned proximate to the knife, as described in more detail below.

Figure 3:
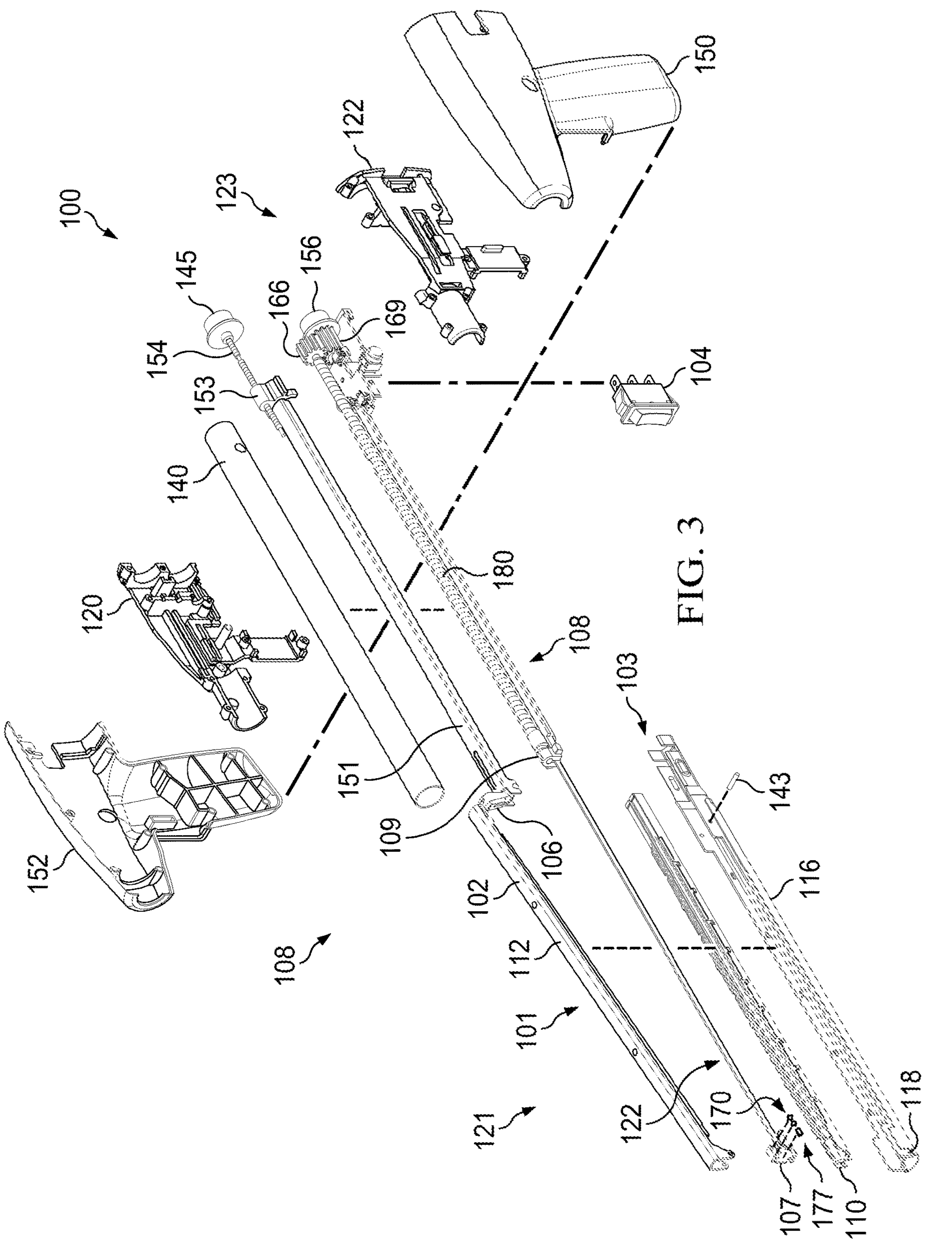
FIG. 3 is a partially exploded perspective view of the end effector, elongated tube, and handle portion of the electrosurgical stapling device shown in FIG. 2.

FIG. 3 depicts an exploded perspective view of electrosurgical stapling device 100 (FIG. 2) in accordance with at least one embodiment. The anvil assembly 101 can include an anvil frame 102 and an anvil plate 112. The anvil plate 112 can be welded to the anvil frame 102, or may be otherwise attached such as by gluing, brazing, sintering, machining, 3D printing or the like. A cartridge 110 containing a plurality of staples can be attached to the cartridge frame 116 by a first cartridge pin 143 at a first end and a second cartridge pin 118 at a second end, or alternately the cartridge 110 can be attached to the cartridge frame 116 via snap fit, gluing, or other attachment methods.

In the embodiment illustrated in FIG. 3, the cartridge frame 116 can be insertable at its proximal end into the support tube 140 to align and connect the end effector 121 of the endocutter 108 to the handle portion 123. A blade assembly can include a knife or blade 107 that can be coupled to a rotating member 180 via a nut 109, a bushing, or other suitable connection. The electrodes 170, which can be positioned on only one side of the knife, for example, can effect hemostasis by heating the tissue and blood vessels to cauterize, coagulate/desiccate, and/or seal tissue as the electrosurgical stapling device 100 is firing. The electrodes 170 can be in electrical communication with an electrosurgical power generating source via circuitry (not shown). A tissue sensor 177 can be positioned proximate to the knife 107. In some embodiments, the tissue sensor is coupled to the knife 107 and positioned distal to the electrodes 170. While a single tissue sensor 177 is shown in FIG. 3, this disclosure is not so limited, as any suitable number of tissue sensors 177 can be deployed in the end effector 121. The tissue sensor 177 can, for example, a resistance temperature device (RTD) that is employed as the temperature sensor. The RTD can be a component of a temperature measurement circuit that includes a current source to pass current through the RTD and a voltage reading means to read the voltage-drop produced across the RTD. From the current and voltage, a resistance value can be derived which is indicative of the temperature being sensed.

The handle portion 123 can include a right handle half 120 and a left handle half 122 that can be held together in a clamshell-like fashion. The right handle half 120 and left handle half 122 can be joined by, for example, ultrasonic welding, glue, screws, gripper pins or press-fit pins fit into holes molded into the handle, or other assembly methods. A left handle shell 150 and a right handle shell 152 can be used to provide a pleasing aesthetic look to the exterior of the handle portion 123 by covering the left handle half 122 and the right handle half 120.

Figure 4:
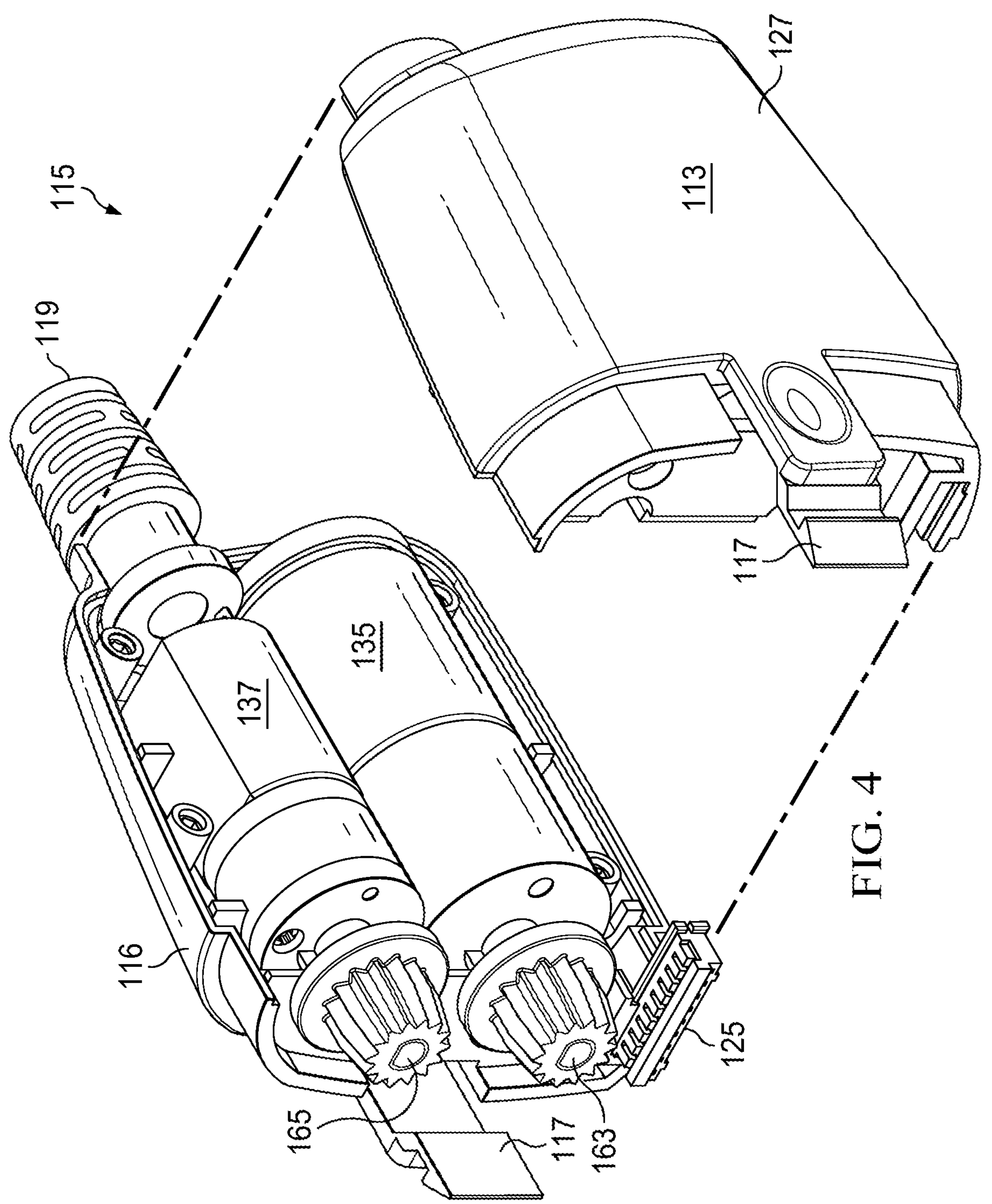
FIG. 4 is a partially exploded perspective view of the motor of the electrosurgical stapling device shown in FIG. 2.

A drive screw 154 can be used to drive a control arm 151 via a control arm nut 153. The drive screw 154 can be connected to a second drive gear coupler 145 that can engage the motor assembly 115 (FIG. 4). The rotating member 180 can be coupled to the motor assembly 115 via a firing drive gear 166 and a second firing drive gear 169, where the second firing drive gear 169 can engage the first drive gear coupler 156 that can be coupled with the motor assembly 115. In one embodiment, the second firing drive gear 169 and the first drive gear coupler 156 can be a single component or feature.

FIG. 4 is a perspective view of the motor assembly 115 in accordance with one embodiment. A first electric motor 135 and a second electric motor 137 can be provided in a motor housing 113. In one embodiment, the first motor gear 163 can be coupled with the first drive gear coupler 156 (FIG. 3) and a second motor gear 165 can be coupled with the second drive gear coupler 145 (FIG. 3). The motor housing 113 can include a left motor housing half 127 and a right motor housing half 116. The motor housing 113 can include snaps 117 to couple the motor assembly 115 with the handle portion 123 (FIG. 3). A strain relief 119 can be provided to support wiring to the motor assembly 115. A connector 125 can provide for electrically coupling the trigger 104 (FIG. 3) and other electrical components between the motor assembly 115 and the electrosurgical stapling device 100.

Figure 5A:
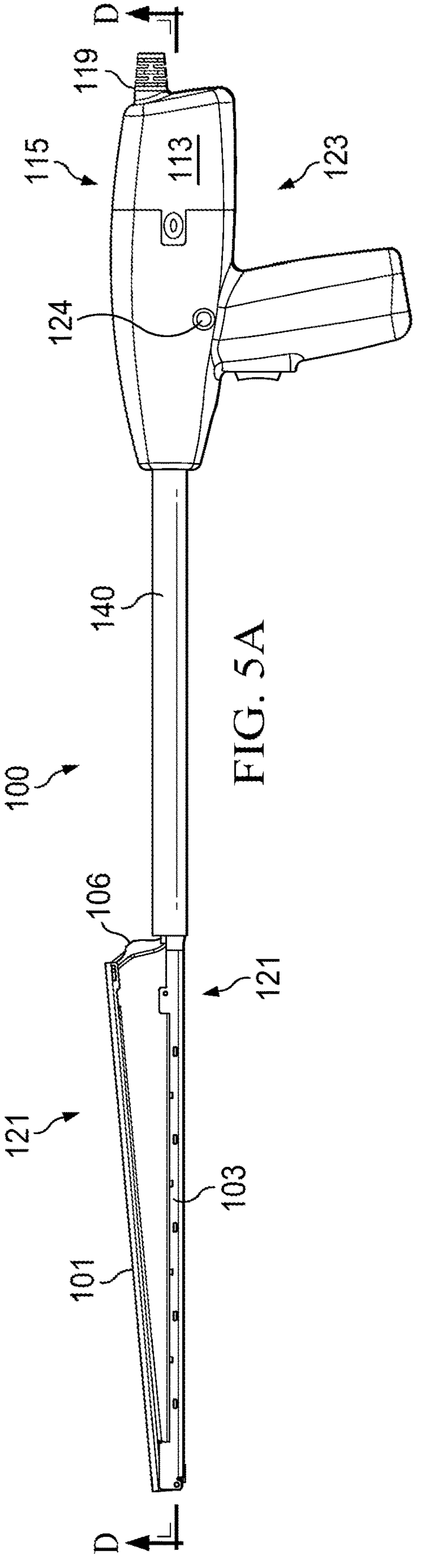
FIG. 5A depicts a side view of the electrosurgical stapling device of FIG. 2 shown in an open position.

FIG. 5A is a side view of the electrosurgical stapling device 100 in accordance with one embodiment showing the end effector 121 in an open position. The end effector 121 can include a first jaw comprising the anvil assembly 101 and a second jaw comprising the cartridge assembly 103. The end effector 121 can include a master link 106 operably coupled with the motor assembly 115.

Figure 5B:
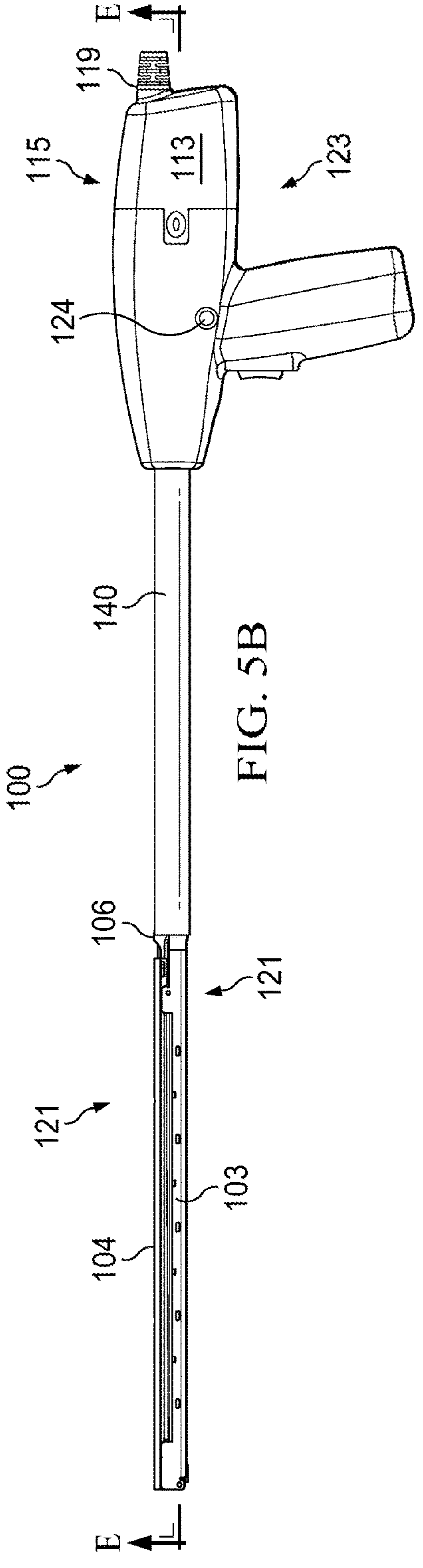
FIG. 5B depicts a side view of the stapling device of FIG. 2 shown in a closed position.

FIG. 5B is a side view of the electrosurgical stapling device 100 showing the end effector 121 in a closed position. The end effector 121, in its closed position, can be ready for firing, which can include deploying staples, cutting, and/or applied electrosurgical energy to tissue.

Figure 6:
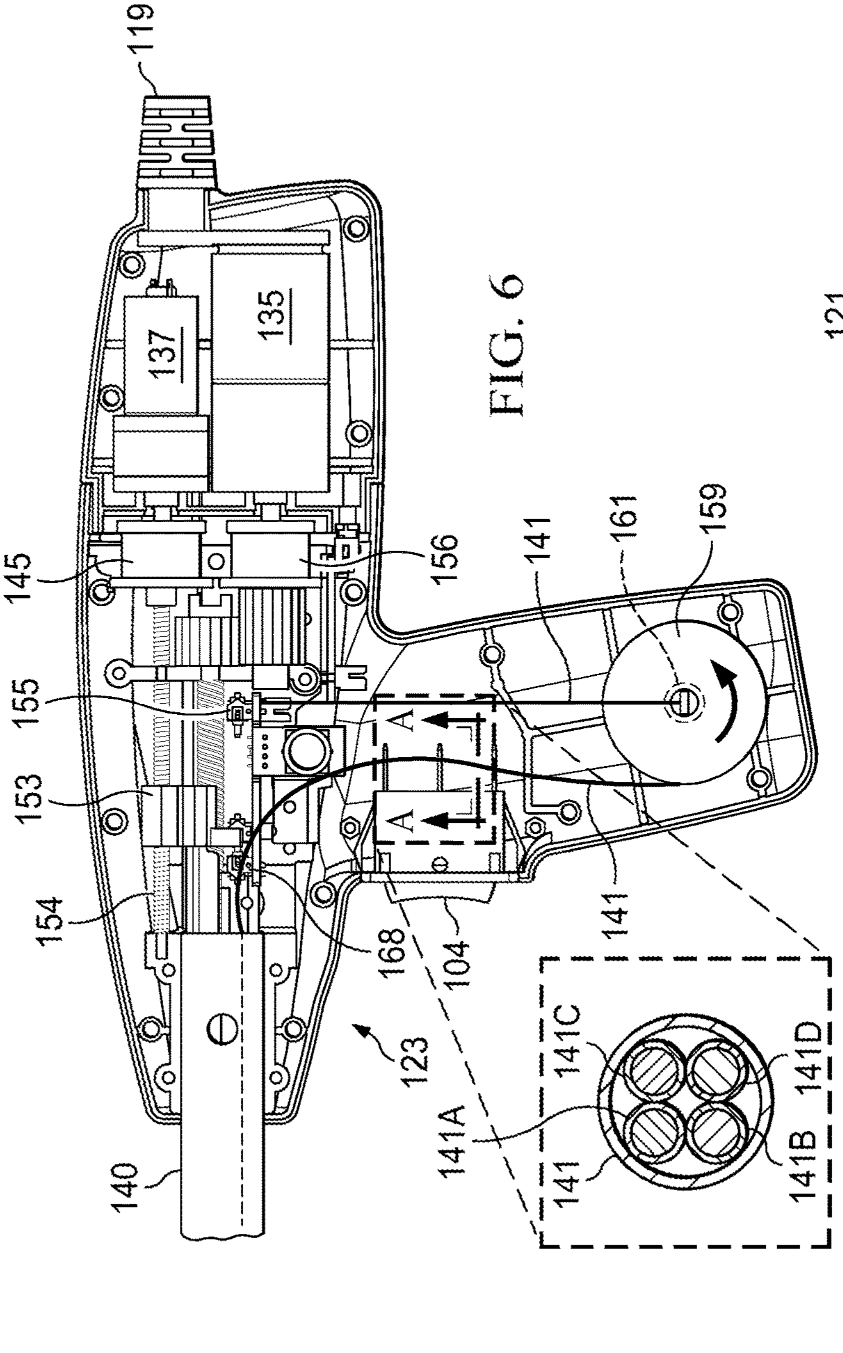
FIG. 6 depicts a side cross-sectional view, taken along section D-D, of the handle portion and the motor shown in FIG. 5A.

FIG. 6 depicts a cross-sectional side view of the handle portion 123 of the electrosurgical stapling device 100 in the open position (e.g., the position shown in FIG. 5A). A second drive gear coupler 145 for opening and closing the end effector 121 can be coupled to the second motor gear 165 (FIG. 4) associated with the second electric motor 137. The second drive gear coupler 145 can rotate the drive screw 154 to open and close the end effector 121 to transition the end effector 121 between an open position to a close position, and vice versa. In FIG. 6, the control arm nut 153 is shown in its distal-most position on the drive screw 154 such that the master link 106 is fully extended and the end effector 121 is in the open position. A control arm distal limit switch 168 can be contacted by the control arm nut 153 in the illustrated position, when the end effector 121 is in the fully open position, to interrupt power to the second electric motor 137. The first drive gear coupler 156 can be coupled to the second motor gear 165 to deploy staples from the electrosurgical stapling device 100 while simultaneously cutting and then sealing tissue via hemostasis.

FIG. 6 also schematically depicts conductors 141 that extend through the support tube 140 and are in electrical communication with the electrodes 170 (FIG. 3). In the illustrated embodiment, a spool 159 is positioned within a cavity defined by the handle portion 123. The conductors 141 can include, for example, conductors 141A-141D, as shown in Section A-A. For example, conductors 141A and 141B can be components of the circuit with the electrodes 170 and conductors 141C and 141D can be components of the circuit with the tissue sensor 177. The spool 159 can be configured to collect the slack from the conductors 141 as the electrodes 170 and tissue sensor 177 are proximally drawn toward the handle portion 123 during a surgical procedure. In some embodiments a constant force spring 161 can be coupled to the spool 159 to assist with automated winding of the spool 159 during operation.

Figure 7:
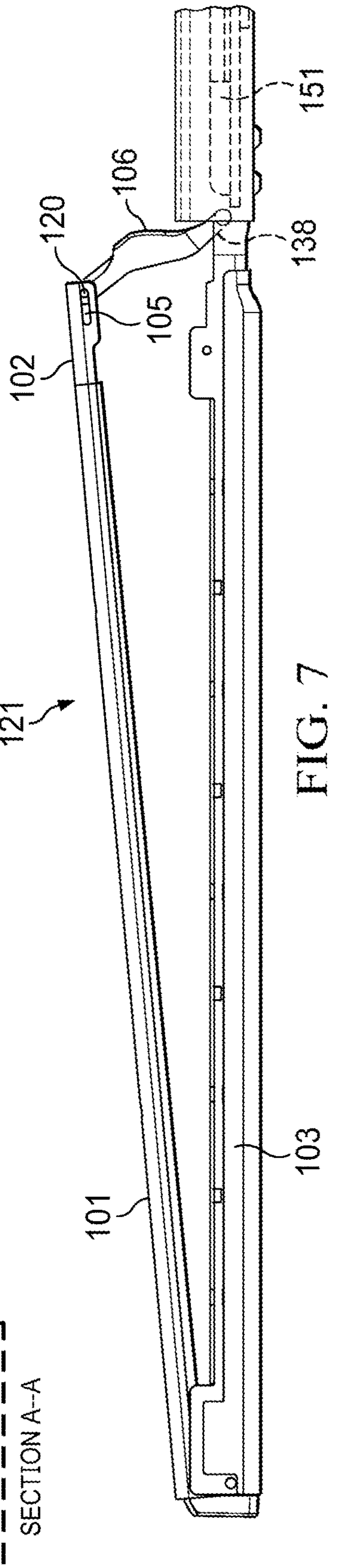
FIG. 7 depicts a side view of the end effector shown in FIG. 5A.

FIG. 7 depicts a side view of the end effector 121 of the electrosurgical stapling device 100 shown in the open position. The master link 106 can be attached to a first end of the anvil frame 102 by a first master link pin 120 such that the first master link pin 120 can pivotally and slidably engage master link slot 105. The master link slot 105 can be a channel parallel to the longitudinal axis of the anvil assembly 101, or the master link slot 105 can be angled up or down relative to this longitudinal axis. A second master link pin 138 can be used to pivotally couple the master link 106 to the control arm 151.

Figure 8:
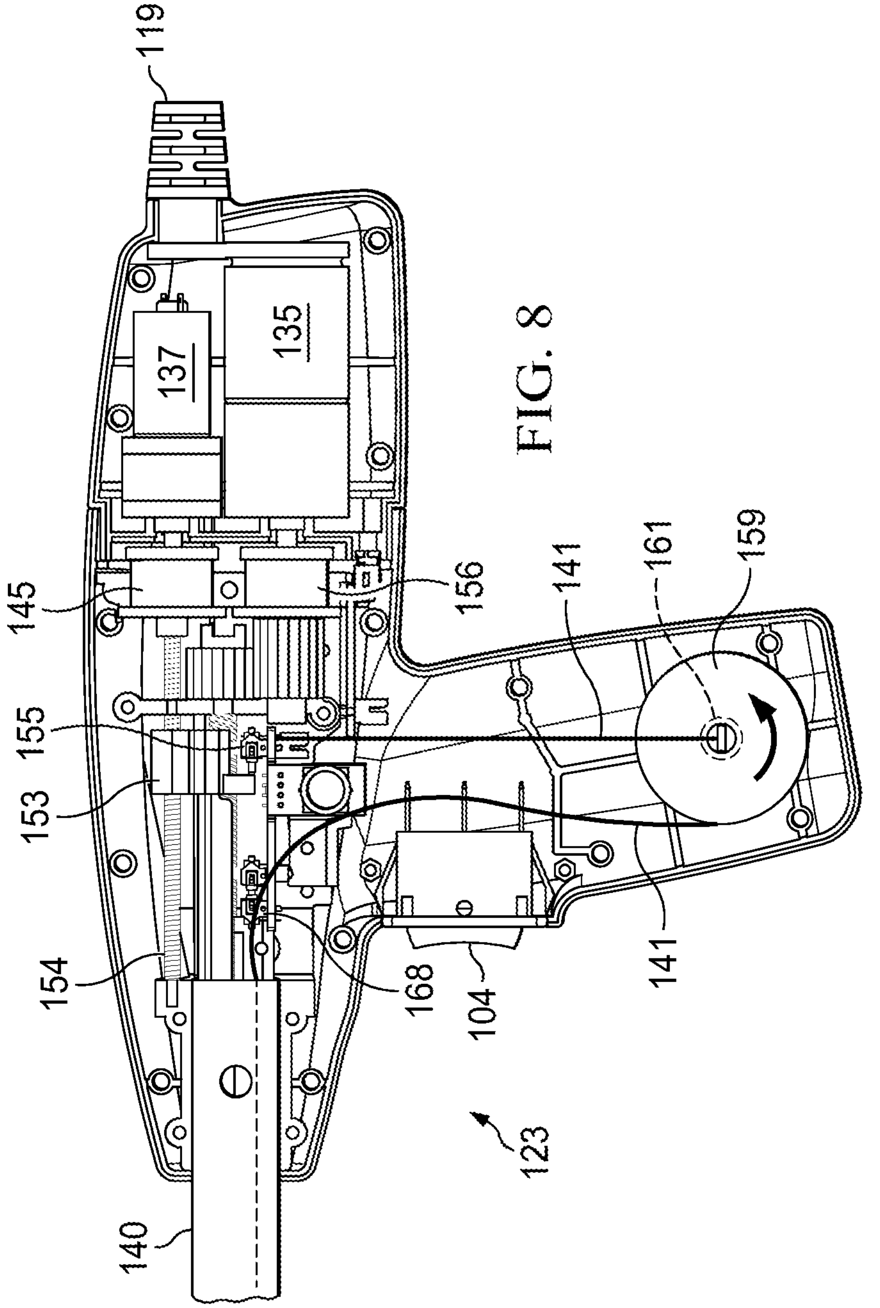
FIG. 8 depicts a side cross-sectional view, taken along section E-E, of the handle portion and the motor shown in FIG. 5B.

FIG. 8 depicts a cross-sectional side view of the handle portion 123 of the electrosurgical stapling device 100 shown in the closed position. The control arm nut 153 is illustrated in its proximal-most position on the drive screw 154 such that the anvil assembly 101 is closed relative to the cartridge assembly 103. In one embodiment, when the end effector 121 is closing, the control arm nut 153 can travel proximally until it contacts a proximal limit switch 155. When the control arm nut 153 contacts the proximal limit switch 155 it can interrupt power to the second electric motor 137. The electrosurgical stapling device 100 can be configured such that it cannot transition into a firing mode until the control arm nut 153 engages the proximal limit switch 155 to ensure that the electrosurgical stapling device 100 is in the closed position before firing.

Figure 9:
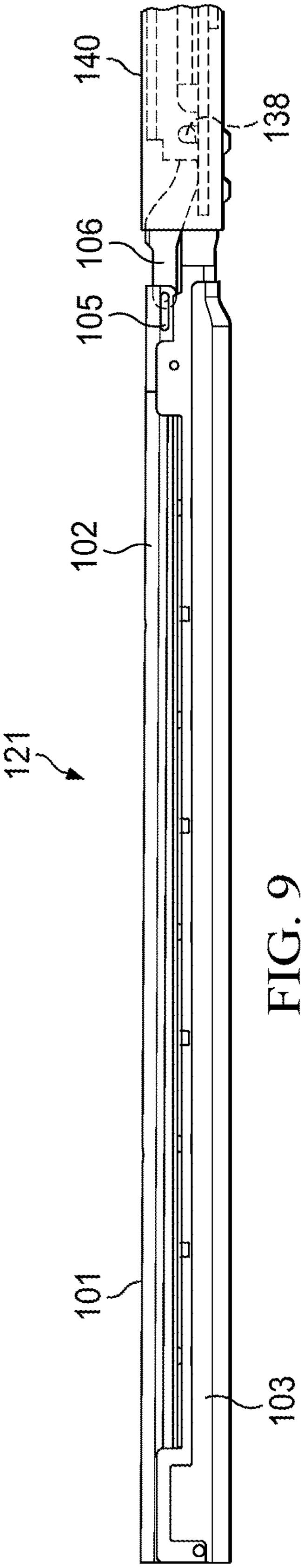
FIG. 9 depicts a side view of the end effector shown in FIG. 5B.

FIG. 9 depicts a side view of the end effector 121 of the electrosurgical stapling device 100 shown in the closed position. The master link 106 is illustrated as inserted partially into the support tube 140 such that the anvil assembly 101 and the cartridge assembly 103 are in a closed position ready for firing.

Figure 10:
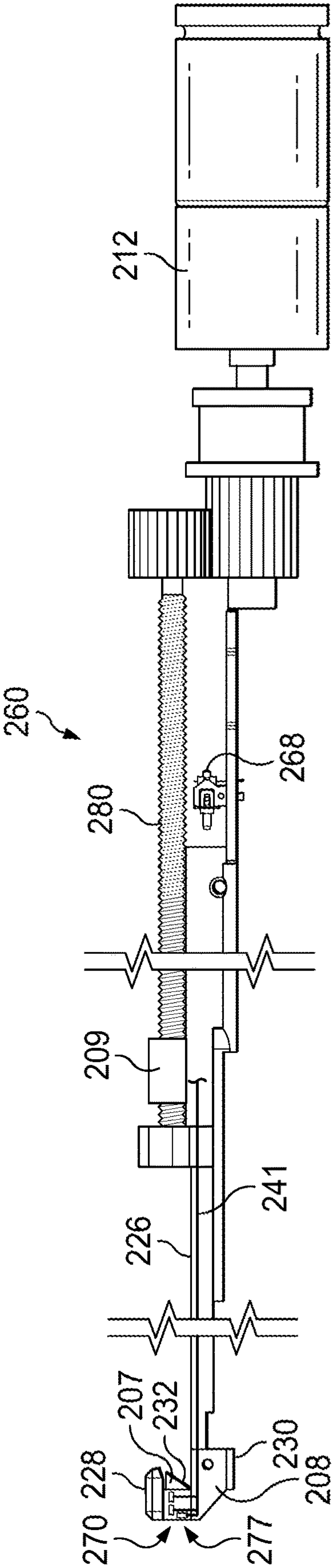
FIG. 10 is a sectioned side view of a blade assembly and a drive assembly for an electrosurgical stapling device according to one embodiment.

FIG. 10 is a side view of a drive assembly 260 for simultaneously stapling, cutting, and sealing tissue. The drive assembly 260 can include a blade assembly 208 including a blade 207 coupled to a beam 226. Electrodes 270 and a tissue sensor 277 can be positioned on one side of the blade 207 such that they directly contact the tissue that was cut by the blade 207. The electrodes 270 can be in electrical communication with an electrosurgical energy source via circuitry 241. The beam 226 can include a nut 209 that can threadedly engage a rotating member 280. The rotating member 280 can be operably coupled with the first electric motor 212 such that rotation of the rotating member 280 urges the nut 209 proximally. During operation, activating the first electric motor 212 can urge the nut 209 proximally such that the beam 226 and blade assembly 208 are correspondingly moved in a proximal direction. As the blade assembly 208 is urged proximally a cutting edge 232 on a blade 207 can transect tissue. Simultaneously, energy can be passed through the transected tissue via the electrodes 270 to heat the tissue and blood vessels to cauterize, coagulate/desiccate, and/or seal tissue along one side of the incision. The tissue sensor 277 can simultaneously provide real-time feedback regarding the status of the tissue proximate to the cutting site. The blade 207 can include a top portion 228 and a lower portion 230 that can compress an anvil and a cartridge of an end effector when urged proximally.

Still referring to FIG. 10, when the blade assembly 208 is pulled to its proximal-most position the nut 209 can engage a firing complete limit switch 268. When the nut 209 engages the firing complete limit switch 268 power to first electric motor 212 can be interrupted. It is contemplated that the nut 209 can be attached to the blade assembly 208 or beam 226 in any suitable fashion such as via a pin, a spot weld or other attachment method. Alternatively, the nut 209 can be formed monolithically as a unitary structure with the blade assembly 208 or the beam 226.

Figure 11:
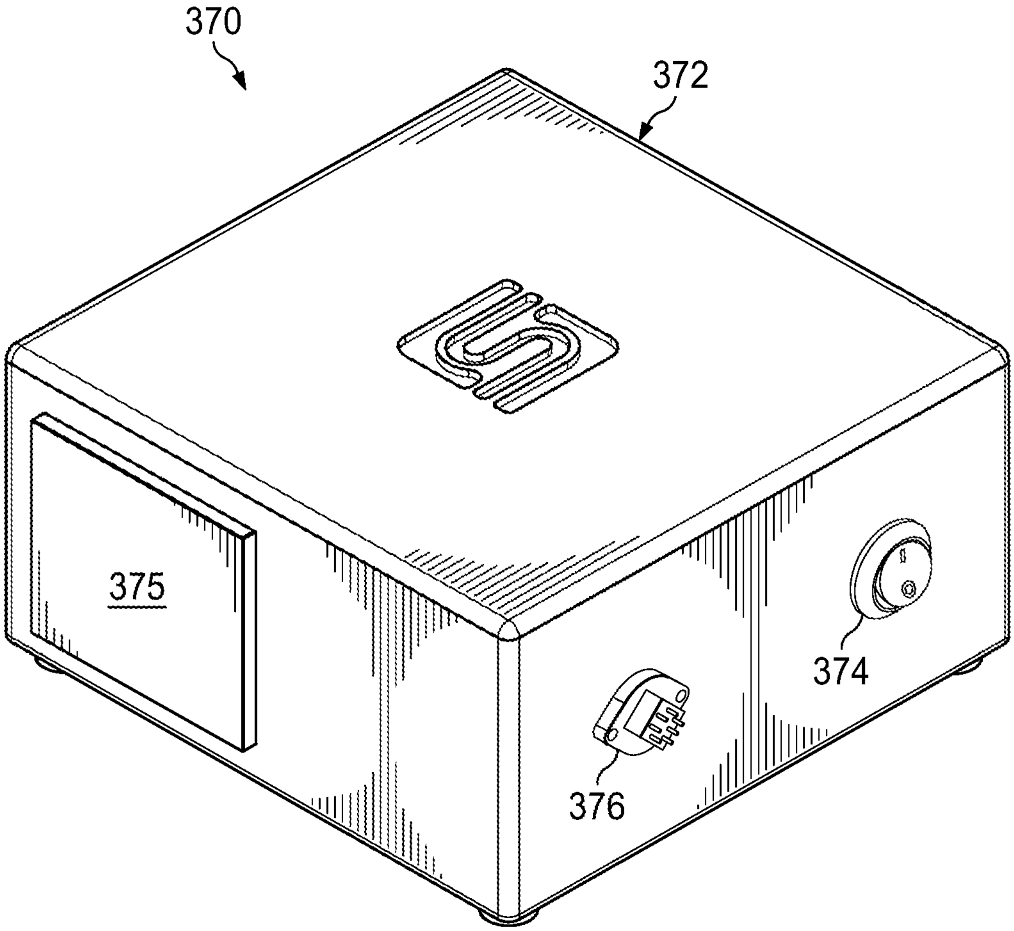
FIG. 11 is a perspective view of a motor controller according to one embodiment.

FIG. 11 is a perspective view of a motor controller 370 according to one embodiment. The motor controller 370 can include a controller housing 372 having an on/off switch 374, a display 375 and a device cable connector 376. The on/off switch 374 may provide for wall power, such as 110 Volt or 220 Volt AC power from a wall outlet, or may provide for battery power to the motor controller 370. The device cable connector 376 may connect multiple wires from the motor assembly of a stapling device to the motor controller 370. For example, the device cable connector 376 may provide positive and negative voltage wires to a first electric motor (e.g. first electric motor 135 shown in FIG. 4), positive and negative voltage wires to a second electric motor 137 (e.g., second electric motor 137 shown in FIG. 4), wires to a trigger (e.g., trigger 104 shown in FIG. 3), positive and negative sense wires to each of a firing complete limit switch 168 (FIG. 6), a wire in electrical communication with an active electrode and a wire in electrical communication with a return electrode (e.g., electrodes 170 (FIG. 3), electrodes 270 (FIG. 10)), wires in electrical communication with one or more tissue sensors (e.g. tissue sensor 177 (FIG. 3)) as well as any other wires useful for an endocutter.

Figure 12:
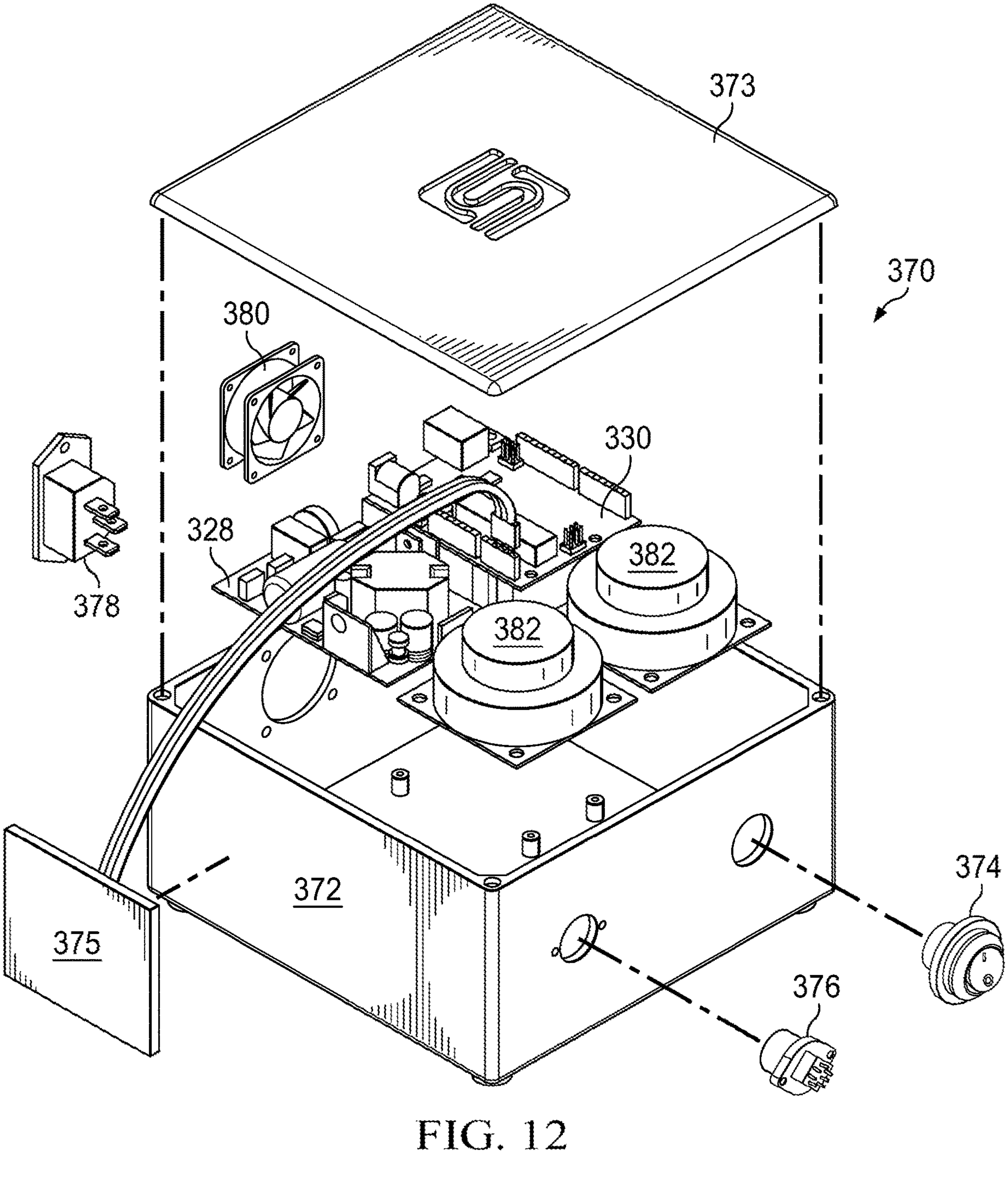
FIG. 12 is an exploded perspective view of the motor controller shown in FIG. 11.

FIG. 12 is an exploded perspective view of the motor controller 370 according to one embodiment. A lid 373, which can be part of the controller housing 372, can contain the components inside the controller housing 372. In the embodiment illustrated in FIG. 11, wall power can be brought into the controller housing 372 via an electrical inlet 378. A fan 380 may also be included to cool the interior of the controller housing 372. A pair of speakers 382 can be provided to inform the user of the stapling device conditions, such as, for example, jaws open, jaws closed, firing complete, ready to fire or other useful information. The display 375 can be used to provide visual directions, data, error conditions, instrument identification, or other useful data.

A motor controller board 328 can provide electrical power to the first electric motor 135 (FIG. 4) or the second electric motor 137 (FIG. 4) when appropriate. The motor controller board 328 can also control electrosurgical energy associated with various electrodes, such as electrodes 170 or electrodes 270 (FIG. 10). The motor controller board 328 can also receive signaling indicative of tissue status as provided by tissue sensor 177 or tissue sensor 277. The motor controller board 328 can be directed by a processor board 330 to turn on or off the first electric motor 135 or the second electric motor 137. The processor board 330 can contain a processor, such as an ARM processor or other processor, useful in controlling a stapling device. For example, the processor board 330 can contain software that reads the condition of the limit switches 155, 168 (FIG. 6) and the trigger 104 (FIG. 6) and can control the motor controller board 328 to, for example, open and close the jaws, fire the system, activate an electrosurgical energy source, or perform other useful functions.

In one example embodiment, the ARM processor can be used to communicate with an endocutter (for example, stapling device 100 shown in FIG. 1). For example, the electrosurgical stapling device 100 may include an EEPROM or other memory retaining device that can be encoded with a serial number during manufacturing. The memory can be used to provide information to the motor controller. For example, the processor can be capable of measuring and recording opening and closing motor amperage during activation on the manufacturing line; data regarding tissue condition along the resection site; firing motor amperage during activation on the manufacturing line; opening and closing motor amperage in clinical use; firing motor amperage during activation in clinical use, or other data useful to the manufacturer or operator. This data can also be relayed to the motor controller 370 and stored. Such information can also be displayed during firing to the user by way of a connection of the motor controller 370 to a screen or display that can be incorporated into the electrosurgical stapling device 100, in the motor controller 370, or the data may be transmittable to a monitor used by a laparoscopic camera in a minimally invasive procedure.

In one embodiment, an electrosurgical stapling device system in accordance with embodiments described herein may have a unique serial number or other identifier to allow the operator to record the particular serial number of the instrument used in a patient's record. When an instrument is plugged into the controller, such as motor controller 370, the controller may communicate with the memory and provide the serial number on a display of the controller. The memory may also be used to record information regarding the use of the instrument. For example, an event log may be recorded into the memory from the controller that records motor load, number of openings or closings of the instrument, number of firings of the instrument, error codes or other useful information onto the memory for later review.

Figure 13:
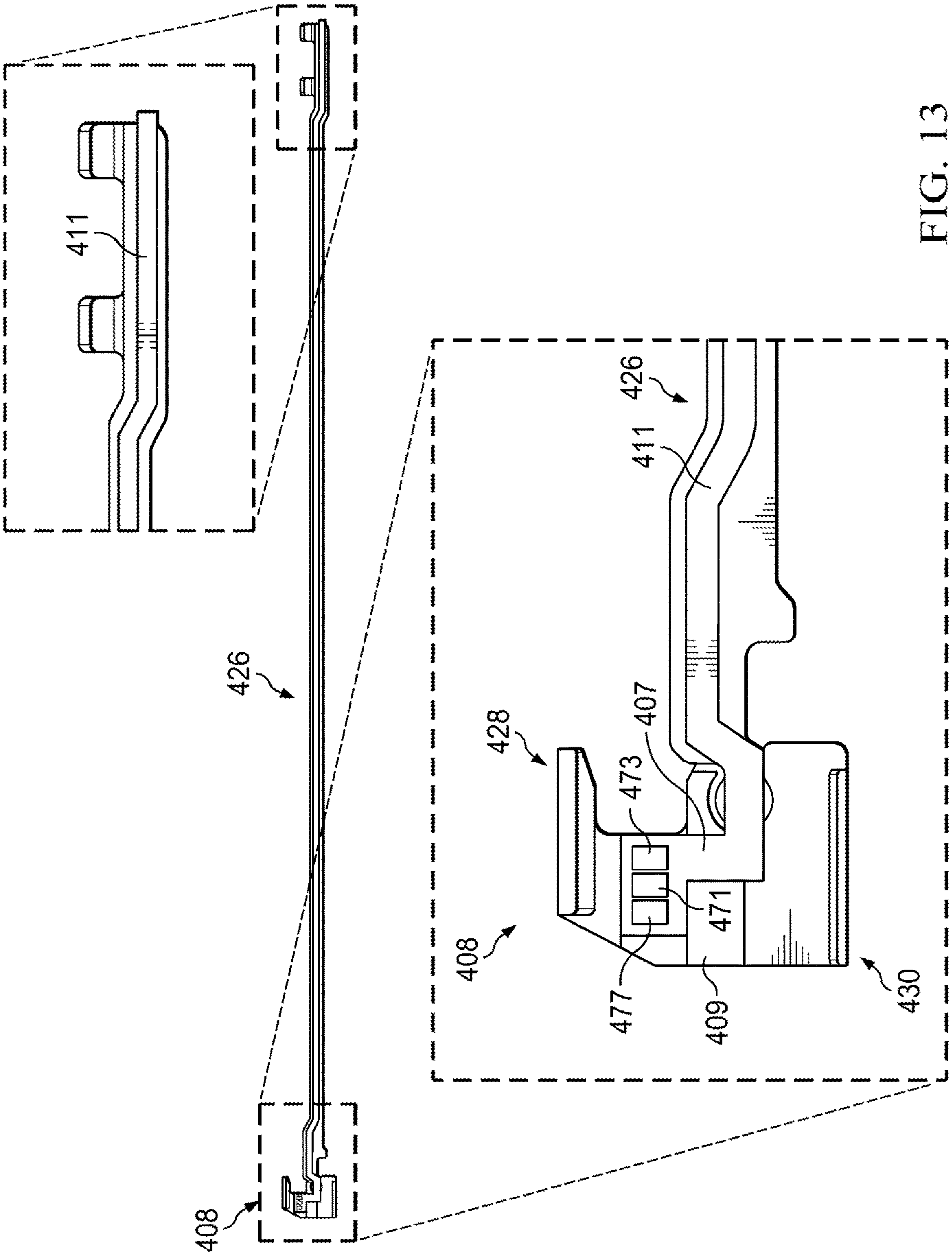
FIG. 13 depicts an example beam having first and second electrodes positioned at is distal end according to one embodiment.

Referring now to FIG. 13, an example beam 426 in accordance with one non-limiting embodiment of the present disclosure is illustrated. A blade assembly 408 at a distal end of the beam 426 can include a top portion 428, a bottom portion 420, and a blade 407. Similar to previous embodiments, the top portion 228 and the lower portion 230 that can compress an anvil and a cartridge of an end effector (not shown) when urged proximally. The blade assembly 408 has a first side surface 409 upon which first and second electrodes 471, 473 and a tissue sensor 477 can be coupled. As shown, the first and second electrodes 471, 473 and the tissue sensor 477 can be positioned proximally to the blade 407 such that tissue that is cut is placed in nearly immediate contact with the first and second electrodes 471, 473 and the and a tissue sensor 477. The first and second electrodes 471, 473 can be in electrical communication with an electrosurgical energy source (not shown) via the circuitry 411 extending along the beam 426. In some embodiments, the circuitry 411 can be coupled to the beam 426 using any suitable technique. For example, in some embodiments the circuitry 411 is placed within a slot that formed in the beam 426. In other embodiments, the circuitry 411 may be coined with the beam 426. The tissue sensor 477 can also deliver signals via the circuitry 411 extending along the beam 426.

The electrosurgical energy source can provide bipolar electrosurgical current that travels from the first electrode 471, through the intervening tissue, and to the second electrode 473 to complete the electrical circuit. More particularly, as the blade assembly 408 is urged proximally, the blade 407 transects tissue along the resection line 12 (FIG. 1) and energy can be simultaneously delivered to the resected tissue. Such energy can thereby heat the tissue and blood vessels along the resection line 12 to cauterize, coagulate/desiccate, and/or seal tissue along the resection line 12. The tissue sensor 477 can provide feedback signaling indicative of one or more tissue parameters, such as tissue impedance, tissue temperature, output current and/or voltage, etc.

The tissue will be split along the resection line 12, such that the incision has a first side and a second side. As the first and second electrodes 471, 473 are coupled to one side of the blade assembly 408, only one side of the incision (i.e., the first side) will contact the first and second electrodes 471, 473 during transection. In some embodiments, additional electrodes and one or more tissue sensors can be positioned on the other side of the blade assembly 408 so that both sides of the incision will contact a pair of electrodes and the tissue sensor(s). For instance, the pair of electrodes 471, 473 and tissue sensor 477 can be coupled to one side of the blade assembly 408, as is shown, and another pair of electrodes (not shown) can be placed on an opposite side of the blade assembly 408. The other pair of electrodes can also be in electrical communication with an electrosurgical energy source (not shown) via the circuitry 411 extending along the beam 426. In this arrangement, both sides of the incision can come into contact with a pair of electrodes during transection, with the tissue condition along both sides of the incision being monitored as well. As such, in accordance with various embodiments, electrodes on both sides of the blade assembly 408 can be used to simultaneously cauterize, coagulate/desiccate, and/or seal both sides of an incision formed by the blade assembly 408.

Figure 14:
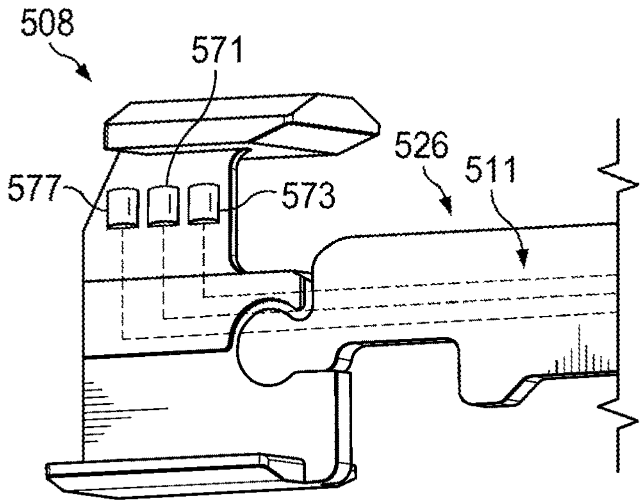
FIGS. 14-16 depict example blade assemblies according to various embodiments.
Figure 15:
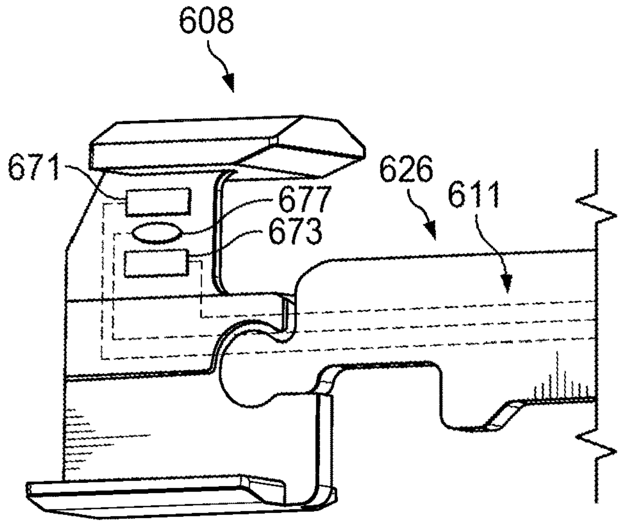

While FIG. 13 depicts one example arrangement of electrodes and tissue sensor, this disclosure is not so limited. In fact, a variety of different electrode layouts, as well as different electrode shapes, configurations, and placement locations of the electrode(s) and tissue sensor(s), as well as total number of electrodes and sensors, can be used without departing from the scope of the present disclosure. FIGS. 14-15 each depict example electrode and tissue sensor layouts in accordance with various embodiments. Moreover, while FIGS. 14-15 depict electrodes and one or more tissue sensors positioned on a first side of a blade assembly for illustration purposes, it is to be appreciated that electrodes and/or one or more tissue sensors can additionally or alternatively be placed on a second side of the blade assembly without departing from the scope of the present disclosure.

Referring first to FIGS. 14, a blade assembly 508 coupled to a beam 526 is depicted. First and second electrodes 571, 573 are coupled to one side of the blade assembly 508 and are in electrical communication with an electrosurgical energy source (not shown) via circuitry 511. A tissue sensor 577 is also coupled to one side of the blade assembly 508 to provide feedback to a tissue monitoring system (not shown) via the circuitry 511. In this embodiment, the first and second electrodes 571, 573 are placed along a longitudinal axis of the beam 526. In one embodiment, the first electrode 571 is an active electrode and the second electrode 573 is a return electrode. In another embodiment, the first electrode 571 is a return electrode and the second electrode 573 is an active electrode. Each of the first and second electrodes 571, 573 can have a curved outer surface, which can aid in bringing the first and second electrodes 571, 573 in contact with tissue during resection. In some embodiments, the first and second electrodes 571, 573 can each be a truncated cylinder (as shown). In other embodiments, the first and second electrodes 571, 573 can each be hemispherical, a rectangular block, or any of a variety of other suitable shapes. The tissue sensor 577 can have a similar form factor as the electrodes 571, 573, as shown in FIG. 14, or can have a different form factor without departing from the scope of the present disclosure.

Implementations of the disclosed technology that include tissue monitoring systems (see, for example, FIGS. 17A-23B) may include a closed loop control scheme that includes a feedback control loop wherein one or more tissue sensors (e.g., tissue sensors 477 and 577) provides feedback to a motor controller (e.g., motor controller 370). The tissue sensor can provide information obtained from one or more sensing mechanisms for sensing various tissue parameters such as tissue impedance, tissue temperature, output current and/or voltage, etc. The motor controller can then signal, through a motor controller board (e.g., motor controller board 238), an electrosurgical power generating source which can then adjust various operational parameters such as firing speed of the electrosurgical stapling device. The motor controller may include analog and/or logic circuitry for processing the sensed values from the tissue sensor and determining the control signals that are sent to the electrosurgical power generating source. The tissue sensor(s) can be provided with leads (or wireless) for transmitting information to the controller, with the tissue sensors translating along the tissue during a resection procedure.

In one non-limiting example, the one or more tissue sensors provide measured tissue temperature feedback to the motor controller for adjusting the firing speed of the electrosurgical stapling device. Energy from the electrosurgical power generating source is terminated and made inactive once the tissue temperature rises above a predetermined threshold, thereby stopping firing of the electrosurgical stapling device. In one embodiment, the predetermined threshold is between 80-120° C. Further, firing speed of the electrosurgical stapling device is decreased if tissue temperature at predetermined locations along resection line 12 (shown in FIG. 1) have not reached a predetermined target temperature. In one embodiment, the predetermined target temperature of the tissue is between 60-100° C.

In another non-limiting example, the one or more tissue sensors provide measured tissue impedance feedback to the motor controller for adjusting the firing speed of the electrosurgical stapling device. As tissue is cauterized along resection line 12, impedance within the tissue increases. Thus, energy from the electrosurgical power generating source is terminated and made inactive if tissue impedance at predetermined locations along resection line 12 has not reached a predetermined target impedance. Further, firing speed of the electrosurgical stapling device is decreased if tissue impedance rises above a predetermined threshold, thereby stopping firing of the electrosurgical stapling device. In one embodiment, the target impedance necessary to maintain a temperature between 90-100° C. is between 200-600 Ohms (Ω). Firing speed of the electrosurgical stapling device is decreased if tissue impedance is greater than 6000, and energy from the electrosurgical power generating source is made inactive if tissue impedance is below 200M.

Referring now to FIG. 15, a blade assembly 608 coupled to a beam 626 is depicted. First and second electrodes 671, 673 are coupled to one side of the blade assembly 608 and are in electrical communication with an electrosurgical energy source (not shown) via circuitry 611. A tissue sensor 677 is also coupled to one side of the blade assembly 608 to provide feedback to a tissue monitoring system via the circuitry 611. In this embodiment, the first and second electrodes 671, 673 are placed along an axis that is orthogonal to a longitudinal axis of the beam 626. In one embodiment, the first electrode 671 is an active electrode and the second electrode 673 is a return electrode. In another embodiment, the first electrode 671 is a return electrode and the second electrode 673 is an active electrode. While the first and second electrodes 671, 673 are schematically shown to be generally rectangular, the electrodes can each be any of a variety of other suitable shapes.

Figure 16:
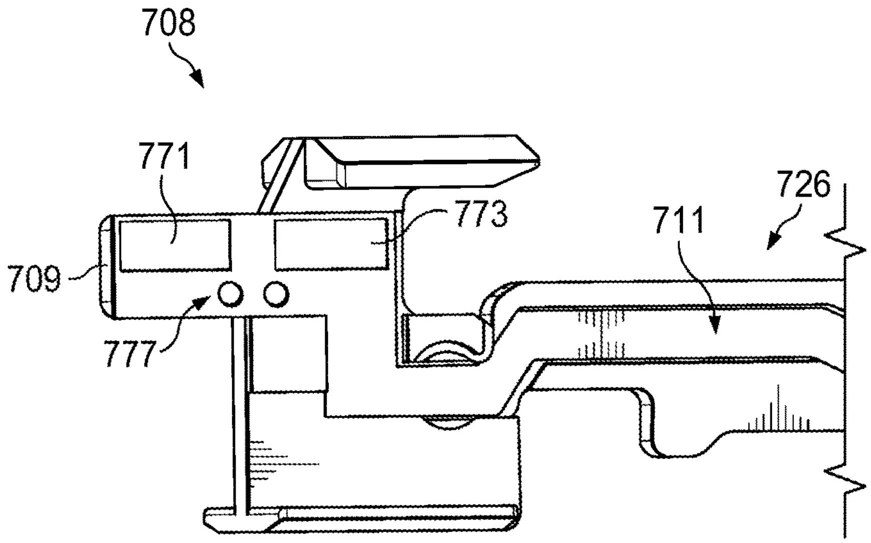

Referring now to FIG. 16, a blade assembly 708 coupled to a beam 726 is depicted. First and second electrodes 771, 773 are coupled to one side of the blade assembly 708 and are in electrical communication with an electrosurgical energy source (not shown) via circuitry 711. Tissue sensor 777 are also coupled to one side of the blade assembly 708 to provide feedback to a tissue monitoring system via the circuitry 711. In this embodiment, the blade assembly comprises a distal extension 709 that assists with achieving the desired placement of the electrodes. Such distal extension 709 can be used to accommodate larger sized electrodes and/or accommodate further lateral separation between the electrodes, for example.

Figure 17A:
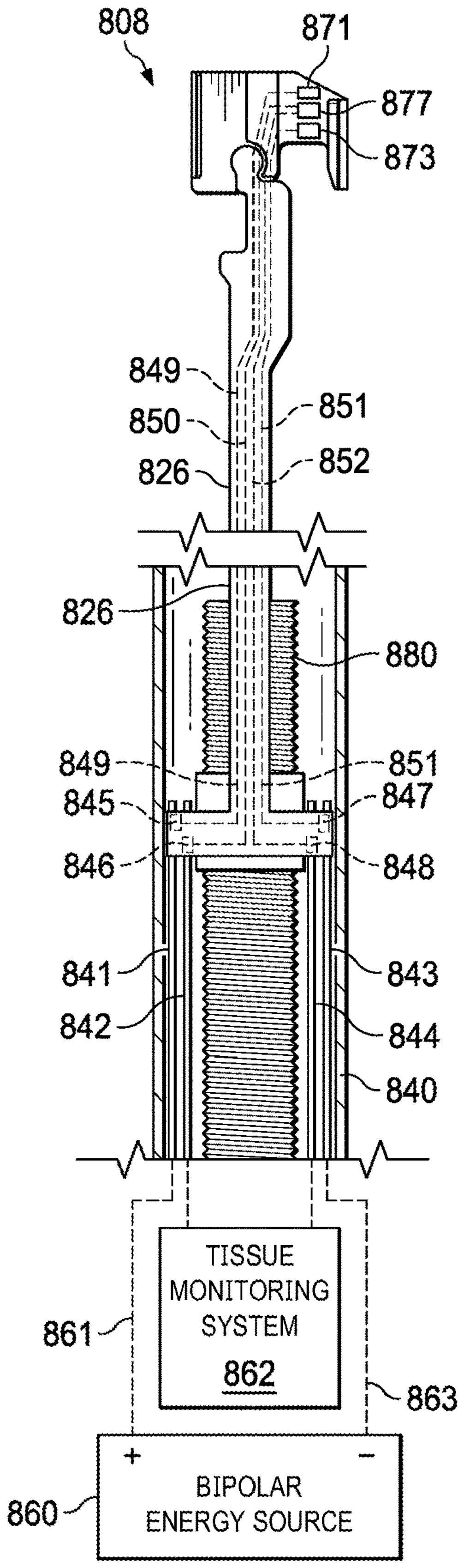
FIGS. 17A-17B schematically depict a non-limiting example embodiment electrically coupling electrodes to an electrosurgical energy source and maintaining such coupling during operation.
Figure 17B:
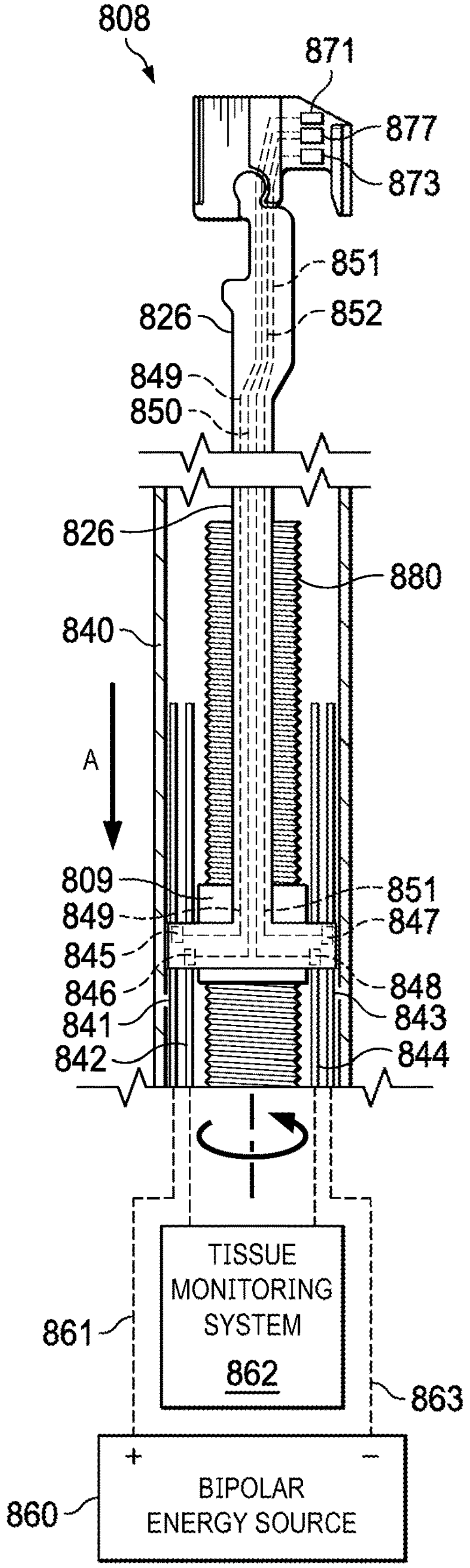

FIGS. 17A-17B schematically depicts one example non-limiting embodiment electrically coupling electrodes to an electrosurgical energy source, coupling a tissue sensor to a tissue monitoring system, and maintaining such coupling during operation. Referring first to FIG. 17A, a blade assembly 808 that is coupled to a beam 826 is shown extending into a support tube 840, which is shown in a cross-sectional view. First and second electrodes 871, 873 and tissue sensor 877 can be coupled to the blade assembly 808, as shown. Similar to the arrangement shown in FIG. 10, a nut 809 can be threaded to a rotating member 880, such that rotation of the rotating member 880 causes longitudinal traversal of the nut 809 along the length of the rotating member 880. A proximal end of the beam 826 can be coupled to, or otherwise engaged with, the nut 809, such that traversal of the nut 809 along the rotating member 880 in the proximal direction causes traversal of the beam 826 in the same direction.

The distal end of the beam can include a first contact 845 and a second contact 847. The first contact 845 can be in electrical contact with the first electrode 871 via a conductor 849 that is routed along the beam 826. The second contact 847 can be in electrical contact with the second electrode 873 via a conductor 851 that is routed along the beam 826. The distal end of the beam can also include a third contact 846 and a fourth contact 848. The third contact 846 can be in electrical contact with the tissue sensor 877 via a conductor 850 that is routed along the beam 826. The fourth contact 848 can be in electrical contact with the tissue sensor 877 via a conductor 852 that is routed along the beam 826.

A first conductive strip 841 can be positioned on an inside surface of the support tube 840. The first conductive strip 841 can be in electrical communication with an electrosurgical energy source, such as bipolar energy source 860, via a conductor 861. A second conductive strip 843 can also be positioned on an inside surface of the support tube 840. The second conductive strip 841 can be in electrical communication with an electrosurgical energy source, such the bipolar energy source 860, via a conductor 863. The first contact 845 can physically touch the first conductive strip 841 and maintain such contact while the first contact 845 translates relative to the first conductive strip 841. The second contact 847 can physically touch the second conductive strip 843 and maintain such contact while the second contact 847 translates relative to the second conductive strip 843.

A third conductive strip 842 can be positioned on an inside surface of the support tube 840. The third conductive strip 842 can be in electrical communication with a tissue monitoring system 862. A fourth conductive strip 844 can also be positioned on an inside surface of the support tube 840. The fourth conductive strip 844 can be in electrical communication with the tissue monitoring system 862. The third contact 846 can physically touch the third conductive strip 842 and maintain such contact while the third contact 846 translates relative to the third conductive strip 842. The fourth contact 848 can physically touch the fourth conductive strip 844 and maintain such contact while the fourth contact 848 translates relative to the fourth conductive strip 844.

Each of the contacts 845, 846, 847, and 848 can include brushes, leaf springs, or any other suitable connection allowing for the transfer of electrical current between the contact and respective conductive strip as the beam 826 translates relative to the support tube 840.

FIG. 17B, schematically depicts the delivery of energy to tissue (not shown) during operation. During operation, the nut 809 is translated in the direction indicate by arrow A by rotation of the rotating member 880. An energy supply path can be continuously provided to tissue being resected by the blade assembly 808. More particularly, the energy supply path formed from the bipolar energy source 860 to the first electrode 871 via a path that includes the conductor 861, the first conductive strip 841, the first contact 845, and the conductor 849. An energy return path can be continuously provided from the second electrode 873 to the bipolar energy source 860 via a path that includes the conductor 851, the second contact 847, the second conductive strip 843, and the conductor 863. Additionally, the tissue monitoring system 862 can receive continuous signaling from the tissue being resected by the blade assembly 808. More particularly, the circuit from the tissue monitoring system 862 to the tissue sensor 877 includes the third conductive strip 842, the third contact 846, and the conductor 850 on one leg and the fourth conductive strip 844, the fourth contact 848, and the conductor 852 on the other leg.

Figure 18A:
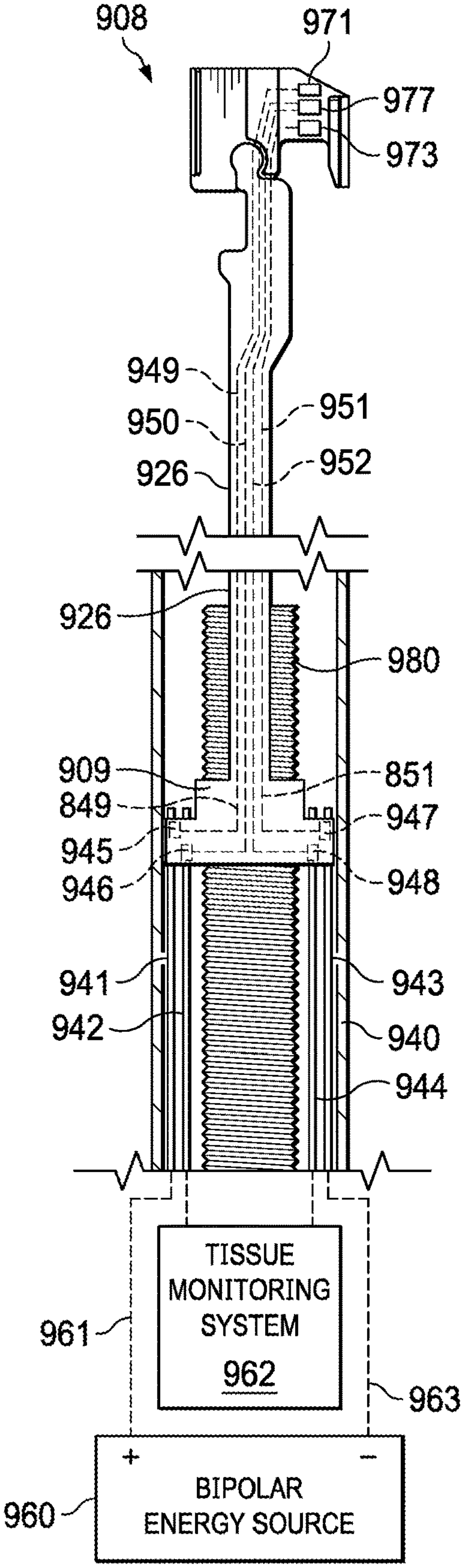
FIGS. 18A-18B schematically depict another non-limiting example embodiment electrically coupling electrodes to an electrosurgical energy source and maintaining such coupling during operation.
Figure 18B:
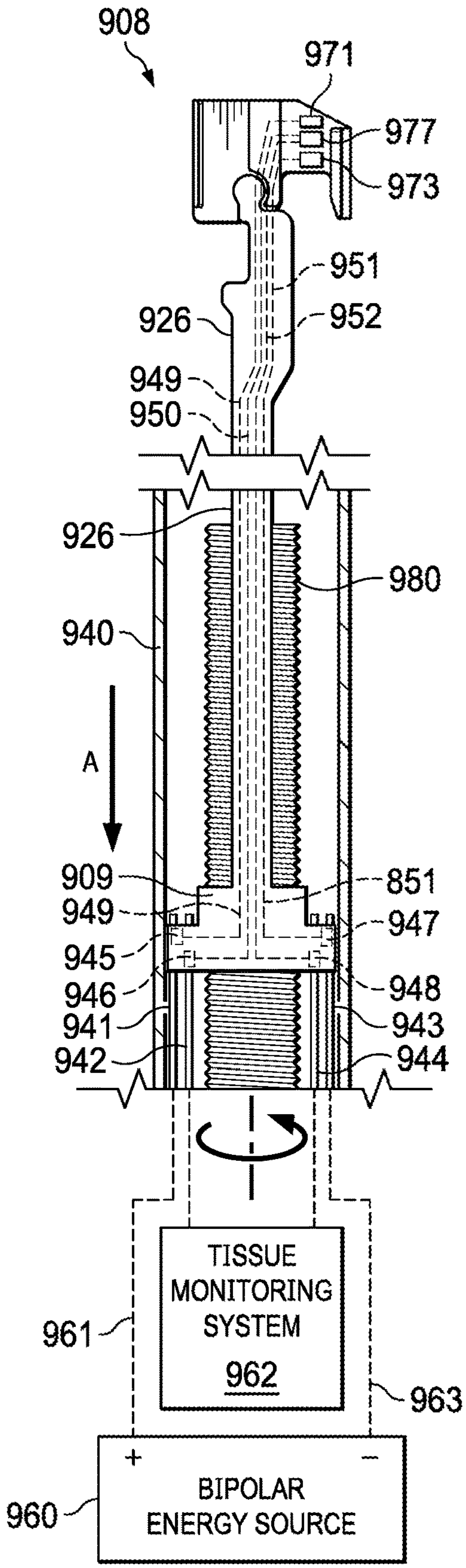

FIGS. 18A-18B schematically depicts another example non-limiting embodiment electrically coupling electrodes to an electrosurgical energy source, coupling a tissue sensor to a tissue monitoring system, and maintaining such coupling during operation. Referring first to FIG. 18A, a blade assembly 908 that is coupled to a beam 926 is shown extending into a support tube 940, which is shown in a cross-sectional view. First and second electrodes 971, 973 and tissue sensor 977 can be coupled to the blade assembly 998, as shown. A nut 909 can be threaded to a rotating member 980, such that rotation of the rotating member 980 causes longitudinal traversal of the nut 909 along the length of the rotating member 980. A proximal end of the beam 926 can be coupled to, or otherwise engaged with, the nut 909, such that traversal of the nut 909 along the rotating member 980 in the proximal direction causes traversal of the beam 926 in the same direction.

The nut 909 can include a first contact 945 and a second contact 947. The first contact 945 can be in electrical contact with the first electrode 971 via a conductor 949 that is routed from the nut 909 and then along the beam 926. The second contact 947 can be in electrical contact with the second electrode 973 via a conductor 951 that is routed from the nut 909 and then along the beam 926. The nut 909 can also include a third contact 946 and a fourth contact 948. The third contact 946 can be in electrical contact with the tissue sensor 977 via a conductor 950 that is routed along the beam 926. The fourth contact 948 can be in electrical contact with the tissue sensor 977 via a conductor 952 that is routed along the beam 926.

Similar to FIGS. 17A-17B, a first conductive strip 941 can be positioned on an inside surface of the support tube 940. The first conductive strip 941 can be in electrical communication with an electrosurgical energy source, such as bipolar energy source 960, via a conductor 961. A second conductive strip 943 can also be positioned on an inside surface of the support tube 940. The second conductive strip 941 can be in electrical communication with an electrosurgical energy source, such the bipolar energy source 960, via a conductor 963. The first contact 945 can physically touch the first conductive strip 941 and maintain such contact while the first contact 945 translates relative to the first conductive strip 941. The second contact 947 can physically touch the second conductive strip 943 and maintain such contact while the second contact 947 translates relative to the second conductive strip 943. A third conductive strip 942 can be positioned on an inside surface of the support tube 940. The third conductive strip 942 can be in electrical communication with a tissue monitoring system 962. A fourth conductive strip 944 can also be positioned on an inside surface of the support tube 940. The fourth conductive strip 944 can be in electrical communication with the tissue monitoring system 962. The third contact 946 can physically touch the third conductive strip 942 and maintain such contact while the third contact 946 translates relative to the third conductive strip 942. The fourth contact 948 can physically touch the fourth conductive strip 944 and maintain such contact while the fourth contact 948 translates relative to the fourth conductive strip 944.

Each of the contacts 945, 946, 947, and 948 can include brushes, leaf springs, or any other suitable connection allowing for the transfer of electrical current between the contact and respective conductive strip as the nut 909 translates relative to the support tube 940.

FIG. 18B, schematically depicts the delivery of energy to tissue (not shown) during operation. During operation, the nut 909 is translated in the direction indicate by arrow A by rotation of the rotating member 980. An energy supply path can be continuously provided to tissue being resected by the blade assembly 908. More particularly, the energy supply path formed from the bipolar energy source 960 to the first electrode 971 via a path that includes the conductor 961, the first conductive strip 941, the first contact 945, and the conductor 949. An energy return path can be continuously provided from the second electrode 973 to the bipolar energy source 960 via a path that includes the conductor 951, the second contact 947, the second conductive strip 943, and the conductor 963. Additionally, the tissue monitoring system 962 can receive continuous signaling from the tissue being resected by the blade assembly 908. More particularly, the circuit from the tissue monitoring system 962 to the tissue sensor 977 includes the third conductive strip 942, the third contact 946, and the conductor 950 on one leg and the fourth conductive strip 944, the fourth contact 948, and the conductor 952 on the other leg.

Figure 19:
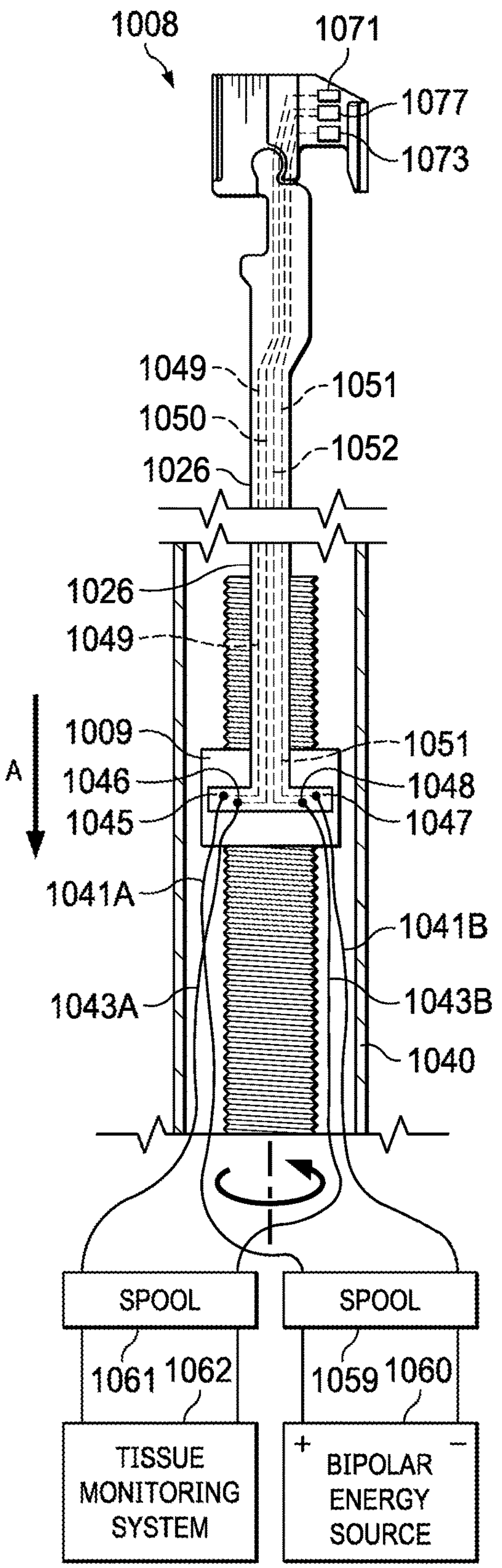
FIG. 19 schematically depicts another non-limiting example embodiment electrically coupling electrodes to an electrosurgical energy source and maintaining such coupling during operation.

FIG. 19 schematically depicts another example non-limiting embodiment electrically coupling electrodes to an electrosurgical energy source, coupling a tissue sensor to a tissue monitoring system, and maintaining such coupling during operation. A blade assembly 1008 that is coupled to a beam 1026 is shown extending into a support tube 1040, which is shown in a cross-sectional view. First and second electrodes 1071, 1073 and tissue sensor 1077 can be coupled to the blade assembly 1008, as shown. A nut 1009 can be threaded to a rotating member 1080, such that rotation of the rotating member 1080 causes longitudinal traversal of the nut 1009 along the length of the rotating member 1080. A proximal end of the beam 1026 can be coupled to, or otherwise engaged with, the nut 1009, such that traversal of the nut 1009 along the rotating member 1080 in the proximal direction causes traversal of the beam 1026 in the same direction.

The distal end of the beam 1026 can include a first contact 1045 and a second contact 1047. The first contact 1045 can be in electrical contact with the first electrode 1071 via a conductor 1049 that is routed along the beam 1026. The second contact 1047 can be in electrical contact with the second electrode 1073 via a conductor 1051 that is routed along the beam 1026. The distal end of the beam 1026 can also include a third contact 1046 and a fourth contact 1048. The third contact 1046 can be in electrical contact with the tissue sensor 1077 via a conductor 1050 that is routed along the beam 1026. The fourth contact 1048 can be in electrical contact with the tissue sensor 1077 via a conductor 1052 that is routed along the beam 1026.

A first conductor 1041A that is in electrical communication with an electrosurgical energy source, such as bipolar energy source 1060, can be routed into the support tube 1040 and connect to the first contact 1045. A second conductor 1041B that is in electrical communication with an electrosurgical energy source, such the bipolar energy source 1060, can also be routed into the support tube 1040 and connect to the second contact 1047. A third conductor 1043A that is in electrical communication with a tissue monitoring system 1062 can be routed into the support tube 1040 and connect to the third contact 1046. A fourth conductor 1043B that is in electrical communication with the tissue monitoring system 1062 can also be routed into the support tube 1040 and connect to the fourth contact 1048. The first and second conductors 1041A, 1041B can be wound around a spool 1059, which can be similar to the spool 159 of FIG. 8, for example. The third and fourth conductors 1043A, 1043B can be wound around a spool 1061, for example.

During operation, the nut 1009 is translated in the direction indicated by arrow A by rotation of the rotating member 1080. An energy supply path can be continuously provided to tissue being resected by the blade assembly 1008. More particularly, the energy supply path formed from the bipolar energy source 1060 to the first electrode 1071 via a path that includes the conductor 1041A, the first contact 1045, and the conductor 1049. An energy return path can be continuously provided from the second electrode 1073 to the bipolar energy source 1060 via a path that includes the conductor 1051, the second contact 1047, and the second conductor 1041B. As the nut 1009 is translated in the direction indicated by arrow A, rotation of the spool 1059 can collect excess slack in the first and second conductors 1041A, 1041B. Additionally, the tissue monitoring system 1062 can receive continuous signaling from the tissue being resected by the blade assembly 1008. More particularly, the circuit from the tissue monitoring system 1062 to the tissue sensor 1077 includes the third conductor 1043A, the third contact 1046, and the conductor 1050 on one leg and the fourth conductive 1043B, the fourth contact 1048, and the conductor 1052 on the other leg. As the nut 1009 is translated in the direction indicated by arrow A, rotation of the spool 1061 can collect excess slack in the third and fourth conductors 1043A, 1043B.

Figure 20:
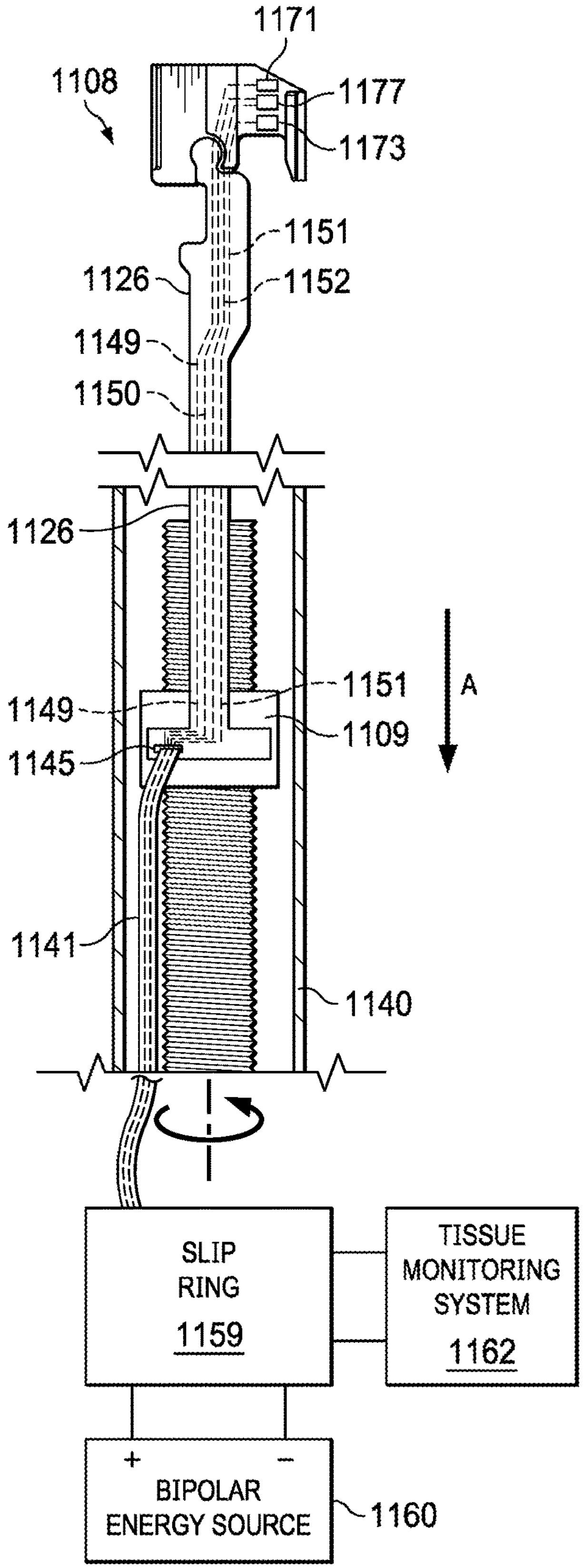
FIG. 20 schematically depicts yet an another non-limiting example embodiment electrically coupling electrodes to an electrosurgical energy source and maintaining such coupling during operation.

FIG. 20 schematically depicts another example non-limiting embodiment electrically coupling electrodes to an electrosurgical energy source, coupling a tissue sensor to a tissue monitoring system, and maintaining such coupling during operation. A blade assembly 1108 that is coupled to a beam 1126 is shown extending into a support tube 1140, which is shown in a cross-sectional view. First and second electrodes 1171, 1173 and tissue sensor 1177 can be coupled to the blade assembly 1108, as shown. A nut 1109 can be threaded to a rotating member 1180, such that rotation of the rotating member 1180 causes longitudinal traversal of the nut 1109 along the length of the rotating member 1180. A proximal end of the beam 1126 can be coupled to, or otherwise engaged with, the nut 1109, such that traversal of the nut 1109 along the rotating member 1180 in the proximal direction causes traversal of the beam 1126 in the same direction.

The distal end of the beam can include a flexible circuit connection 1045. The flexible circuit connection 1145 can be in electrical contact with the first electrode 1171 via a conductor 1149 that is routed along the beam 1126. The flexible circuit connection 1145 can also be in electrical contact with the second electrode 1173 via a conductor 1151 that is routed along the beam 1126. The flexible circuit connection 1145 can also be in electrical contact with the tissue sensor 1177 via conductors 1150, 1152 that are routed along the beam 1126.

A flexible circuit 1141 (sometimes referred to as a flexible printed circuit or flex circuit) that is in electrical communication with an electrosurgical energy source, such as bipolar energy source 1160, can be routed into the support tube 1140 and connect to the flexible circuit connection 1145. The flexible circuit 1141 can be in electrical communication with a slip ring 1159, which can be coupled to a spool, for example. The flexible circuit 1141 can house multiple conductors (i.e., traces) bonded to a substrate. For example, the flexible circuit 1141 can include first and second traces that are each in electrical communication with a bipolar energy source 1160 as well as traces that are in electrical communication with a tissue monitoring system 1162.

During operation, the nut 1109 is translated in the direction indicated by arrow A by rotation of the rotating member 1180. An energy supply path can be continuously provided to tissue being resected by the blade assembly 1108. More particularly, the energy supply path formed from the bipolar energy source 1160 to the first electrode 1171 via a path that includes the flexible circuit 1141, the flexible circuit connection 1145, and the conductor 1149. An energy return path can be continuously provided from the second electrode 1173 to the bipolar energy source 1160 via a path that includes the conductor 1151, the flexible circuit connection 1145, and the flexible circuit 1141. Additionally, the tissue monitoring system 1062 can receive continuous signaling from the tissue being resected by the blade assembly 1008.

Figure 21:
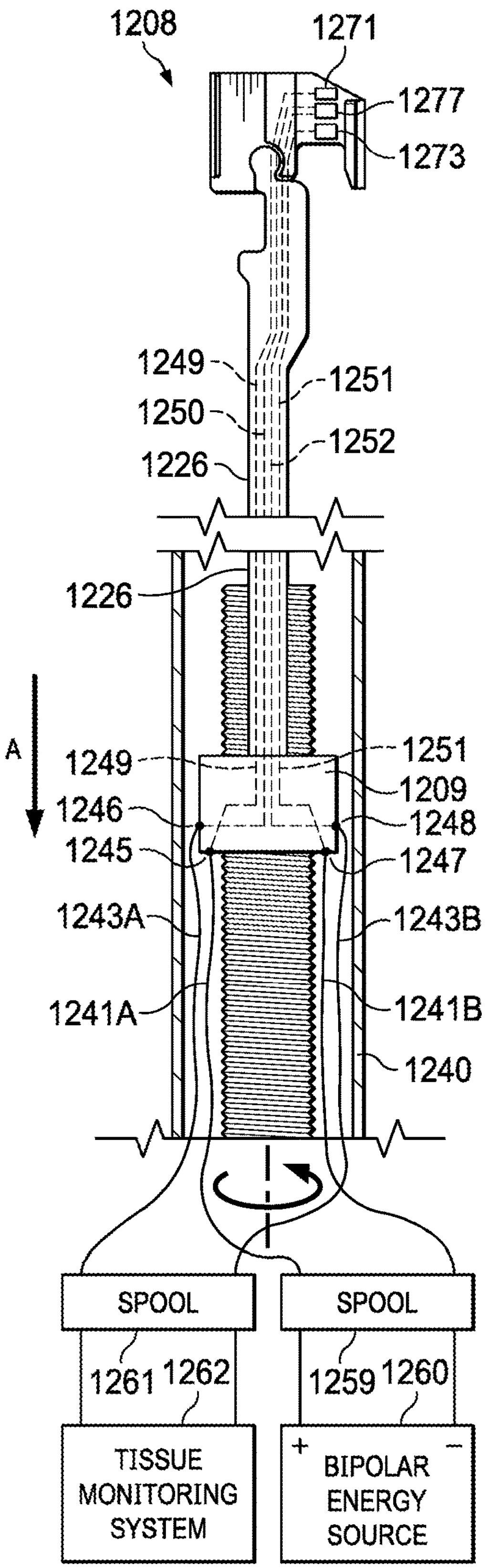
FIG. 21 schematically depicts another non-limiting example embodiment electrically coupling electrodes to an electrosurgical energy source and maintaining such coupling during operation.

FIG. 21 schematically depicts another example non-limiting embodiment electrically coupling electrodes to an electrosurgical energy source, coupling a tissue sensor to a tissue monitoring system, and maintaining such coupling during operation. A blade assembly 1208 that is coupled to a beam 1226 is shown extending into a support tube 1240, which is shown in a cross-sectional view. First and second electrodes 1271, 1273 and tissue sensor 1277 can be coupled to the blade assembly 1208, as shown. A nut 1209 can be threaded to a rotating member 1280, such that rotation of the rotating member 1280 causes longitudinal traversal of the nut 1209 along the length of the rotating member 1280. A proximal end of the beam 1226 can be coupled to, or otherwise engaged with, the nut 1209, such that traversal of the nut 1209 along the rotating member 1280 in the proximal direction causes traversal of the beam 1226 in the same direction.

The nut 1209 can include a first contact 1245 and a second contact 1247. The first contact 1245 can be in electrical contact with the first electrode 1271 via a conductor 1249 that is routed from the nut 1209 and then along the beam 1226. The second contact 1247 can be in electrical contact with the second electrode 1273 via a conductor 1251 that is routed from the nut 1209 and then along the beam 1226. The nut 1209 can also include a third contact 1246 and a fourth contact 1248. The third contact 1246 can be in electrical contact with the tissue sensor 1277 via a conductor 1250 that is routed along the beam 1226. The fourth contact 1248 can be in electrical contact with the tissue sensor 1277 via a conductor 1252 that is routed along the beam 1226.

A first conductor 1241A that is in electrical communication with an electrosurgical energy source, such as bipolar energy source 1260, can be routed into the support tube 1240 and connect to the first contact 1245. A second conductor 1241B that is in electrical communication with an electrosurgical energy source, such the bipolar energy source 1260, can also be routed into the support tube 1240 and connect to the second contact 1247. A third conductor 1243A that is in electrical communication with a tissue monitoring system 1262 can be routed into the support tube 1240 and connect to the third contact 1246. A fourth conductor 1243B that is in electrical communication with the tissue monitoring system 1262 can also be routed into the support tube 1240 and connect to the fourth contact 1248. The first and second conductors 1241A, 1241B can be wound around a spool 1259, which can be similar to the spool 159 of FIG. 8, for example. The third and fourth conductors 1243A, 1243B can be wound around a spool 1261, for example.

During operation, the nut 1209 is translated in the direction indicated by arrow A by rotation of the rotating member 1280. An energy supply path can be continuously provided to tissue being resected by the blade assembly 1208. More particularly, the energy supply path formed from the bipolar energy source 1260 to the first electrode 1271 via a path that includes the conductor 1241A, the first contact 1245, and the conductor 1249. An energy return path can be continuously provided from the second electrode 1273 to the bipolar energy source 1260 via a path that includes the conductor 1251, the second contact 1247, and the second conductor 1241B. As the nut 1209 is translated in the direction indicated by arrow A, rotation of the spool 1259 can collect excess slack in the first and second conductors 1241A, 1241B. Additionally, the tissue monitoring system 1262 can receive continuous signaling from the tissue being resected by the blade assembly 1208. More particularly, the circuit from the tissue monitoring system 1262 to the tissue sensor 1277 includes the third conductor 1243A, the third contact 1246, and the conductor 1250 on one leg and the fourth conductive 1243B, the fourth contact 1248, and the conductor 1252 on the other leg. As the nut 1209 is translated in the direction indicated by arrow A, rotation of the spool 1261 can collect excess slack in the third and fourth conductors 1243A, 1243B.

Figure 22:
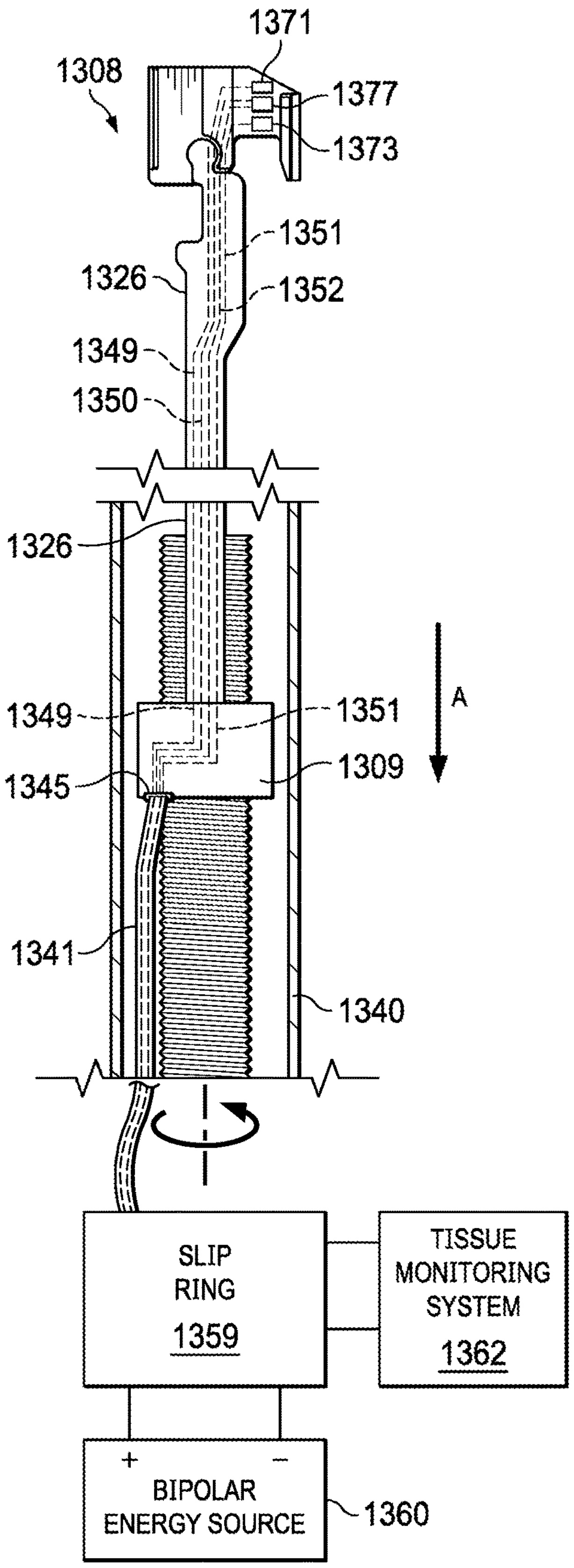
FIG. 22 schematically depicts yet an another non-limiting example embodiment electrically coupling electrodes to an electrosurgical energy source and maintaining such coupling during operation.

FIG. 22 schematically depicts another example non-limiting embodiment electrically coupling electrodes to an electrosurgical energy source coupling, a tissue sensor to a tissue monitoring system, and maintaining such coupling during operation. A blade assembly 1308 that is coupled to a beam 1326 is shown extending into a support tube 1340, which is shown in a cross-sectional view. First and second electrodes 1371, 1373 and tissue sensor 1177 can be coupled to the blade assembly 1308, as shown. A nut 1309 can be threaded to a rotating member 1380, such that rotation of the rotating member 1380 causes longitudinal traversal of the nut 1309 along the length of the rotating member 1380. A proximal end of the beam 1326 can be coupled to, or otherwise engaged with, the nut 1309, such that traversal of the nut 1309 along the rotating member 1380 in the proximal direction causes traversal of the beam 1326 in the same direction.

The nut 1309 can include a flexible circuit connection 1345. The flexible circuit connection 1345 can be in electrical contact with the first electrode 1371 via a conductor 1349 that is routed from the nut 1309 and then along the beam 1326. The flexible circuit connection 1345 can also be in electrical contact with the second electrode 1373 via a conductor 1351 that is routed from the nut 1309 and then along the beam 1326. The flexible circuit connection 1345 can also be in electrical contact with the tissue sensor 1377 via conductors 1350, 1352 that are routed along the beam 1326.

A flexible circuit 1341 (sometimes referred to as a flexible printed circuit or flex circuit) that is in electrical communication with an electrosurgical energy source, such as bipolar energy source 1360, can be routed into the support tube 1340 and connect to the flexible circuit connection 1345. The flexible circuit 1341 can be in electrical communication with a slip ring 1359, which can be coupled to a spool, for example. The flexible circuit 1341 can house multiple conductors (i.e., traces) bonded to a substrate. For example, the flexible circuit 1341 can include first and second traces that are each in electrical communication with a bipolar energy source 1360 as well as traces that are in electrical communication with a tissue monitoring system 1362.

During operation, the nut 1309 is translated in the direction indicated by arrow A by rotation of the rotating member 1380. An energy supply path can be continuously provided to tissue being resected by the blade assembly 1308. More particularly, the energy supply path formed from the bipolar energy source 1360 to the first electrode 1371 via a path that includes the flexible circuit 1341, the flexible circuit connection 1345, and the conductor 1349. An energy return path can be continuously provided from the second electrode 1373 to the bipolar energy source 1360 via a path that includes the conductor 1351, the flexible circuit connection 1345, and the flexible circuit 1341. Additionally, the tissue monitoring system 1362 can receive continuous signaling from the tissue being resected by the blade assembly 1308.

Figure 23A:
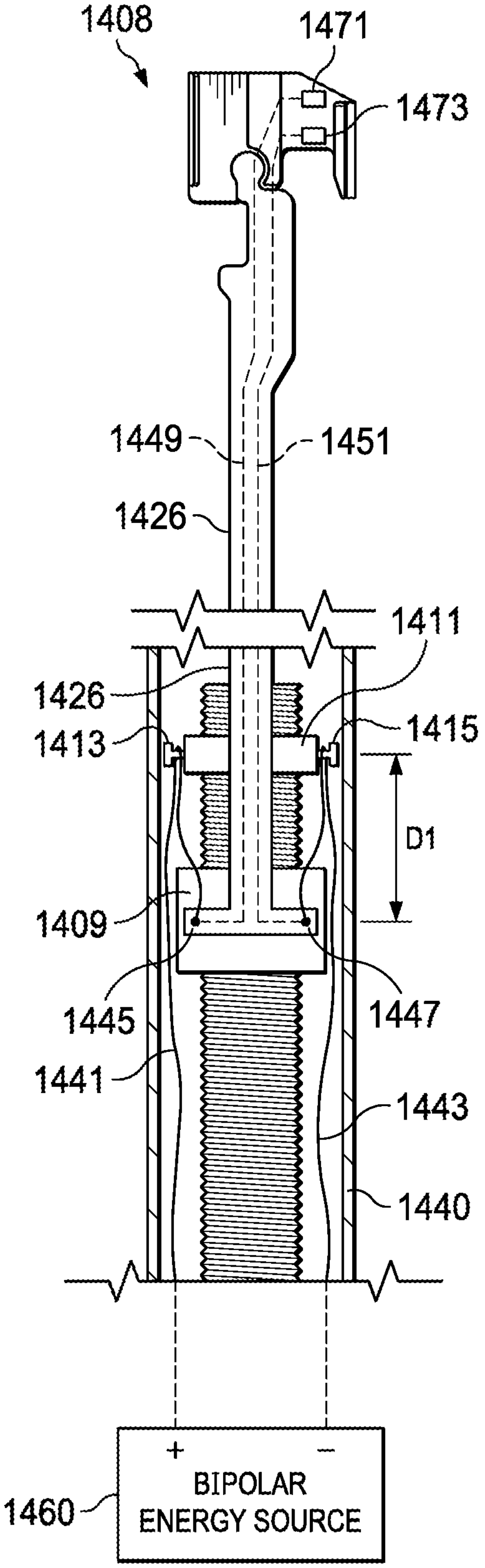
FIGS. 23A-23B schematically depict a non-limiting example embodiment electrically coupling electrodes to an electrosurgical energy source and maintaining such coupling during operation.
Figure 23B:
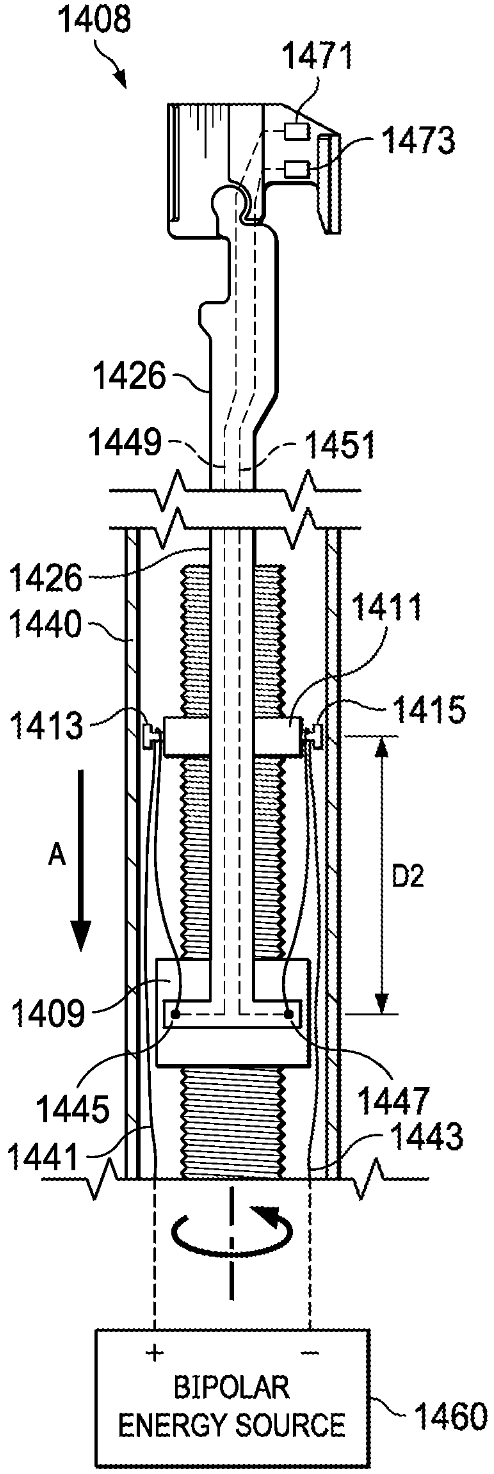

FIGS. 23A-23B schematically depict another example non-limiting embodiment electrically coupling electrodes to an electrosurgical energy source and maintaining such coupling during operation. A blade assembly 1408 that is coupled to a beam 1426 is shown extending into a support tube 1440, which is shown in a cross-sectional view. First and second electrodes 1471, 1473 can be coupled to the blade assembly 1408, as shown. A nut 1409 can be threaded to a rotating member 1480, such that rotation of the rotating member 1480 causes longitudinal traversal of the nut 1409 along the length of the rotating member 1480. A proximal end of the beam 1426 can be coupled to, or otherwise engaged with, the nut 1409, such that traversal of the nut 1409 along the rotating member 1480 in the proximal direction causes traversal of the beam 1426 in the same direction A follower nut 1411 can be positioned distally from the nut 1409. The follower nut 1411 can be threaded to the rotating member 1480, as shown, or can be threaded to a different rotating member. The follower nut 1411 can be configured such that it proximally transverses at a slower rate than the proximal traversal of the nut 1409. If the follower nut 1411 is threaded to the rotating member 1480, the follower nut 1411 can have a different thread pattern than nut 1409 in order to effectuate the rate difference. The follower nut 1411 can include one or more pins, illustrated as pin 1413 and pin 1415.

The distal end of the beam can include a first contact 1445 and a second contact 1447. The first contact 1445 can be in electrical contact with the first electrode 1471 via a conductor 1449 that is routed along the beam 1426. The second contact 1447 can be in electrical contact with the second electrode 1473 via a conductor 1451 that is routed along the beam 1426.

A first conductor 1441 that is in electrical communication with an electrosurgical energy source, such as bipolar energy source 1460, can be routed into the support tube 1440, loop around the pin 1413, and then connect to the first contact 1445. A second conductor 1443 that is in electrical communication with an electrosurgical energy source, such the bipolar energy source 1460, can also be routed into the support tube 1440, loop around the pin 1415, and then connect to the second contact 1447.

During operation, an energy supply path can be continuously provided to tissue being resected by the blade assembly 1408. More particularly, the energy supply path formed from the bipolar energy source 1460 to the first electrode 1471 via a path that includes the conductor 1441, the first contact 1445, and the conductor 1449. An energy return path can be continuously provided from the second electrode 1473 to the bipolar energy source 1460 via a path that includes the conductor 1451, the second contact 1447, and the second conductor 1443.

The nut 1409 may initially be longitudinal separated from the follower nut 1411 by a distance D1 (FIG. 23A). Both nuts can be translated in the direction indicated by arrow A by rotation of the rotating member 1480. The nut 1409 can travel a further distance, thereby increasing the distance between the nut 1409 and the follower nut 1411 to a distance D2 (FIG. 23B). Since the conductor 1441 and the conductor 1443 are looped around pins 1413 and 1415, respectfully, such increase in separation during operation can help to manage the slack formed in the conductor 1441 and the conductor 1443 as the nut 1409 is translated in the direction indicated by arrow A. Additionally, in some embodiments, a tissue sensor can be coupled to the blade assembly. Conductors associated with the tissue sensor can be routed similarly conductors 1441 and 1443 to help manage their slack during operation.

Figures 24A, 24B:
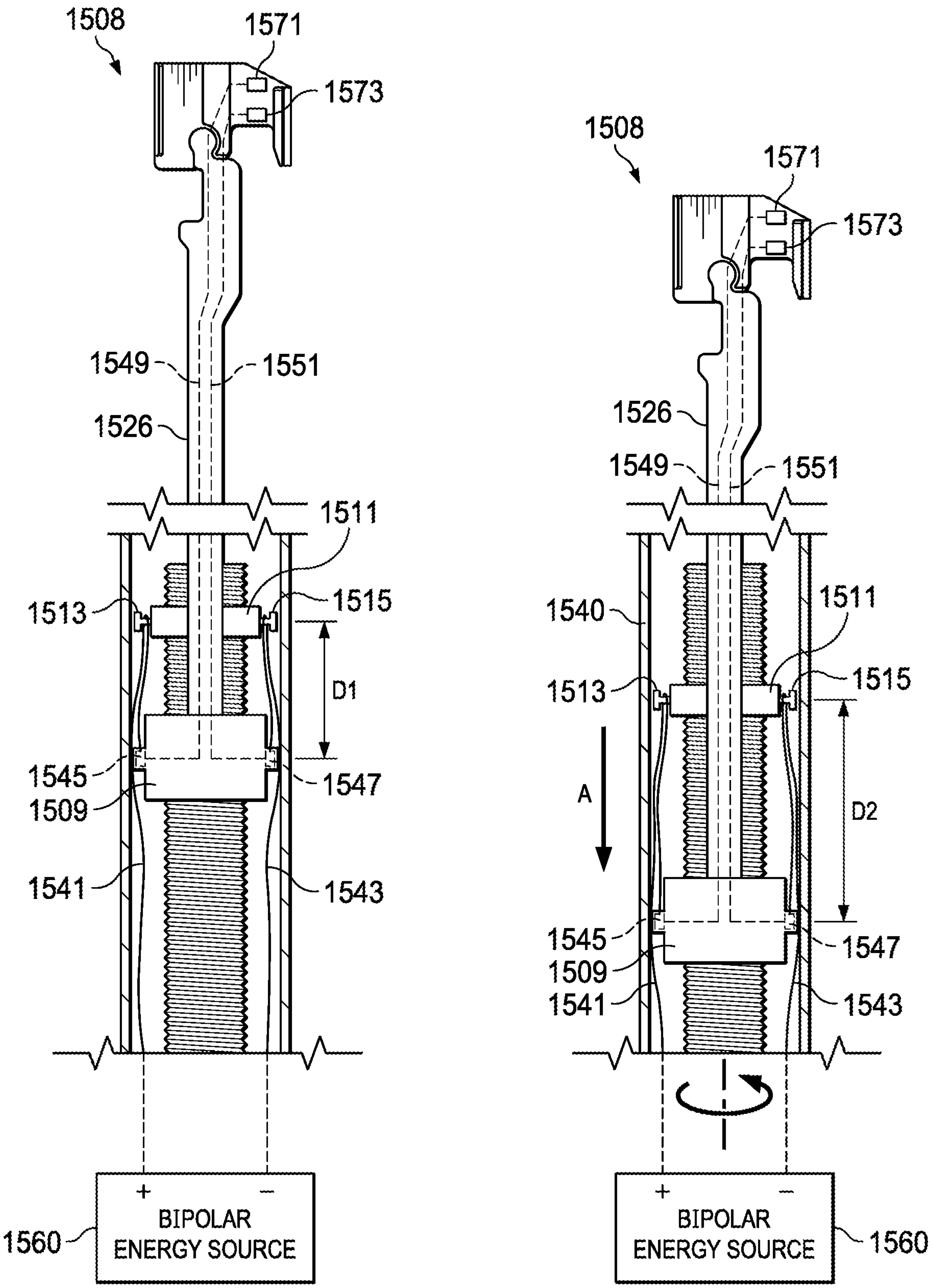
FIGS. 24A-24B schematically depict another non-limiting example embodiment electrically coupling electrodes to an electrosurgical energy source and maintaining such coupling during operation.

FIGS. 24A-24B schematically depict another example non-limiting embodiment electrically coupling electrodes to an electrosurgical energy source and maintaining such coupling during operation. A blade assembly 1508 that is coupled to a beam 1526 is shown extending into a support tube 1540, which is shown in a cross-sectional view. First and second electrodes 1571, 1573 can be coupled to the blade assembly 1508, as shown. A nut 1509 can be threaded to a rotating member 1580, such that rotation of the rotating member 1580 causes longitudinal traversal of the nut 1509 along the length of the rotating member 1580. A proximal end of the beam 1526 can be coupled to, or otherwise engaged with, the nut 1509, such that traversal of the nut

1509 along the rotating member 1580 in the proximal direction causes traversal of the beam 1526 in the same direction.

A follower nut 1511 can be positioned distally from the nut 1509. The follower nut 1511 can be threaded to the rotating member 1580, as shown, or can be threaded to a different rotating member. The follower nut 1511 can be configured such that it proximally transverses at a slower rate than the proximal traversal of the nut 1509. If the follower nut 1511 is threaded to the rotating member 1580, the follower nut 1511 can have a different thread pattern than nut 1509 in order to effectuate the rate difference. The follower nut 1511 can include one or more pins, illustrated as pin 1513 and pin 1515.

The nut 1509 include a first contact 1545 and a second contact 1547. The first contact 1545 can be in electrical contact with the first electrode 1571 via a conductor 1549 that is routed from the nut 1509 and then along the beam 1526. The second contact 1547 can be in electrical contact with the second electrode 1573 via a conductor 1551 that is routed from the nut 1509 and then along the beam 1526.

A first conductor 1541 that is in electrical communication with an electrosurgical energy source, such as bipolar energy source 1560, can be routed into the support tube 1540, loop around the pin 1513, and then connect to the first contact 1545. A second conductor 1543 that is in electrical communication with an electrosurgical energy source, such the bipolar energy source 1560, can also be routed into the support tube 1540, loop around the pin 1515, and then connect to the second contact 1547.

During operation, an energy supply path can be continuously provided to tissue being resected by the blade assembly 1508. More particularly, the energy supply path formed from the bipolar energy source 1560 to the first electrode 1571 via a path that includes the conductor 1541, the first contact 1545, and the conductor 1549. An energy return path can be continuously provided from the second electrode 1573 to the bipolar energy source 1560 via a path that includes the conductor 1551, the second contact 1547, and the second conductor 1543.

The nut 1509 may initially be longitudinal separated from the follower nut 1511 by a distance D1 (FIG. 24A). Both nuts can be translated in the direction indicated by arrow A by rotation of the rotating member 1580. The nut 1509 can travel a further distance, thereby increasing the distance between the nut 1509 and the follower nut 1511 to a distance D2 (FIG. 24B). Since the conductor 1541 and the conductor 1543 are looped around pins 1513 and 1515, respectfully, such increase in separation during operation can help to manage the slack formed in the conductor 1541 and the conductor 1543 as the nut 1509 is translated in the direction indicated by arrow A. Additionally, in some embodiments, a tissue sensor can be coupled to the blade assembly. Conductors associated with the tissue sensor can be routed similarly conductors 1541 and 1543 to help manage their slack during operation.

Figure 25:
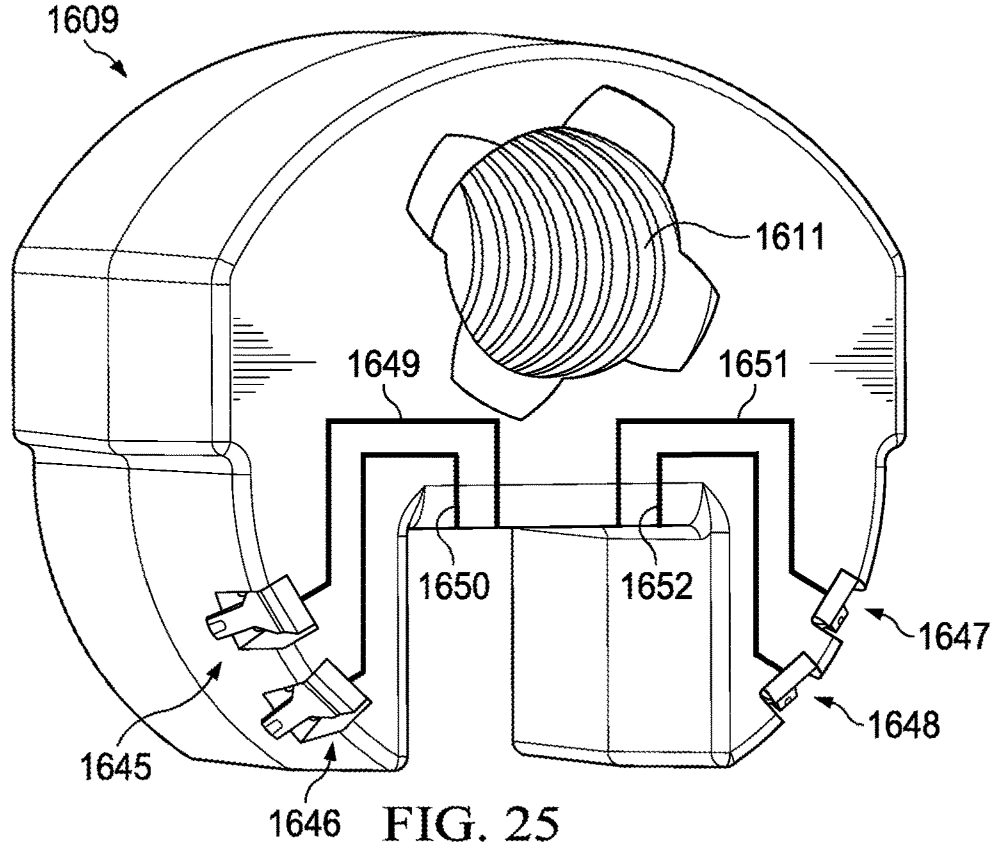
FIG. 25 depicts a nut having electrical contacts in accordance with an example embodiment.

Referring now to FIG. 25, an example nut 1609 in accordance with one non-limiting embodiment is illustrated. The nut 1609 can be similar to, for example nut 909 (FIGS. 18A-18B). The nut 1609 can include threads 1611 that are configured to engage a rotating member. The nut 1609 can also include a first contact 1645, a second contact 1646, a third contact 1647, and a fourth contact 1648. In FIG. 25, the contacts 1645, 1646, 1647, and 1648 are illustrated as leaf springs that are configured to contact conductive strips, such as conductive strips 941, 942, 943, and 944 (FIG. 18A-18B). The nut 1609 can also include conductors 1649, 1650, 1651, and 1652 that are coupled to circuitry on a beam (not shown).

Figure 26:
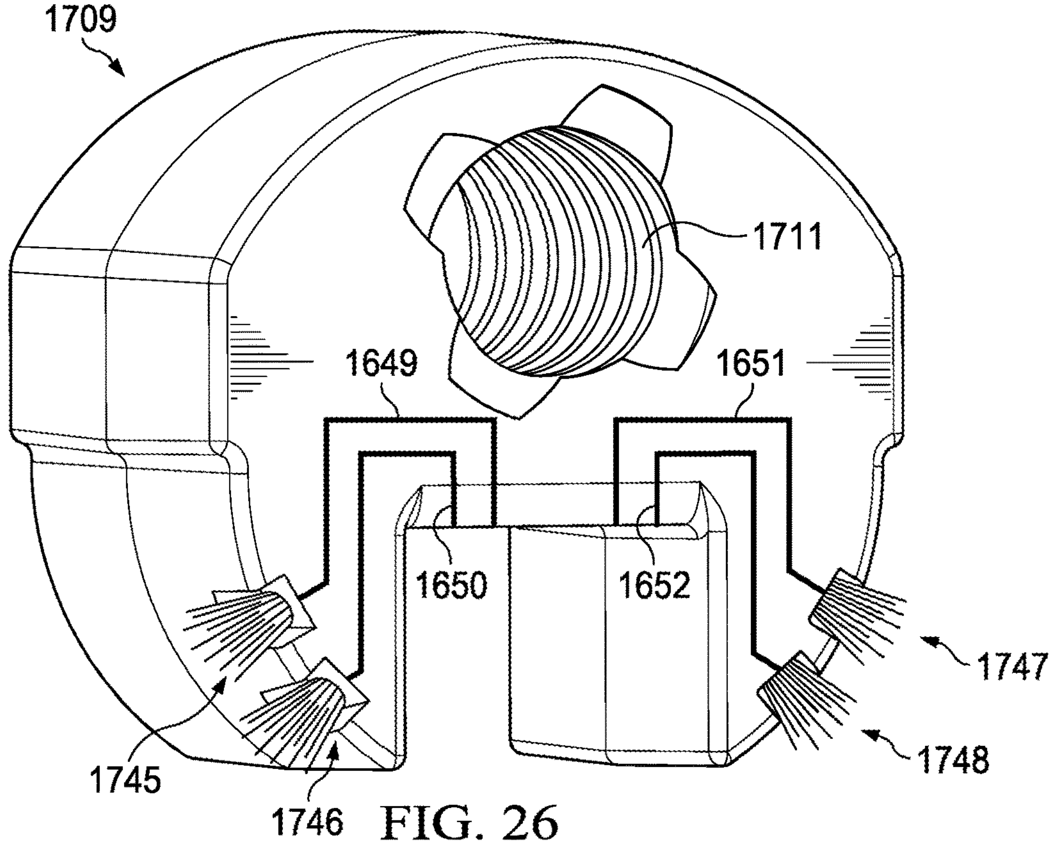
FIG. 26 depicts another nut having electrical contacts in accordance with another example embodiment.

Referring now to FIG. 26, another example nut 1709 in accordance with one non-limiting embodiment is illustrated. The nut 1709 can be similar to, for example nut 909 (FIGS. 18A-18B). The nut 1709 can include threads 1711 that are configured to engage a rotating member. The nut 1709 can also include a first contact 1745, a second contact 1746, a third contact 1747, and a fourth contact 1748. In FIG. 26, the contacts 1745, 1746, 1747, and 1748 are illustrated as brushes are configured to contact conductive strips, such as conductive strips 941, 942, 943, and 944 (FIG. 18A-18B). The nut 1709 can also include conductors 1649, 1650, 1651, and 1652 that are coupled to circuitry on a beam (not shown).

Figure 27:
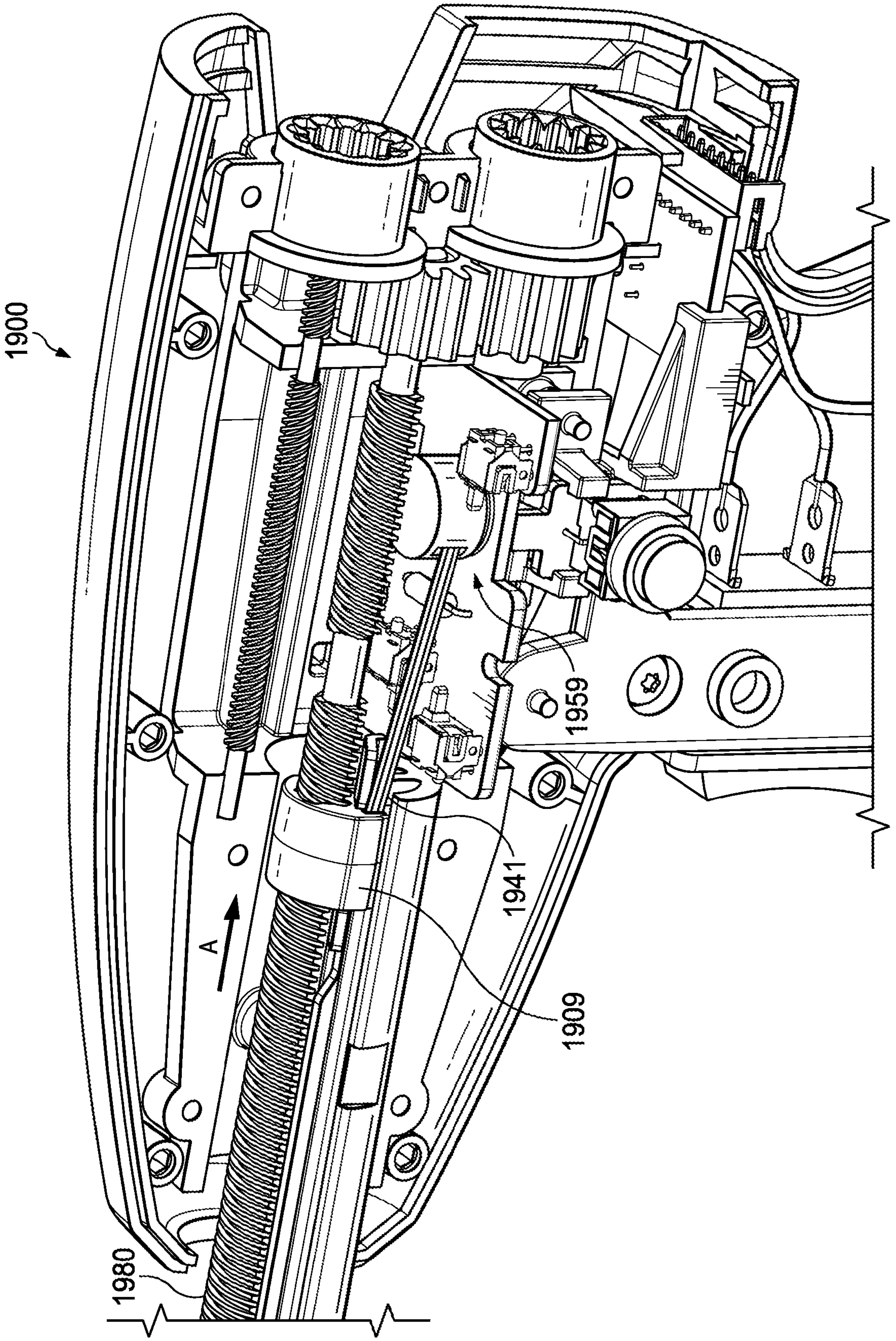
FIG. 27 is a sectioned side view of a handle assembly of an example electrosurgical stapling device.

Referring now to FIG. 27, a cutaway view of an example electrosurgical stapling device 1900. The electrosurgical stapling device 1900 can be similar to the electrosurgical stapling device 100 (FIGS. 1-2). In this regard, the electrosurgical stapling device 1900 can include a nut 1909 that translates along a rotating member 1980 during rotation of the rotating member 1980. In the illustrated embodiment, flexible circuit 1941 is connected to the nut 1909, similar to the arrangement in FIG. 22, for example. A spool assembly 1959 can be configured to receive the flexible circuit 1941 as the nut 1909 translates in the direction indicate by arrow A during operation.

Figure 28:
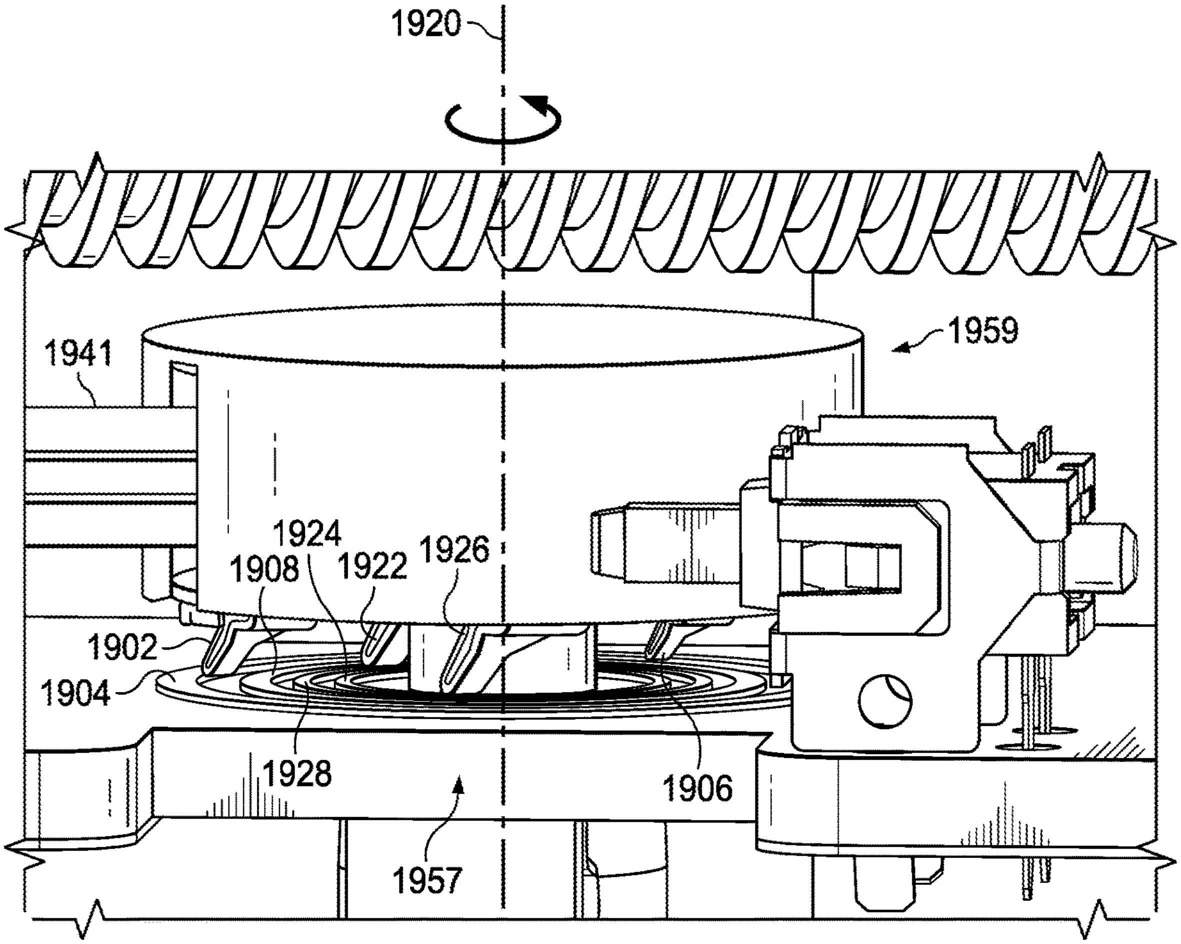
FIG. 28 is an enlarged view of the example spool depicted in FIG. 27.
Figure 29:
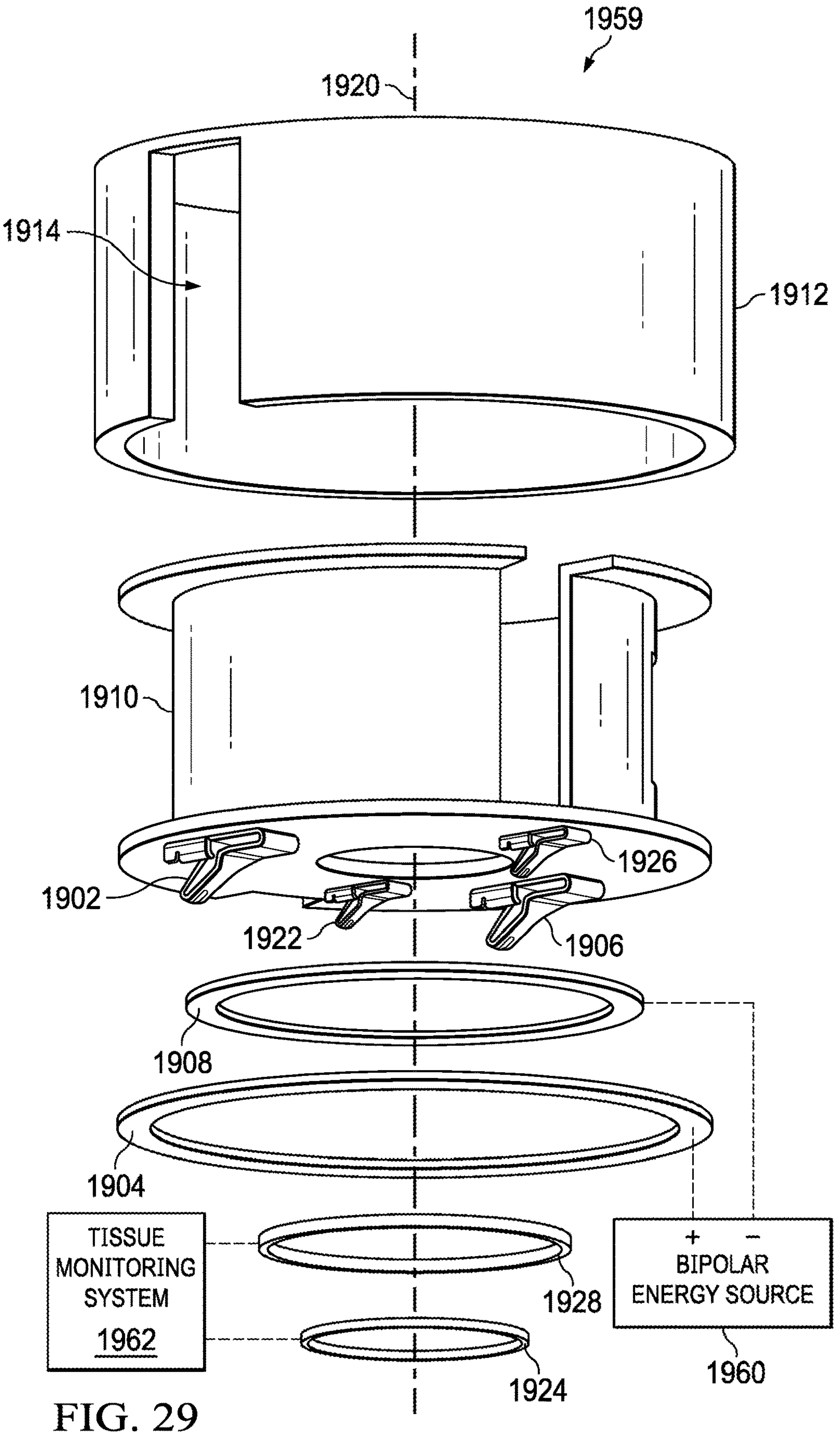
FIG. 29 is an exploded view of the spool depicted in FIG. 28.

FIG. 28 provides an enlarged view of the spool assembly 1959 and FIG. 29 provides an exploded view of the spool assembly 1959. The spool assembly 1959 can comprise a shell 1912 that defines a slot 1914 through which the flexible circuit 1941 passes and wraps around a bobbin 1910. The bobbin 1910 can be rotated around its axis of rotation 1920 as the nut 1909 translates toward the spool assembly 1959 to collect the flexible circuit 1941. Thus, during operation, the bobbin 1910 can be rotated relative to the shell 1912 to draw the flexible circuit 1941 into the spool assembly 1959.

The spool assembly 1959 can also include a slip ring assembly 1957 to deliver energy to the flexible circuit 1941. The slip ring assembly 1957 can include first and second contacts 1902, 1906 that are positioned on an outer surface of the bobbin 1910. The contacts 1902, 1906, 1922, and 1926 can be in electrical communication with the flexible circuit 1941 through any suitable connections. The first contact 1902 can be configured to remain in constant contact with a first circular electrode 1904 during rotation of the bobbin 1910. The second contact 1906 can be configured to remain in constant contact with a second circular electrode 1908 during rotation of the bobbin 1910. Each of the first and second electrodes 1904, 1908 can be in electrical communication with a bipolar energy source 1960 (FIG. 29). The third contact 1922 can be configured to remain in constant contact with a third circular electrode 1928 during rotation of the bobbin 1910. The fourth contact 1926 can be configured to remain in constant contact with a fourth circular electrode 1924 during rotation of the bobbin 1910. The third and fourth electrodes 1928, 1924 can be in electrical communication with a tissue monitoring system 1962.

Figure 30:
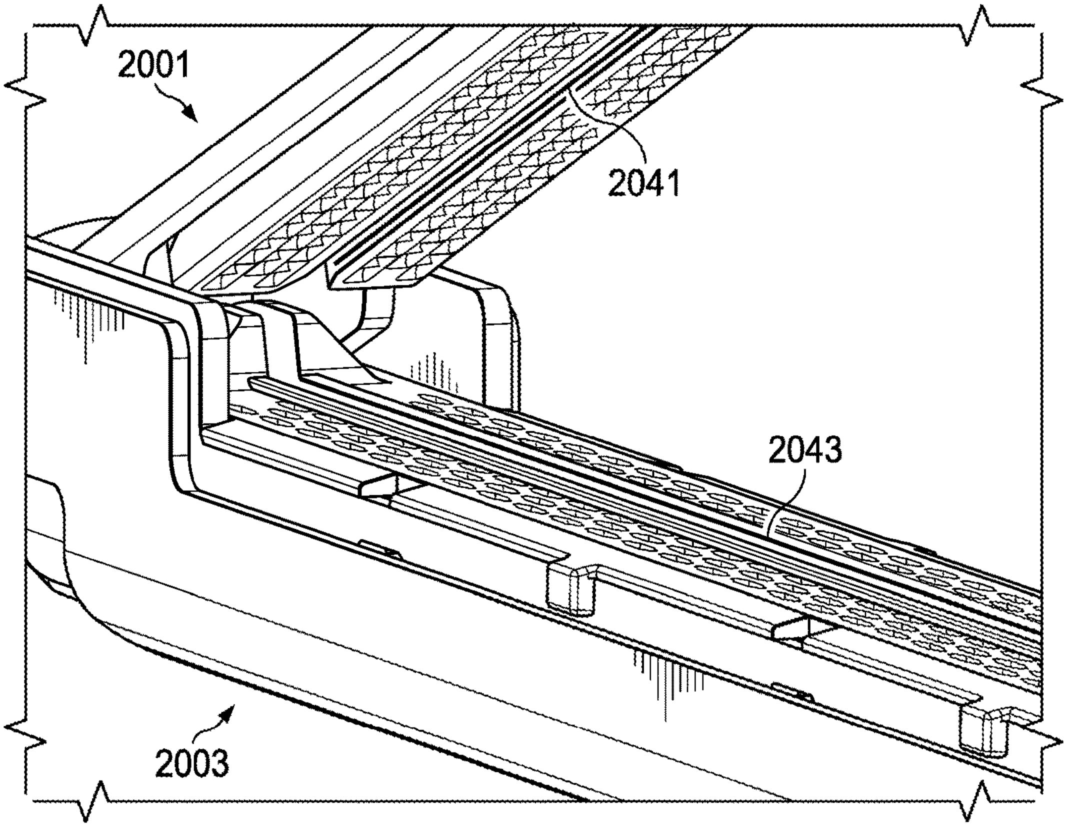
FIG. 30 is a partial view of an example end effector in accordance with an example embodiment.
Figure 31:
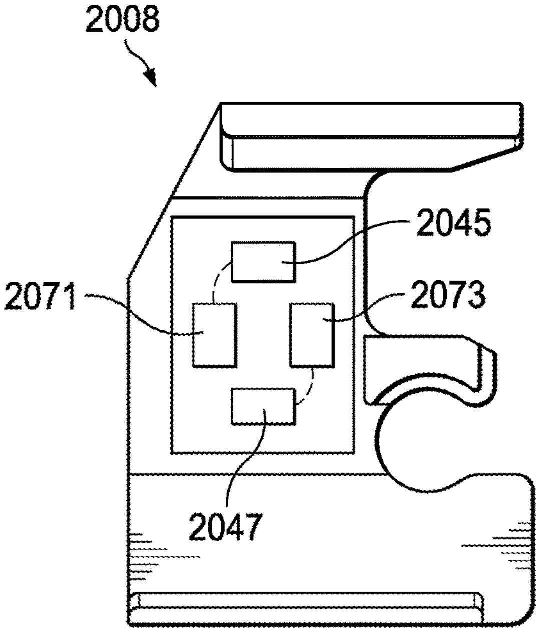
FIGS. 31-36 are example blade assemblies in accordance with various embodiments.

While certain embodiments described herein describe the use of circuitry along the beam to deliver electrosurgical energy to electrodes positioned on a blade assembly, this disclosure is not so limited. Referring to FIGS. 30-31, for example, an example embodiment is illustrated in which a first conductive strip 2041 is positioned internal to an anvil assembly 2001 and a second conductive strip 2043 is positioned internal to a cartridge assembly 2003. Each of the conductive strips 2041, 2043 can be in electrical communication with a suitable electrosurgical energy source (not shown). FIG. 30 depicts an example blade assembly 2008 that has first and second electrodes 2071, 2073, which can be generally similar to previous embodiments. The example blade assembly 2008 also has a first pickup electrode 2045 that is in electrical communication with the first electrode 2071. The first pickup electrode 2045 is configured to contact the first conductive strip 2041 that is positioned internal to the anvil assembly 2001. The example blade assembly 2008 also has a second pickup electrode 2047 that is in electrical communication with the second electrode 2073. The second pickup electrode 2047 is configured to contact the second conductive strip 2043 that is positioned internal to the cartridge assembly 2003. Thus, as the blade assembly 2008 is through the anvil assembly 2001 and the cartridge assembly 2003 during an operational strike, the pickup electrodes 2045, 2047 can remain in contact with the conductive strips 2041, 2043.

Figure 32:
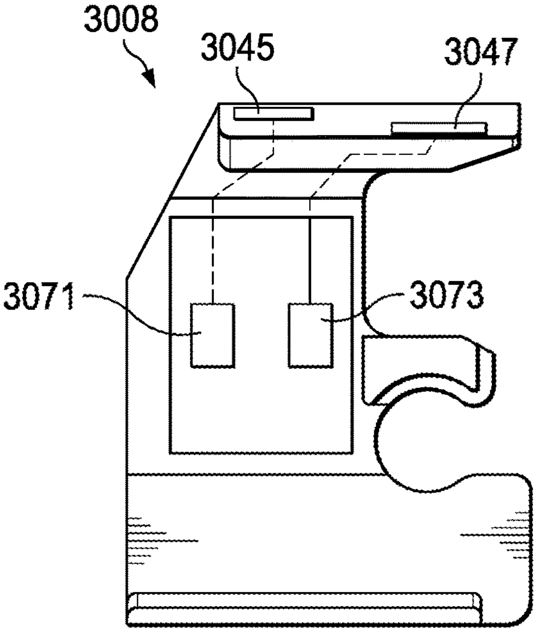

FIG. 32 depicts another example blade assembly 3008 that has first and second electrodes 3071, 3073, which can be generally similar to previous embodiments. The example blade assembly 3008 also has a first pickup electrode 3045 that is in electrical communication with the first electrode 3071. The first pickup electrode 3045 is configured to contact a first conductive strip that is positioned internal to an anvil assembly. The example blade assembly 3008 also has a second pickup electrode 3047 that is in electrical communication with the second electrode 3073. The second pickup electrode 3047 is configured to contact a second conductive strip that is positioned internal to the anvil assembly. The configuration of FIG. 32 can allow for the construction strips in the anvil assembly to be further embedded, and therefore further away from a patient's tissue during operation. As is to be appreciated, similar approaches as those depicted in FIGS. 30-32 can be used to implement a tissue sensor on a blade assembly utilizing conductive strips positioned in the anvil assembly 2001 and the cartridge assembly 2003.

While many of the present embodiments depict the use of electrodes, it is to be appreciated that any suitable technique can be used to cauterize, coagulate/desiccate, and/or seal tissue. For example, in some implementations, one or more resistive heating elements can be coupled to a blade assembly. When energized, the one or more resistive heating elements can deliver heat directly to tissue along an incision. In some implementations, one or more resistive heating elements can be placed only on a single side of a blade assembly, such that heat is directed to a single side of an incision. Alternatively, one or more resistive heating elements can be placed on both sides of a blade assembly. Furthermore, in some embodiments, a blade assembly can include a heating assembly that comprises the resistive heating element as well as, for example, a heating pad or other suitable heat dissipating structure. Such structure can be positioned in close proximity to a resistive heating element and be configured to directly contact tissue. The heat dissipating structure can help to dissipate the heat from the resistive heating element into tissue during transection, for example.

Figure 33:
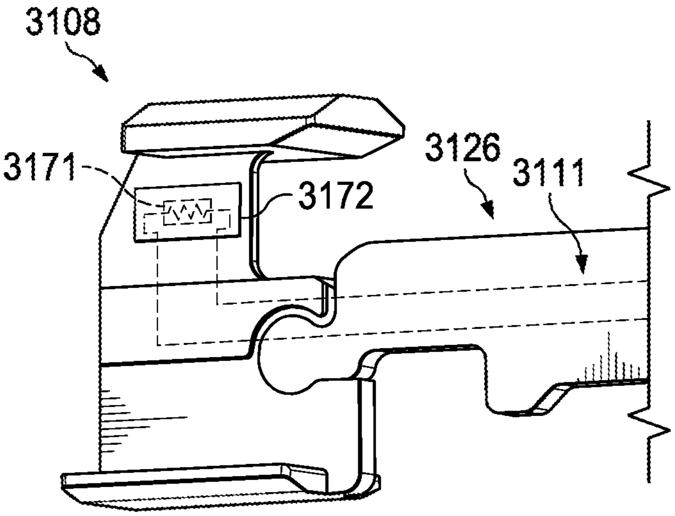

FIG. 33 depicts an example blade assembly 3108 that includes an example resistive heating element 3171. The example blade assembly 3108 also has a heating pad 3172 that covers the resistive heating element 3171 and is configured to assist with dissipating the heat generated by the resistive heating element 3171 during operation. The resistive heating element 3171 can be energized via circuitry 3111 extending along the beam 3126. While FIG. 33 depicts a resistive heating element 3171 placed on only a first side of the blade assembly 3108, it is to be appreciated that other embodiments can also have a similar resistive heating element placed on the other side as well. Additionally, one or more tissue sensors can be incorporated into the blade assembly 3108 in accordance with the present disclosure.

Figure 34:
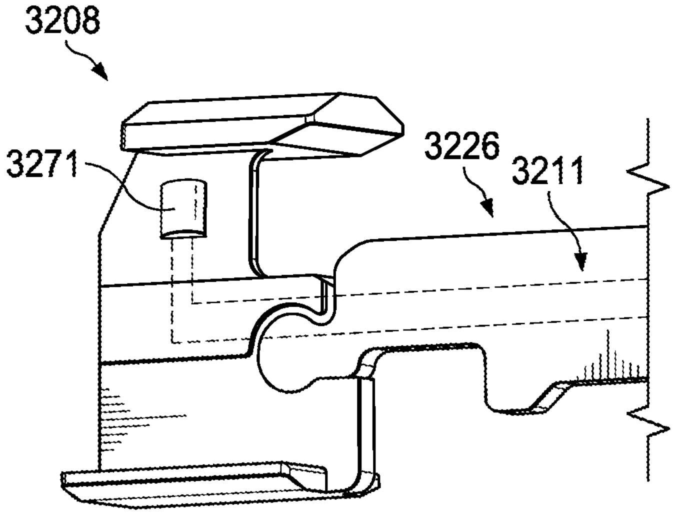

FIG. 34 depicts an example blade assembly 3208 that includes another example resistive heating element 3271. The resistive heating element 3271 can be energized via circuitry 3211 extending along the beam 3226. While FIG. 34 depicts a resistive heating element 3271 placed on only a first side of the blade assembly 3208, it is to be appreciated that other embodiments can also have a similar resistive heating element placed on the other side as well. As shown, the resistive heating element 3271 can include a curved outer surface, which can aid in bringing the resistive heating element 3271 in contact with tissue during resection. Additionally, one or more tissue sensors can be incorporated into the blade assembly 3208 in accordance with the present disclosure.

Figure 35:
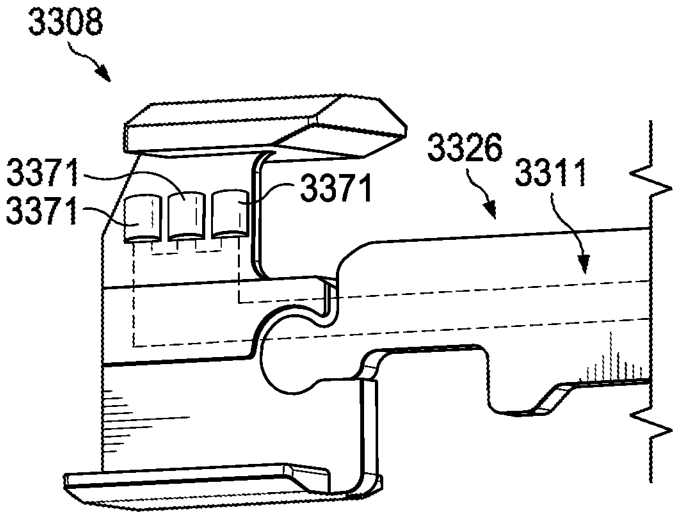

FIG. 35 depicts an example blade assembly 3308 that includes a plurality of resistive heating elements 3371. The resistive heating elements 3371 can be energized via circuitry 3311 extending along the beam 3326. While FIG. 35 depicts resistive heating elements 3371 placed on only a first side of the blade assembly 3308, it is to be appreciated that other embodiments can also have a similar resistive heating elements placed on the other side as well. As shown, the resistive heating elements 3371 include a curved outer surface, although this disclosure is not so limited. In the illustrated embodiment, the resistive heating elements 3371 are linearly arranged in the direction of travel of the beam 3326, with gaps placed therebetween. The particular spacing between adjacent resistance heating elements 3371, as well as the sizing of the resistance heating elements 3371, can be selected based on various operational parameters. By way of example, during operation, the spacing between adjacent resistance heating elements 3371 can assist in reducing the likelihood that tissue will be burnt. Further, in some embodiments, each resistance heating element 3371 can be configured to heat to substantially the same temperature while energized. In other embodiments, the operational temperature of each of various resistance heating elements 3371 can vary in order to achieve a desired temperature profile, for example. Finally, while three resistive heating elements 3371 are shown in FIG. 35, it is to be appreciated that this disclosure is not so limited, as some embodiments may utilize less than three resistive heating elements 3371 while others may utilize more than three resistive heating elements 3371. Additionally, one or more tissue sensors can be incorporated into the blade assembly 3308 in accordance with the present disclosure.

Figure 36:
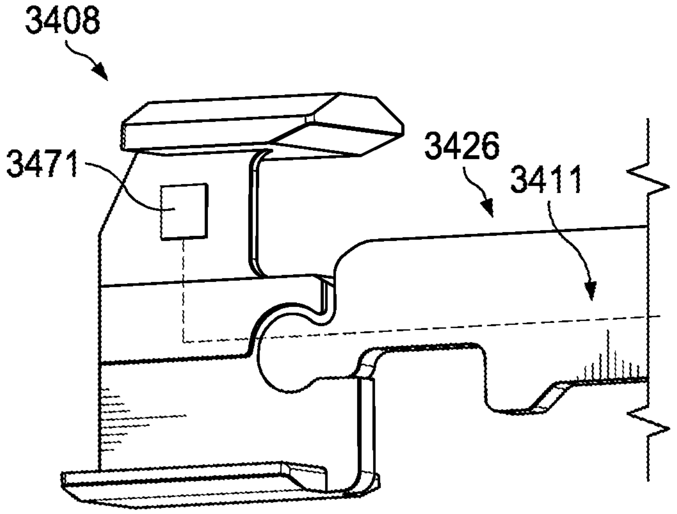

In other embodiments, instead of utilizing bipolar electrosurgical approaches or resistive heating elements to cauterize and seal tissue, some surgical devices can utilize monopolar electrosurgical techniques for delivering energy to the tissue. FIG. 36, for example, depicts an example blade assembly 3408 that includes an example active electrode 3471. The active electrode 3471 can be energized via circuitry 3411 extending along the beam 3426. During operation, a return electrode (not shown) can be attached to the patient, such that electrical current flows from the generator to the active electrode 3471, through the target tissue, then to the return electrode and back to the generator. Thus, the active electrode 3471 can be used to cauterize tissue along an incision by delivering energy into the tissue. Additionally, one or more tissue sensors can be incorporated into the blade assembly 3408 in accordance with the present disclosure.

While various embodiments are described herein in the context of endocutters, it is to be appreciated that this disclosure is not so limited. Instead, bipolar electrode arrangements in accordance with the present disclosure can be incorporated into a wide variety of surgical tools and systems having cutting edges. More particularly, electrodes in accordance with the present disclosure can be incorporated into the tools and system proximate to cutting edges that can be configured to cauterize, coagulate/desiccate, and/or seal tissue that is cut by such cutting edge.

Figure 37:
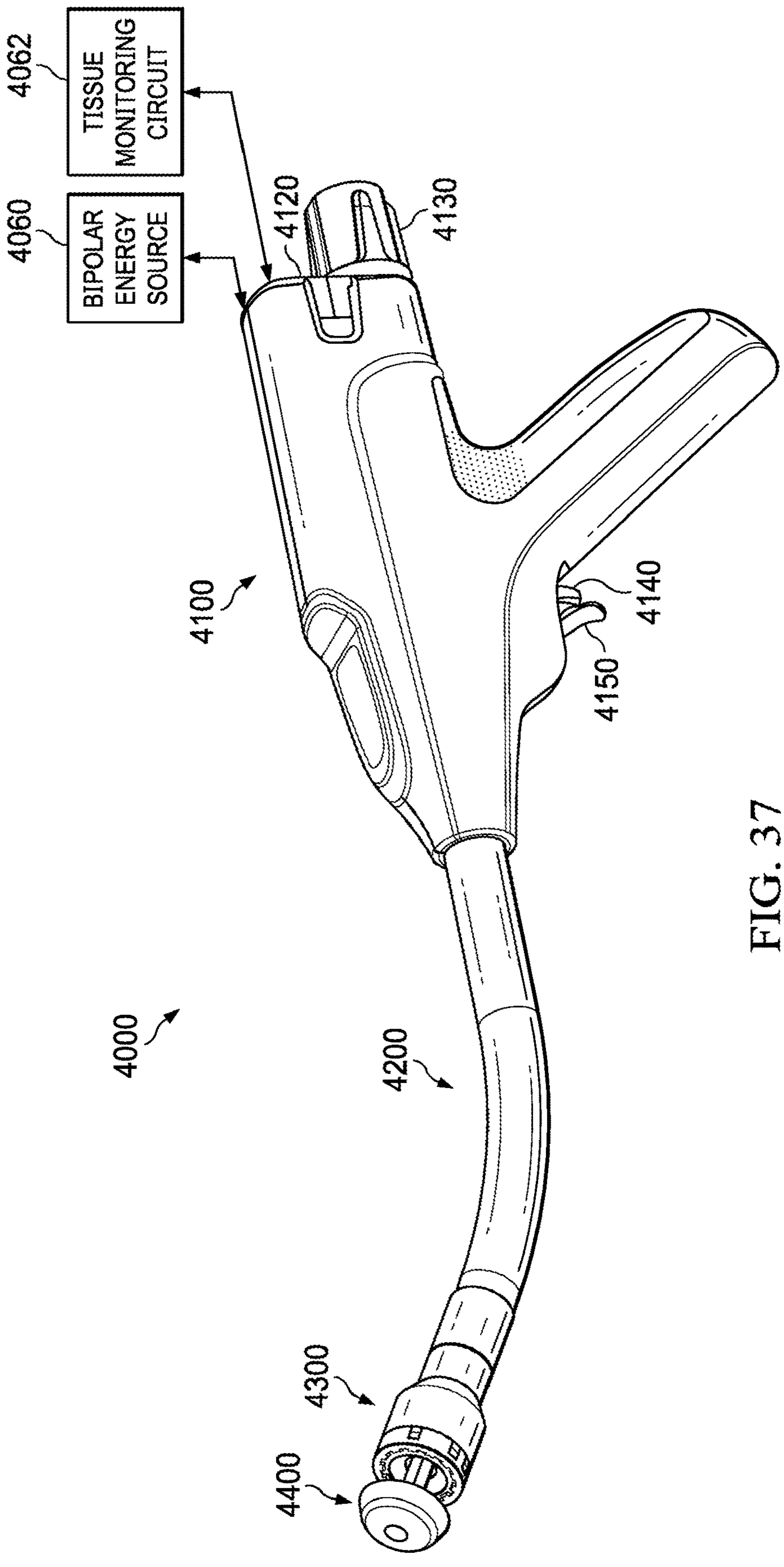
FIG. 37 is a perspective view of an exemplary electrosurgical circular stapler in accordance with an example embodiment.
Figure 38:
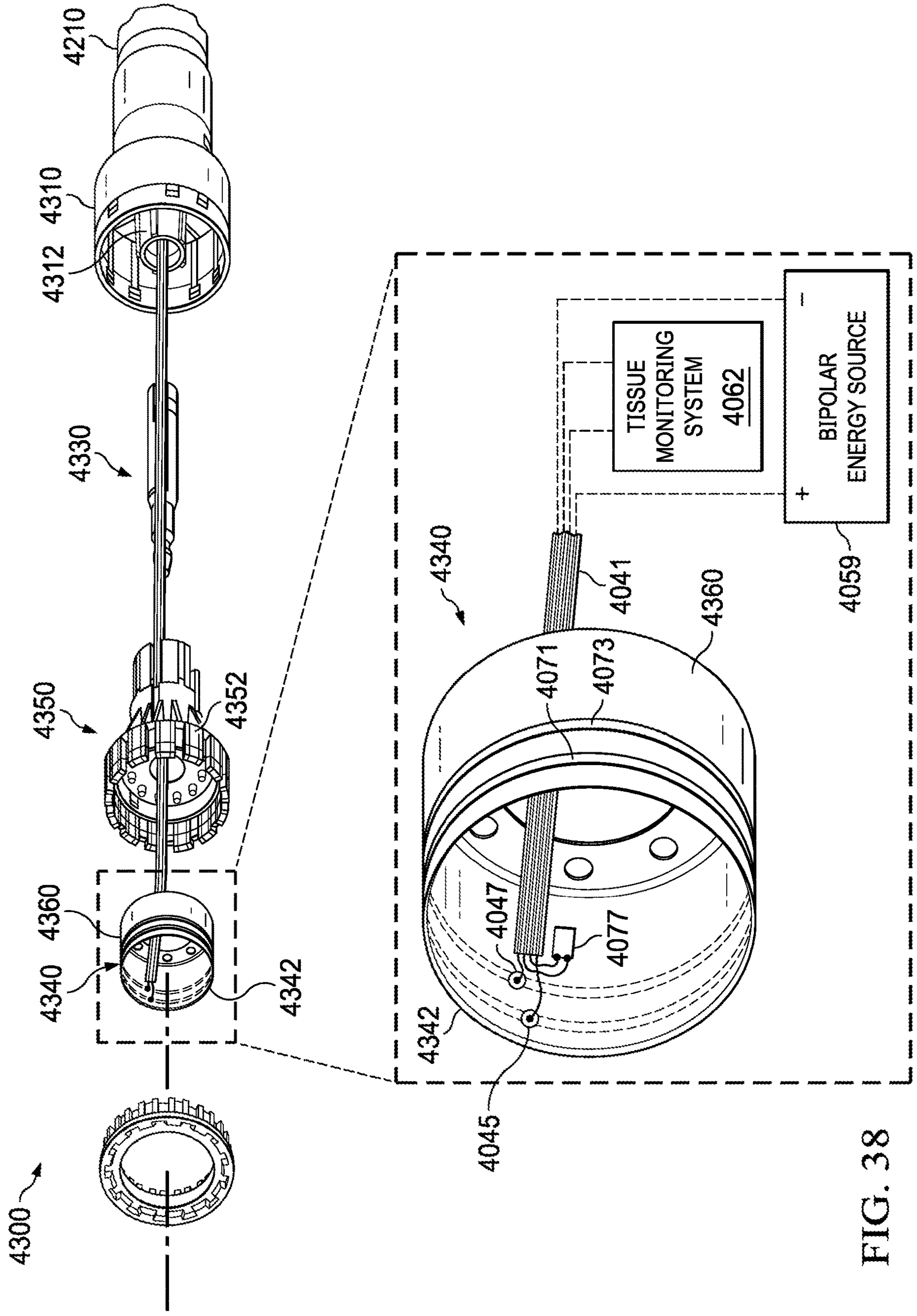
FIG. 38 depicts an exploded perspective view of the stapling head assembly of FIG. 37.
Figure 39:
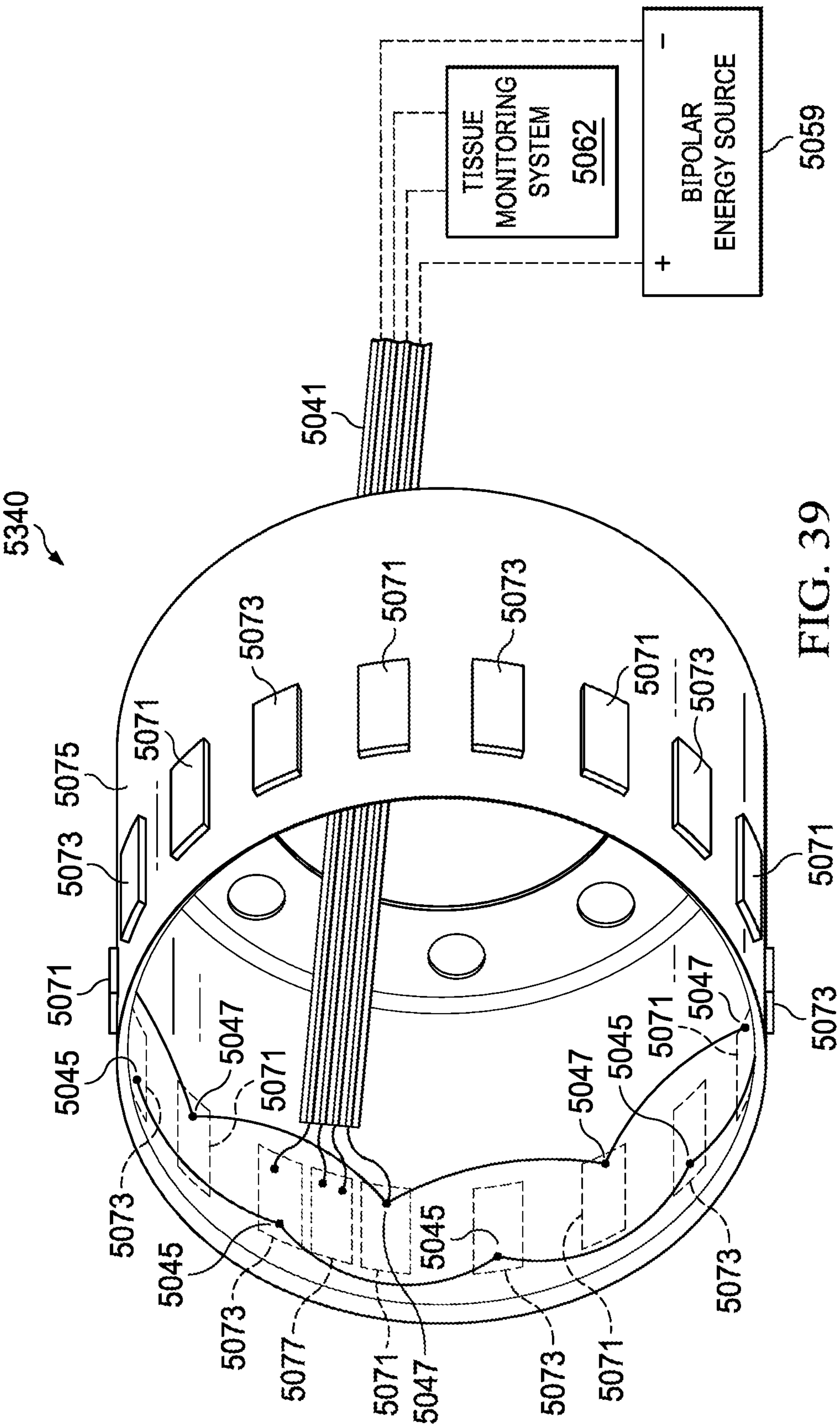
FIG. 39 depicts an example knife member of an electrosurgical circular stapler in accordance with an example embodiment.

Referring first to FIGS. 37-39, an example electrosurgical circular stapler 4000 in accordance with the present disclosure is illustrated. The example electrosurgical circular stapler 4000 can be used to provide an end-to-end, side-to-side, or end-to-side anastomosis between two sections of an anatomical lumen such as a portion of a patient's digestive tract. The electrosurgical circular stapler 4000 can comprises a handle assembly 4100, a shaft assembly 4200, a stapling head assembly 4300 and an anvil 4400.

The electrosurgical circular stapler 4000 can further include a connection 4120 to a bipolar energy source 4060 and a tissue monitoring system 4062. The bipolar energy source 4060 can be configured to deliver electrosurgical energy to electrodes positioned in the stapling head assembly 4300. Stapling head assembly 4300 is located at the distal end of shaft assembly 4200. The anvil 4400 is configured to removably couple with shaft assembly 4200, adjacent to stapling head assembly 4300. The anvil 4400 and stapling head assembly 4300 can cooperate to clamp the tissue, cut the tissue, staple the tissue, and seal the tissue. A knob 4130 at the proximal end of handle assembly 4100 can be rotatable relative to casing 4110 to provide precise clamping of the tissue between anvil 4400 and stapling head assembly 4300. When a safety trigger 4140 of handle assembly 4100 is pivoted away from a firing trigger 4150 is of handle assembly 4100, the firing trigger 4150 may be actuated to thereby provide cutting, stapling, and sealing of the tissue.

FIG. 38 provides an exploded view of the stapling head assembly 4300. The stapling head assembly 4300 can include a body member 4310 and a slidable staple driver member 4350. The body member 4310 includes a distally extending cylindraceous inner core member 4312. The body member 4310 is fixedly secured to an outer sheath 4210 of shaft assembly 4200 (FIG. 37).

As shown in FIG. 38, the stapling head assembly 4300 can further include a trocar 4330 and a circular knife member 4340 that is coaxially positioned within staple driver member 4350. The knife member 4340 includes a distally presented, sharp circular cutting edge 4342. The knife member 4340 is sized such that knife member 4340 defines an outer diameter that is smaller than the diameter defined by the inner annular array of staple drivers 4352. The knife member 4340 has a cylindrical wall 4360 upon which first and second electrodes 4071, 4073 are positioned. One or more tissue sensors 4077 can also be positioned on the cylindrical wall 4360. Other suitable structural relationships between knife member 4340 and staple driver member 4350 will be apparent to those of ordinary skill in the art in view of the teachings herein.

As shown in the enlarged view of the knife member 4340 in FIG. 38, the first and second electrodes 4071, 4073 can be in electrical communication with first and second contacts 4045, 4047, respectively. A flexible circuit 4041 can be in electrical communication with the first and second contacts 4045, 4047 and a bipolar energy source 4059, for example. While FIG. 38 depicts first and second electrodes 4071, 4073 that are generally rings surrounding the knife member 4340, this disclosure is not so limited. FIG. 39, for example, depicts a knife member 5340 having a plurality of laterally spaced electrodes 5071, 5073 that are positioned in an alternating fashion around its outer surface 5075. The electrodes 5071, 5073 can be in communication with a bipolar energy source 5059 via a flexible circuit 5041, for example. In this embodiment, the electrodes 5071 are shown as "active" electrodes and are in communication with the bipolar energy source 5059 via contacts 5045. Electrodes 5073 are shown as "passive" electrodes and are in communication with the bipolar energy source 5059 via contacts 5047. One or more tissue sensors 5077 can also be positioned on knife member 4340 that are in communication with a tissue monitoring system 5062.

Figure 40:
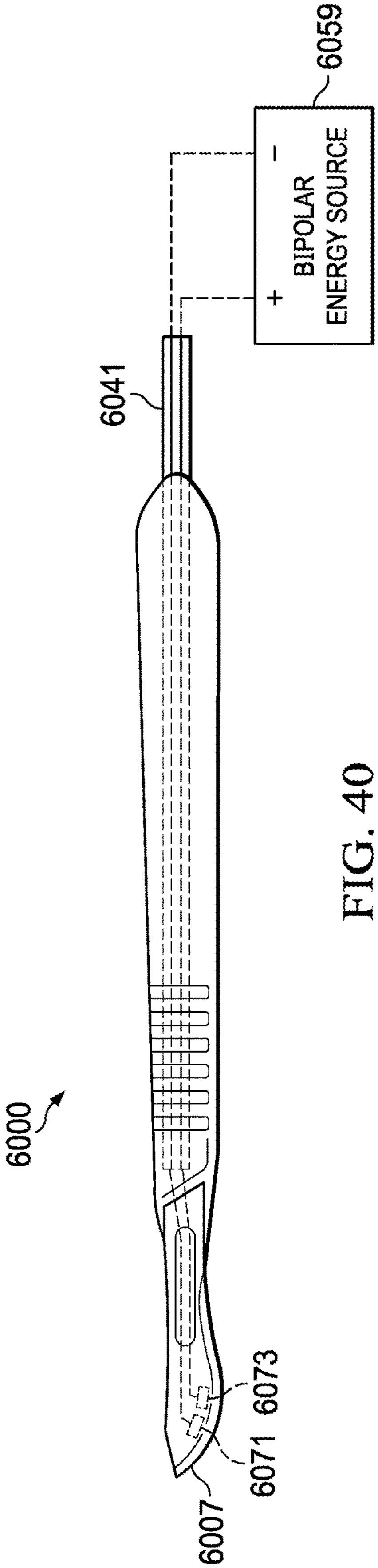
FIGS. 40-41 depict example bladed electrosurgical instruments.
Figure 41:
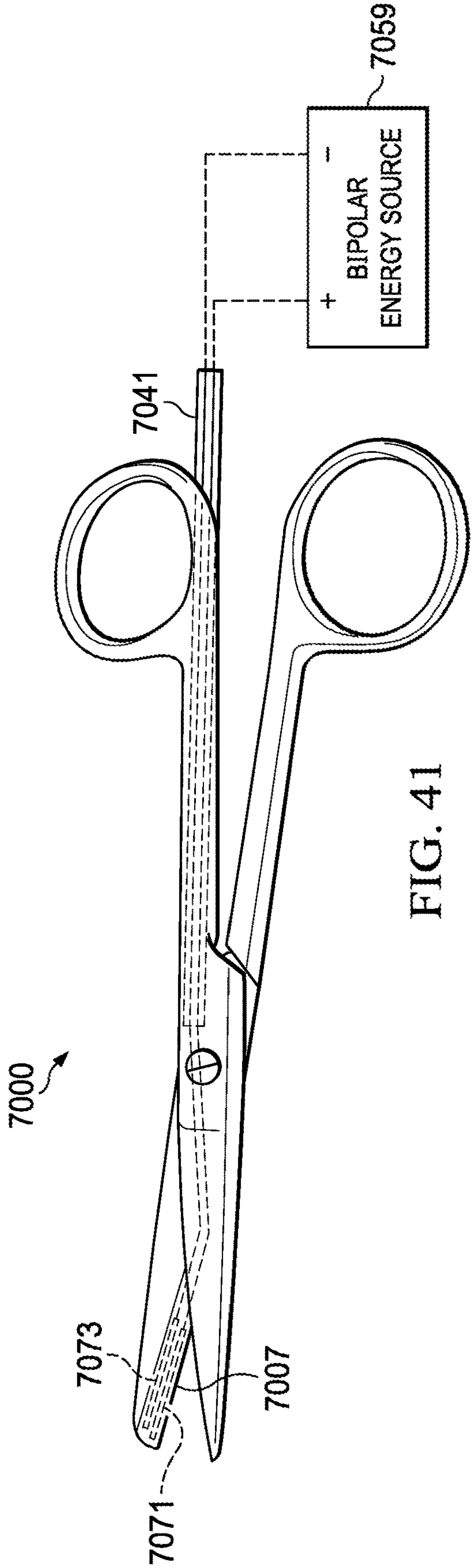

Furthermore, the systems and methods described herein can be used with a variety of different types of bladed medical tools and instruments, some non-limiting examples of which are schematically illustrated in FIGS. 40-41. Referring first to FIG. 40, an electrosurgical scalpel 6000 that is in electrical communication with a bipolar energy source 6059 is shown. The electrosurgical scalpel 6000 can include two electrodes 6071, 6073 that are positioned proximate to a cutting edge 6007 at the distal end. The electrodes 6071, 6073 can be in electrical communication with the bipolar energy source 6059 via a flexible circuit 6041, among a variety of other suitable connection techniques. Referring next to FIG. 41, electrosurgical scissors 7000 that are in electrical communication with a bipolar energy source 6059 is shown. The electrosurgical scissors 7000 can include two electrodes 7071, 7073 that are positioned proximate to a cutting edge 7007 of the scissors. The electrodes 7071, 7073 can be in electrical communication with the bipolar energy source 7059 via a flexible circuit 7041, among a variety of other suitable connection techniques. Additionally, one or more tissue sensors can be incorporated into the electrosurgical scalpel 6000 and/or the electrosurgical scissors 7000 in accordance with the present disclosure.

Figure 42:
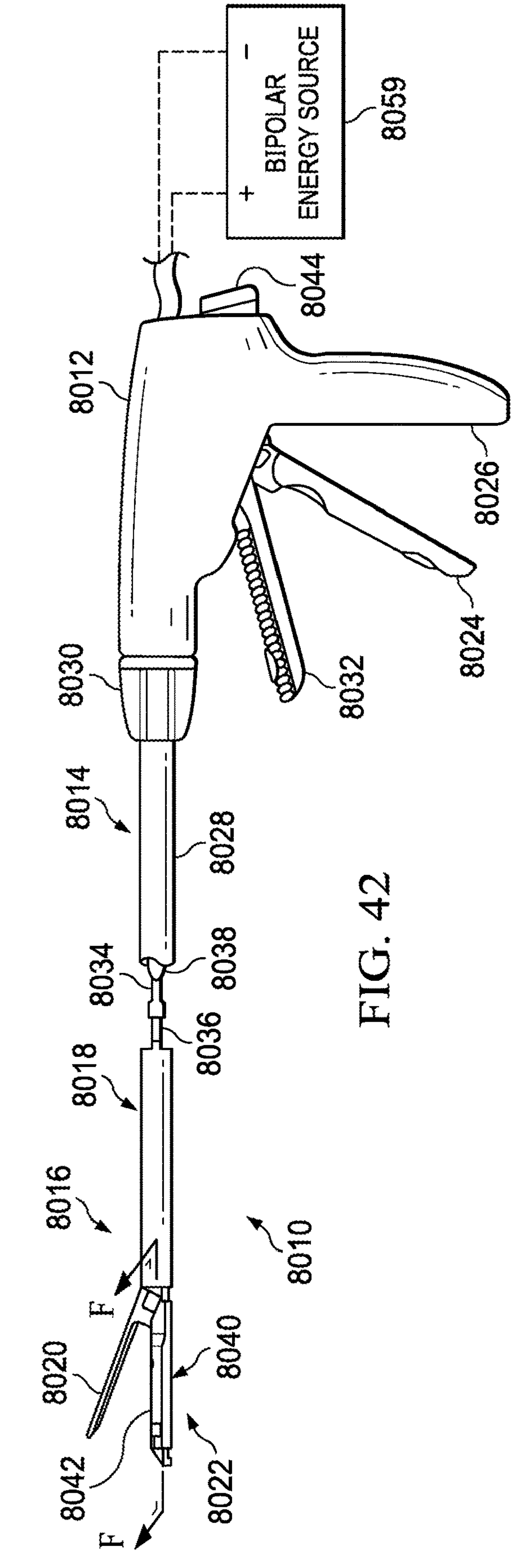
FIG. 42 is a left side view in elevation of an electrosurgical stapling and severing instrument with an open end effector (staple applying assembly) with a shaft partially cut away to expose a firing member of a proximal firing rod and distal firing bar guided by a frame ground and encompassed by a closure sleeve.
Figure 43:
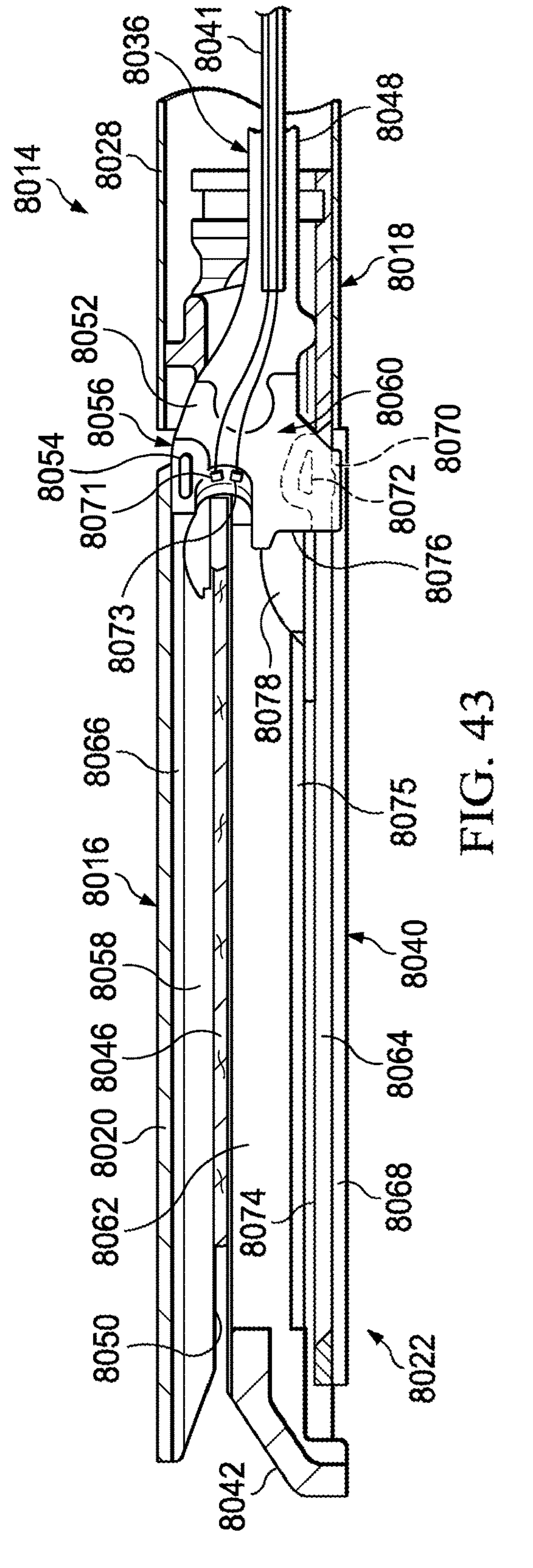
FIG. 43 is a left side view of a closed end effector (staple applying assembly) with a retracted force adjusted height firing bar consistent with the present invention of the surgical stapling and severing instrument of FIG. 42 taken in longitudinal vertical cross section along taken along section F-F.
Figure 44:
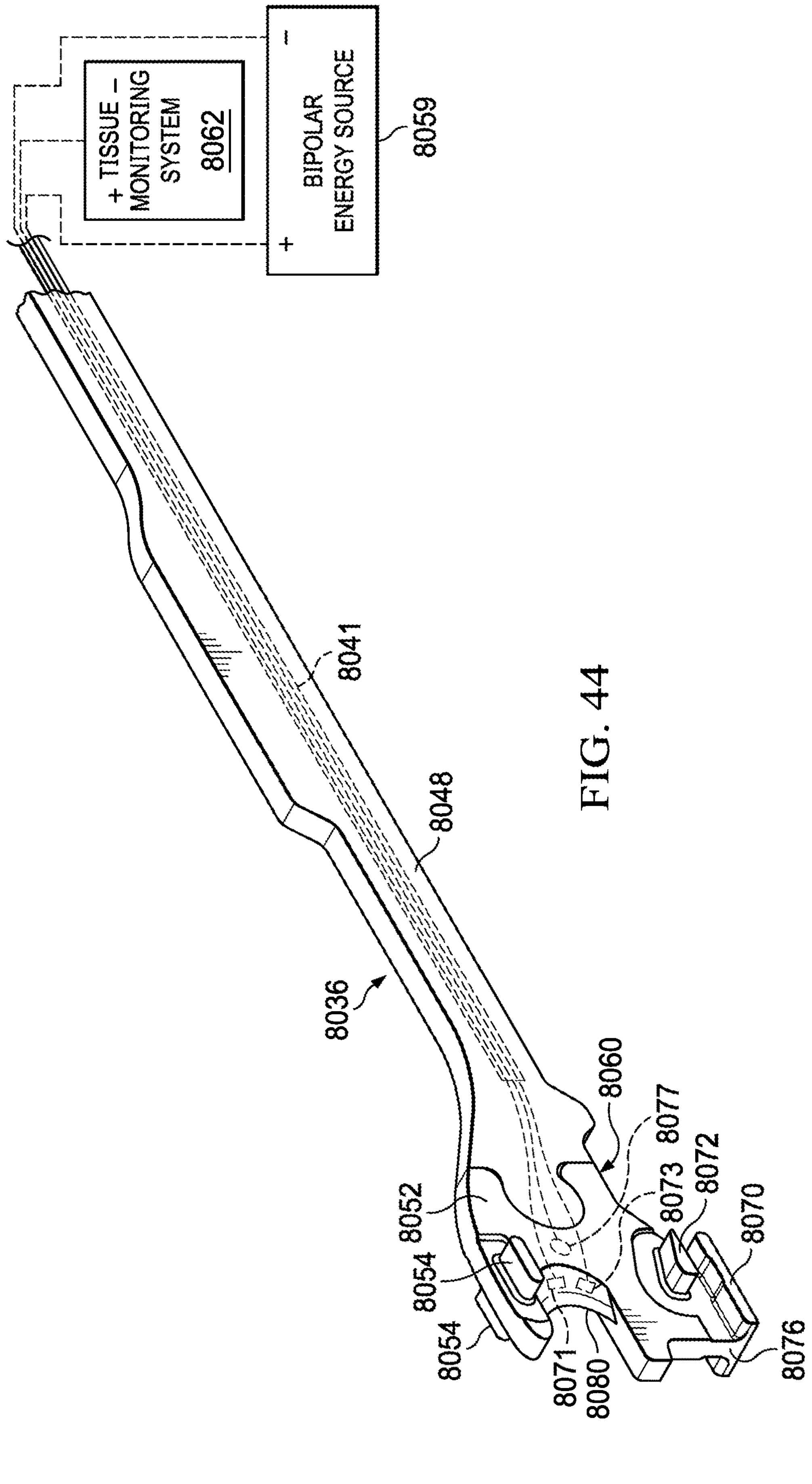
FIG. 44 is a left isometric view of the firing bar of FIG. 43.

FIGS. 42-44 depict an electrosurgical stapling and severing instrument in accordance with various non-limiting embodiment, with FIG. 43 showing a cross-sectional view of the end effector and FIG. 44 showing the firing bar. Referring first to FIG. 42, the electrosurgical stapling and severing instrument 8010 includes a handle portion 8012 that is manipulated to position an implement portion 8014 including a fastening end effector, depicted as a staple applying assembly 8016, distally attached to an elongate shaft 8018. The implement portion 8014 is sized for insertion through a cannula of a trocar (not shown) for an endoscopic or laparoscopic surgical procedure with an upper jaw (anvil) 8020 and a lower jaw 8022 of the staple applying assembly 8016 closed by depression of a closure trigger 8024 toward a pistol grip 8026 of the handle portion 8012, which advances an outer closure sleeve 8028 of the elongate shaft 8018 to pivot shut the anvil 8020.

Once inserted into an insufflated body cavity or lumen, the surgeon may rotate the implement portion 8014 about its longitudinal axis by twisting a shaft rotation knob 8030 that engages across a distal end of the handle 8012 and a proximal end of the elongate shaft 8018. Thus positioned, the closure trigger 8024 may be released, opening the anvil 8020 so that tissue may be grasped and positioned. Once satisfied with the tissue held in the staple applying assembly 8016, the surgeon depresses the closure trigger 8024 until locked against the pistol grip 8026, clamping tissue inside of the staple applying assembly 8016.

Then a firing trigger 8032 is depressed, drawn toward the closure trigger 8024 and pistol grip 8026, thereby applying a firing force or motion thereto to distally advance a firing member from an unfired position. The firing member is depicted as including a proximal firing rod 8034 attached to a distal firing bar 8036, that is supported within a frame ground 8038 that connects the handle portion 8012 to the staple applying assembly 8016. During the staple firing motion, the firing bar 8036 engages an elongate staple channel 8040 and actuates a staple cartridge 8042 contained therein, both forming the lower jaw 8022. The firing bar 8036 also engages the closed anvil 8020. After releasing the firing trigger 8032 to apply a retraction force or motion to the firing bar 8036, depression of a closure release button 8044 unclamps the closure trigger 8024 so that the closure sleeve 8028 may be retracted to pivot and open the anvil 8020 to release the severed and stapled tissue from the staple applying assembly 8016.

In FIG. 43, the staple applying assembly 8016 is closed upon compressed tissue 8046. In FIGS. 43 and 44, the firing bar 8036 has a proximal portion 8048 that is attached to a distal E-beam 8060 that translates within the staple applying assembly 8016. As depicted with the firing bar 8036 retracted, a vertical portion 8052 of the E-beam 8060 resides essentially aft of the staple cartridge 8042, as after a new staple cartridge 8042 has been inserted into the elongate staple channel 8040. An upper pin 8054 that extends laterally from an upper portion of the vertical portion 8052 of the E-beam 8060 initially resides within an anvil pocket 8056 recessed near a proximal pivoting end of the anvil 8020. As the E-beam 8060 is distally advanced during the staple firing motion, the vertical portion 8052 passes through a narrow longitudinal anvil slot 8058 formed in a staple forming undersurface 8050 of the anvil 8020, a proximally open vertical slot 8062 formed in cartridge 8042 and an underlying longitudinal channel slot 8064 formed in the elongate staple channel 8040.

The narrow longitudinal anvil slot 8058 communicates upwardly to a laterally widened longitudinal anvil channel 8066 sized to slidingly receive the upper pin 8054. The longitudinal channel slot 8064 communicates downwardly to a laterally widened longitudinal channel track 8068 that receives a lower foot 8070, which is sized to slide therein and is attached at a bottom of the vertical portion 8052 of the E-beam 8060. A laterally widened middle pin 8072 extending from the vertical portion 8052 of the E-beam 8060 is positioned to slide along a top surface of a bottom tray 8074 of the staple cartridge 8042, which in turn rests upon the elongate staple channel 8040. A longitudinal firing recess 8075 formed in the staple cartridge 8042 above the bottom tray 8074 is sized to allow the middle pin 8072 to translate through the staple cartridge 8042.

A distal driving surface 8076 of the vertical portion 8052 of the E-beam 8060 is positioned to translate through the proximally open vertical slot 8062 of the staple cartridge 8042 and distally drive a wedge sled 8078 proximally positioned in the staple cartridge 8042. The vertical portion 8052 of the E-beam 8060 includes a cutting surface 8080 along a distal edge above the distal driving surface 8076 and below the upper pin 8054 that severs the clamped tissue 8046 simultaneously with this stapling.

First and second electrodes 8071, 8073 can be positioned on the E-beam 8060. The First and second electrodes 8071, 8073 can be in electrical communication with a bipolar energy source 8059 via circuitry 8041 and can be activated during distal advancement of the E-beam 8060 through the tissue 8046. While first and second electrodes 8071, 8073 are shown positioned on only a first side of the E-beam 8060, this disclosure is not so limited. Instead, one or more electrodes can be placed on either side of the E-beam 8060 to effect hemostasis by heating the tissue 8046 and blood vessels to cauterize, coagulate/desiccate, and/or seal the tissue 8046. Additionally, one or more tissue sensors 8077 can be positioned on the E-beam 8060 that are in communication with a tissue monitoring system 8062.

In various embodiments disclosed herein, a single component can be replaced by multiple components and multiple components can be replaced by a single component to perform a given function or functions. Except where such substitution would not be operative, such substitution is within the intended scope of the embodiments. For example, staple leg heights, staple material of manufacture, anvil pocket depths, anvil pocket shapes and anvil pocket asymmetry may all be varied in any combination.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed:

1. An electrosurgical surgical instrument, the surgical instrument comprising:

(a) an end effector, the end effector comprising:

(i) an anvil that includes a first end, a second end, and an anvil face positionable on a first side of an anatomical structure;

(ii) a cartridge operably configured to house a plurality of staples, the cartridge comprising a first end, a second end, and a face positionable on a second side of the anatomical structure;

(iii) a blade assembly comprising a blade, wherein the blade includes a first side and a second side joined at a cutting edge;

(iv) at least one electrode coupled to the blade, wherein the at least one electrode is in electrical communication with an electrosurgical power source and a controller; and (v) at least one tissue sensor coupled to the blade; and (b) a tissue monitoring system, including the controller, in electrical communication with the at least one tissue sensor, wherein the at least one tissue sensor provides feedback signals indicative of a property of the tissue to the controller, and wherein the controller signals the electrosurgical power source to adjust operational parameters of the electrosurgical surgical instrument based on the feedback signals;

wherein the feedback signals relate to a tissue temperature of the anatomical structure; and wherein a firing speed of the electrosurgical surgical instrument is decreased if the tissue temperature at a predetermined tissue location along a resection line of the anatomical structure has not reached a target temperature, and wherein firing of the electrosurgical surgical instrument is stopped if the tissue temperature rises above a predetermined threshold.

2. The electrosurgical surgical instrument of claim 1, wherein the blade further comprises a proximal portion forming the cutting edge, so that as the blade is advanced from a first position at a distal end of the cartridge to a second position at a proximal end of the cartridge:

(a) an incision is formed in the anatomical structure; and (b) the at least one electrode and the at least one tissue sensor contact the anatomical structure and translate along the anatomical structure.

3. The electrosurgical surgical instrument of claim 1, wherein the controller includes analog or logic circuitry for:

(a) processing the feedback signals received from the at least one tissue sensor; and (b) determining the signals sent to the electrosurgical power source.

4. The electrosurgical surgical instrument of claim 1, wherein circuitry connects the at least one electrode to the electrosurgical power source and the at least one tissue sensor to the tissue monitoring system.

5. The electrosurgical surgical instrument of claim 1, wherein the electrosurgical power source is terminated once the tissue temperature rises above the predetermined threshold.

6. The electrosurgical surgical instrument of claim 5, wherein the predetermined threshold of the tissue temperature is between 80-120° C.

7. The electrosurgical surgical instrument of claim 1, wherein the target temperature of the predetermined tissue location is between 60-100° C.

8. The electrosurgical surgical instrument of claim 1, wherein the feedback signals relate to tissue impedance of the anatomical structure.

9. The electrosurgical surgical instrument of claim 8, wherein the electrosurgical power source is terminated if the tissue impedance at a predetermined tissue location of the anatomical structure has not reached a target impedance of 200 Ohms.

10. The electrosurgical surgical instrument of claim 8, wherein the firing speed of the electrosurgical surgical instrument is slowed if the tissue impedance rises above a predetermined threshold value of 600 Ohms.

11. An electrosurgical surgical instrument to staple, resect, and seal an anatomical structure of a patient, the surgical instrument comprising:

(a) an end effector, the end effector comprising:

(i) an anvil that includes a first end, a second end, and an anvil face positionable on a first side of the anatomical structure;

(ii) a cartridge operably configured to house a plurality of staples, the cartridge comprising a first end, a second end, and a face positionable on a second side of the anatomical structure;

(iii) a blade assembly comprising a blade and a beam, wherein the blade includes a first side and a second side joined at a cutting edge;

(iv) at least one electrode coupled to the blade, wherein the at least one electrode is in electrical communication with an electrosurgical power source and a controller; and (v) at least one tissue sensor coupled to the blade; and (b) a tissue monitoring system, including the controller, in electrical communication with the at least one tissue sensor, wherein the at least one tissue sensor provides tissue impedance feedback signals to the controller as the blade is advanced from a first position at a distal end of the cartridge to a second position at a proximal end of a cartridge, and wherein the controller signals the electrosurgical power source to adjust firing speed of the electrosurgical surgical instrument based on the tissue impedance feedback signals;

wherein the at least one tissue sensor further provides a tissue temperature feedback signals to the controller; and wherein a firing speed of the electrosurgical surgical instrument is slowed if the tissue temperature at a predetermined tissue location along a resection line of the anatomical structure has not reached a target temperature between 60-100° C., and wherein firing of the electrosurgical surgical instrument is stopped if the tissue temperature rises above a predetermined threshold.

12. The electrosurgical surgical instrument of claim 11, wherein the blade further comprises a proximal portion forming the cutting edge, so that as the blade is advanced from the first position at the distal end of the cartridge to the second position at the proximal end of the cartridge:

(a) an incision is formed in the anatomical structure; and (b) the at least one electrode and the at least one tissue sensor contact the anatomical structure and translate along the anatomical structure.

13. The electrosurgical surgical instrument of claim 11, wherein the controller includes analog or logic circuitry for:

(a) processing the feedback signals received from the at least one tissue sensor; and (b) determining the signals sent to the electrosurgical power source.

14. The electrosurgical surgical instrument of claim 11, wherein the electrosurgical power source is terminated if the tissue impedance at a predetermined tissue location of the anatomical structure has not reached a target impedance of 200 Ohms.

15. The electrosurgical surgical instrument of claim 11, wherein the firing speed of the electrosurgical surgical instrument is slowed if the tissue impedance rises above a predetermined threshold value of 600 Ohms.

16. The electrosurgical surgical instrument of claim 11, wherein the electrosurgical power source is terminated once the tissue temperature rises above the predetermined threshold of between 80-120° C.

* * * * *